(12) United States Patent
Rudolf et al.

(10) Patent No.: US 10,426,817 B2
(45) Date of Patent: Oct. 1, 2019

(54) TREATMENT OF AGE-RELATED MACULAR DEGENERATION AND OTHER EYE DISEASES WITH APOLIPOPROTEIN MIMETICS

(71) Applicant: MacRegen, Inc., San Jose, CA (US)

(72) Inventors: Martin Rudolf, Luebeck (DE); Keith Roizman, San Jose, CA (US)

(73) Assignee: MacRegen, Inc., San Jose, CA (US)

( * ) Notice: Subject to any disclaimer, the term of this patent is extended or adjusted under 35 U.S.C. 154(b) by 15 days.

(21) Appl. No.: 15/414,422

(22) Filed: Jan. 24, 2017

(65) Prior Publication Data
US 2018/0207233 A1 Jul. 26, 2018

(51) Int. Cl.
| | | |
|---|---|---|
| A61K 38/17 | (2006.01) | |
| A61K 45/06 | (2006.01) | |
| A61K 9/00 | (2006.01) | |
| C07K 14/775 | (2006.01) | |

(52) U.S. Cl.
CPC ........ *A61K 38/1709* (2013.01); *A61K 9/0048* (2013.01); *A61K 45/06* (2013.01); *C07K 14/775* (2013.01); *C07K 2319/30* (2013.01)

(58) Field of Classification Search
CPC ...... A61K 38/00; A61K 38/10; A61K 9/0048; C07K 14/775; G01N 2333/775
See application file for complete search history.

(56) References Cited

U.S. PATENT DOCUMENTS

| | | | |
|---|---|---|---|
| 6,664,230 B1 | 12/2003 | Fogelman et al. | |
| 6,933,279 B2 | 8/2005 | Fogelman et al. | |
| 7,144,862 B2 | 12/2006 | Fogelman et al. | |
| 7,148,197 B2 | 12/2006 | Fogelman et al. | |
| 7,166,578 B2 | 1/2007 | Fogelman et al. | |
| 7,199,102 B2 | 4/2007 | Fogelman et al. | |
| 7,470,659 B2 | 12/2008 | Schwartz et al. | |
| 7,470,660 B2 | 12/2008 | Schwartz et al. | |
| 7,531,514 B2 | 5/2009 | Fogelman et al. | |
| 7,723,303 B2 | 5/2010 | Fogelman et al. | |
| 7,807,640 B2 | 10/2010 | Fogelman et al. | |
| 7,820,784 B2 | 10/2010 | Fogelman et al. | |
| 7,994,132 B2 | 8/2011 | Fogelman et al. | |
| 8,048,851 B2 | 11/2011 | Fogelman et al. | |
| 8,404,635 B2 | 3/2013 | Fogelman et al. | |
| 8,568,766 B2* | 10/2013 | Anantharamaiah .. | A61K 9/0019 424/429 |
| 9,241,976 B2 | 1/2016 | Farias-Eisner et al. | |
| 2003/0045460 A1 | 3/2003 | Fogelman et al. | |
| 2003/0162758 A1 | 8/2003 | Schwartz et al. | |
| 2003/0171277 A1 | 9/2003 | Fogelman et al. | |
| 2003/0229015 A1 | 12/2003 | Fogelman et al. | |
| 2003/0229062 A1 | 12/2003 | Schwartz et al. | |
| 2004/0254120 A1 | 12/2004 | Fogelman et al. | |
| 2004/0266663 A1* | 12/2004 | Schwartz ............... | A61K 31/66 514/7.4 |
| 2004/0266671 A1 | 12/2004 | Fogelman et al. | |
| 2005/0164950 A1 | 7/2005 | Fogelman et al. | |
| 2005/0282750 A1 | 12/2005 | Schwartz et al. | |
| 2007/0032430 A1 | 2/2007 | Fogelman et al. | |
| 2007/0060527 A1 | 3/2007 | Fogelman et al. | |
| 2007/0254839 A1 | 11/2007 | Fogelman et al. | |
| 2008/0045459 A1 | 2/2008 | Fogelman et al. | |
| 2008/0095821 A1 | 4/2008 | Fogelman et al. | |
| 2008/0096814 A1 | 4/2008 | Fogelman et al. | |
| 2008/0096815 A1 | 4/2008 | Fogelman et al. | |
| 2008/0096816 A1 | 4/2008 | Fogelman et al. | |
| 2008/0293639 A1 | 11/2008 | Fogelman et al. | |
| 2010/0047330 A1 | 2/2010 | Schwartz et al. | |
| 2010/0143444 A1 | 6/2010 | Anantharamaiah | |
| 2010/0227825 A1 | 9/2010 | Fogelman et al. | |
| 2011/0182992 A1 | 7/2011 | Anantharamaiah | |

(Continued)

FOREIGN PATENT DOCUMENTS

| | | |
|---|---|---|
| EP | 1864675 A1 | 12/2007 |
| EP | 1864675 B1 | 12/2007 |

(Continued)

OTHER PUBLICATIONS

Karen Robbins. Pet Rats & Mice—General Care. American Fancy Rat and Mouse Association. Mar. 6, 2015. (Year: 2015).*
Martin et al. Ranibizumab and bevacizumab for neovascular age-related macular degeneration. N Engl J Med. May 19, 2011;364(20):1897-908. (Year: 2011).*
FDA Guidance for Industry Estimating the Maximum Safe Starting Dose in Initial Clinical Trials for Therapeutics in Adult Healthy Volunteers. Jul. 2005. (Year: 2005).*
Tomita et al. Relationship between hemodynamics and atherosclerosis in aortic arches of apolipoprotein E-null mice on 129S6/SvEvTac and C57BL/6J genetic backgrounds. Atherosclerosis. Jan. 2012;220(1):78-85. (Year: 2012).*

(Continued)

*Primary Examiner* — Marcela M Cordero Garcia
*Assistant Examiner* — Jia-Hai Lee
(74) *Attorney, Agent, or Firm* — The Marbury Law Group, PLLC

(57) ABSTRACT

The present disclosure provides apolipoprotein (apo) mimetics useful for the treatment of age-related macular degeneration (AMD) and other eye disorders. The apo mimetics can be peptides/polypeptides that mimic, e.g., the lipid-clearing action of apolipoproteins such as apoA-I and apoE. The apo mimetics can exert other beneficial effects, such as reduction of inflammation, oxidative stress and neovascularization. The apo mimetics can be used to treat any stages (including the early, intermediate and advance stages) of AMD, and any phenotypes of AMD, including geographic atrophy (GA) (including non-central GA and central GA) and neovascularization (NV) (including types 1, 2 and 3 NV). The apo mimetics can be used alone or in conjunction with other therapeutic agents, such as a complement inhibitor and/or an anti-angiogenic agent, to treat AMD, including atrophic AMD and neovascular AMD, and other eye disorders.

24 Claims, 6 Drawing Sheets
Specification includes a Sequence Listing.

(56) References Cited

U.S. PATENT DOCUMENTS

| | | |
|---|---|---|
| 2012/0035095 A1 | 2/2012 | Fogelman et al. |
| 2013/0295042 A1 | 11/2013 | Anantharamaiah |
| 2014/0323410 A1 | 10/2014 | Farias-Eisner et al. |

FOREIGN PATENT DOCUMENTS

| | | | |
|---|---|---|---|
| EP | 1318828 B1 | 4/2010 | |
| EP | 2198877 A2 | 6/2010 | |
| EP | 2198877 B1 | 6/2010 | |
| EP | 2269623 A1 | 1/2011 | |
| EP | 2368561 A1 | 9/2011 | |
| EP | 2368561 B1 | 9/2011 | |
| WO | WO-02/15923 A1 | 2/2002 | |
| WO | WO-03/049685 A2 | 6/2003 | |
| WO | WO-03/049685 A3 | 6/2003 | |
| WO | WO-2004/034977 A2 | 4/2004 | |
| WO | WO-2004/034977 A3 | 4/2004 | |
| WO | WO-2004/098506 A2 | 11/2004 | |
| WO | WO-2004/098506 A3 | 11/2004 | |
| WO | WO-2005/016280 A2 | 2/2005 | |
| WO | WO-2005/016280 A3 | 2/2005 | |
| WO | WO-2005/091909 A2 | 10/2005 | |
| WO | WO-2005/091909 A3 | 10/2005 | |
| WO | WO-2006/118805 A2 | 11/2006 | |
| WO | WO-2006/118805 A3 | 11/2006 | |
| WO | WO-2009/073725 A2 | 6/2009 | |
| WO | WO-2009/100348 A2 | 8/2009 | |
| WO | WO-2009/100348 A3 | 8/2009 | |
| WO | WO2009100348 A2 * | 8/2009 | ............. A61K 38/16 |
| WO | WO-2013/033260 A1 | 3/2013 | |

OTHER PUBLICATIONS

Ambati, J. et al. (Jun. 2013). "Immunology of Age-Related Macular Degeneration," *Nature Reviews* 13:438-451.

Anantharamaiah, G.M. et al. (1993). "An Atlas of the Amphipathic Helical Domains of Human Exchangeable Plasma Apolipoproteins," Chapter 6 in *The Amphipathic Helix*, Epand, R.M. ed., CRC Press, Boca Raton, FL, pp. 109-142.

Bloedon, L.T. et al. (Mar. 2008). "Safety, Pharmacokinetics, and Pharmacodynamics of Oral apoA-I Mimetic Peptide D-4F in High-Risk Cardiovascular Patients," *J. Lipid Res.* 49:1344-1352.

Curcio, C.A. et al. (2011; e-pub Sep. 2, 2011). "The Oil Spill in Ageing Bruch Membrane," *Br. J. Ophthalmol.* 95(12):1638-1645.

Del V Cano, M. et al. (2008). "PPAR-α Ligands as Potential Therapeutic Agents for Wet Age-Related Macular Degeneration," *PPAR Research* 2008(article ID 821592):1-5.

Evans, J.B. et al. (Jul. 2013). "New Hope for Dry AMD?," *Nat. Rev. Drug Discov.* 12(7):501-502.

Freund, K.B. et al. (2015) "Treat-and-Extend Regimens with Anti-VEGF Agents in Retinal Diseases," *Retina* 0(0):1-18.

Gehlbach, P. et al. (Oct. 2013). "Statins for Age-Related Macular Degeneration," *Cochrane Database Syst. Rev.* 3:1-18.

Girmens, J.F. et al. (2012). "Dry Age-Related Macular Degeneration: A Currently Unmet Clinical Need," *Intract. & Rare Dis. Res.* 1(3):103-114.

Jager, R.D. et al. (Jun. 12, 2008). "Age-Related Macular Degeneration," *N. Engl. J. Med.* 358:2606-2617.

John, B. (Mar. 2007). "Intravitreal Injections", *Kerala J. Ophthalmol.* XIX(1):46-57.

Leung, E. et al. (2013). "Update on Current and Future Novel Therapies for Dry Age-Related Macular Degeneration," *Expert Rev. Clin. Pharmacol.*, 6(5):565-579.

Miller J.W. (Jan. 2013). "Age-Related Macular Degeneration Revisited—Piecing the Puzzle: The LXIX Edward Jackson Memorial Lecture," *Am. J. Ophthalmol.* 155(1):1-35; *Supplemental Materials* 155(1):35.e2-35.e13.

Pikuleva, I.A. et al. (Jul. 2014). "Cholesterol In The Retina: The Best Is Yet To Come," *Prog. Ret. Eye Res.* 41:64-89.

Ratner, M. (Aug. 2014). "Next-Generation AMD Drugs to Wed Blockbusters," *Nat. Biotech.* 32(8):701-702.

Reddy, S.T. et al. (Aug. 2014). "Apolipoprotein A-I Mimetics," *Curr. Opin. Lipidol.* 25(4):304-308.

Rhoades, W. et al. (2015). "Potential Role of Lampalizumab for Treatment of Geographic Atrophy," *Clin. Ophthalmol.* 9:1049-1056.

Rudolf, M. et al. (Apr. 2010) "ApoA-I Mimetic Peptide Reduces Lipid Deposition in Murine Bruch's Membrane after Intravitreal Injection", Abstract for ARVO Annual Meeting in Fort Lauderdale in May 2010, Investig. Ophthalmol. & Vis. Sci., vol. 51, p. 2984.

Rudolf, M. et al., (Sep. 12, 2014). "ApoA-I Mimetic Peptide L-4F Reduces Significantly Lipid Deposits in Bruch's Membrane and Complement Activation in Geriatric Monkeys with Age-Related Maculopathy," Abstract for 14th EURETINA Congress in London, printed Mar. 21, 2017.

Rudolf, M. et al. (May 2015). "ApoA-I Mimetic Peptide L-4F Reduces Significantly Lipid Deposits in Bruch's Membrane and Complement Activation in Geriatric Monkeys with Age-Related Maculopathy," Abstract No. 1279 for ARVO Annual Meeting in Denver printed Apr. 30, 2015.

Schmidt-Erfurth, U.A. et al. (2014). "Guidelines for the Management of Neovascular Age-Related Macular Degeneration by the European Society of Retina Specialists (EURETINA)," *Br. J. Ophthalmol* 98:1144-1167.

Schmidt-Erfurth, U. A. et al. (2007). "Guidance for the Treatment of Neovascular Age-Related Macular Degeneration," *Acta Ophthalmol. Scand.* 85:486-494.

Schrezenmeier, H. et al. (2012). "Drugs that Inhibit Complement,", *Transfusion and Apheresis Science* 46:87-92.

Shapiro, A. et al. (Jul./Aug. 2013). "Ongoing Trials in AMD," *Retina Today* pp. 24-26.

Sharifov, O. F. et al. (2011). "Apolipoprotein E Mimetics and Cholesterol-Lowering Properties," *Am. J. Cardiovasc. Drugs* 11(6):371-381.

Singer, M. (May 6, 2014). "Advances in the Management of Macular Degeneration," *F1000Prime Reports* 6:29, pp. 1-5.

Watson, C.E. et al. (2011). "Treatment of Patients with Cardiovascular Disease with L-4F, An Apo-A1 Mimetic, Did Not Improve Select Biomarkers of HDL Function," *J. Lipid Res.* 52:361-373.

White, C.R. et al. (Aug. 2014). "Anti-Inflammatory and Cholesterol-Reducing Properties of Apolipoprotein Mimetics: A Review," *J. Lipid Res.* 55:2007-2021.

Anantharamaiah, G.M. et al. (2016). "Apolipoprotein Mimetic Peptides as Modulators of Lipoprotein Function," *Protein & Peptide Letters* 23(11):1024-1031.

D'Souza, W. et al. (Jul. 23, 2010). "Structure/Function Relationships of Apolipoprotein A-I Mimetic Peptides Implications for Antiatherogenic Activities of High-Density Lipoprotein," *Circ Res.* 107:217-227.

Ikenaga, M. (2016). "High-Density Lipoprotein Mimetics: A Therapeutic Tool for Atherosclerotic Diseases," *J Atheroscler Thromb* 23(4):385-394.

Klaver, C. C. W. et al. (Jul. 1, 1998). "Genetic Association of Apolipoprotein E with Age-Related Macular Degeneration," *American Journal of Human Genetics* 63(1):200-206.

Navab, M. et al. (Sep. 1, 2003). "Human Apolipoprotein AI Mimetic Peptides for the Treatment of Atherosclerosis," *Curr. Opin. Investig. Drugs* 4(9):1100-1104.

OTC Disclosure & News Service. (Dec. 19, 2016). "Capstone Therapeutics Announces Profound, Rapid LDL Cholesterol Reduction in AEM-28-14 Primate Study", OTC Markets Retrieved from the Internet: URL<https://www.otcmarkets.com/stock/CAPS/news/Capstone-Therapeutics-Announces-Profound--Rapid-LDL-Cholesterol-Reduction-in-AEM-28-14-Primate-Study?id=I47356&b=y>, Last visited on Sep. 18, 2017.

Querques, G. (2014; Published online Sep. 11, 2014). "Treatment of Dry Age-Related Macular Degeneration," *Ophthalmic Res* 52:107-115.

Recio, C. et al. (Jan. 6, 2017). "The Potential Therapeutic Appliciton of Peptides and Peptidomimetics in Cardiovascular Disease," *Frontiers in Pharmacology* 7(526)1-11.

(56) References Cited

OTHER PUBLICATIONS

Stoekenbroek, R.M. (2015). "ApoA-I Mimetics," Chapter 21 in *High Density Lipoproteins*, Von Eckardstein et al. eds., Handbook of Experimental Pharmacology 224:631-648.
Uehara, Y. et al. (Dec. 2015). "High-Density Lipoprotein-Targeted Therapy and Apolipoprotein A-I Mimetic Peptides," *Circ J* 79:2523-2528.
Written Opinion of the International Search Authority, dated Oct. 25, 2017, for PCT Application No. PCT/US2017/014754, filed on Jan. 24, 2017, 9 pages.
International Search Report dated Oct. 25, 2017, for PCT Application No. PCT/US2017/014754, filed on Jan. 24, 2017, 6 pages.

\* cited by examiner

SEQUENCE LISTING

```
<160> NUMBER OF SEQ ID NOS: 32

<210> SEQ ID NO 1
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: AMIDATION
```

<222> LOCATION: 23

<400> SEQUENCE: 1

Cys Gly Val Leu Glu Ser Phe Lys Ala Ser Phe Leu Ser Ala Leu Glu
1               5                   10                  15

Glu Trp Thr Lys Lys Leu Gln
            20

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

Asp Trp Leu Lys Ala Phe Tyr Asp Lys Val Ala Glu Lys Leu Lys Glu
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Asp Trp Phe Lys Ala Phe Tyr Asp Lys Val Ala Glu Lys Phe Lys Glu
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: Synthetic Construct

<400> SEQUENCE: 4

Asp Trp Phe Lys Ala Phe Tyr Asp Lys Val Ala Glu Lys Phe Lys Glu
1               5                   10                  15

Ala Phe

<210> SEQ ID NO 5
<211> LENGTH: 37
<212> TYPE: PRT
<213> ORGANISM: Artificial Sequence
<220> FEATURE:
<223> OTHER INFORMATION: Synthetic Construct

<400> SEQUENCE: 5

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 6
<211> LENGTH: 37
<212> TYPE: PRT
<213> ORGANISM: Artificial Sequence
<220> FEATURE:
<223> OTHER INFORMATION: Synthetic Construct

<400> SEQUENCE: 6

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
                20                  25                  30

Leu Lys Glu Phe Phe
            35

<210> SEQ ID NO 7
<211> LENGTH: 37
<212> TYPE: PRT
<213> ORGANISM: Artificial Sequence
<220> FEATURE:
<223> OTHER INFORMATION: Synthetic Construct

<400> SEQUENCE: 7

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
                20                  25                  30

Leu Lys Glu Ala Phe
            35

<210> SEQ ID NO 8
<211> LENGTH: 37
<212> TYPE: PRT
<213> ORGANISM: Artificial Sequence
<220> FEATURE:
<223> OTHER INFORMATION: Synthetic Construct

<400> SEQUENCE: 8

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
                20                  25                  30

Leu Lys Glu Ala Phe
            35

<210> SEQ ID NO 9
<211> LENGTH: 37
<212> TYPE: PRT
<213> ORGANISM: Artificial Sequence
<220> FEATURE:
<223> OTHER INFORMATION: Synthetic Construct

<400> SEQUENCE: 9

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
                20                  25                  30

Phe Lys Glu Phe Leu
            35

<210> SEQ ID NO 10
<211> LENGTH: 37
<212> TYPE: PRT
<213> ORGANISM: Artificial Sequence
<220> FEATURE:
<223> OTHER INFORMATION: Synthetic Construct

<400> SEQUENCE: 10

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
        35

<210> SEQ ID NO 11
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11, 17
<223> OTHER INFORMATION: Xaa = 2-aminoisobutyric acid

<400> SEQUENCE: 11

Asp Trp Phe Lys Ala Phe Tyr Asp Lys Val Xaa Glu Lys Phe Lys Glu
1               5                   10                  15

Xaa Phe

<210> SEQ ID NO 12
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11, 17
<223> OTHER INFORMATION: Xaa = 2-aminoisobutyric acid
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 12

Asp Trp Phe Lys Ala Phe Tyr Asp Lys Val Xaa Glu Lys Phe Lys Glu
1               5                   10                  15

Xaa Phe

<210> SEQ ID NO 13
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 13

Asp Trp Phe Lys Ala Phe Tyr Asp Lys Val Ala Glu Lys Phe Lys Glu
1               5                   10                  15

Ala Phe

<210> SEQ ID NO 14
<211> LENGTH: 2
<212> TYPE: PRT
<213> ORGANISM: Artificial Sequence
<220> FEATURE:
<223> OTHER INFORMATION: Synthetic Construct

```
<220> FEATURE:
<221> NAME/KEY: VARIANT
<222> LOCATION: 1
<223> OTHER INFORMATION: Xaa = quinoline-2-carbonyl-Val (i.e., Val,
      where the N-terminus is quinoline-2-carbonyl)
<220> FEATURE:
<221> NAME/KEY: VARIANT
<222> LOCATION: 2
<223> OTHER INFORMATION: Xaa = Asp(OMe)-2,6- difluorophenoxymethylketone
      (i.e., Asp, where the side-chain is methyl ester group, and
      the C-terminus is 2,6-difluorophenoxymethylketone)

<400> SEQUENCE: 14

Xaa Xaa
1

<210> SEQ ID NO 15
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = tert-butyloxycarbonyl-Asp(OMe)-
      fluoromethylketone

<400> SEQUENCE: 15

Xaa
1

<210> SEQ ID NO 16
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Val
<220> FEATURE:
<221> NAME/KEY: VARIANT
<222> LOCATION: 3
<223> OTHER INFORMATION: Xaa = Asp(OMe)-NH2

<400> SEQUENCE: 16

Xaa Ala Xaa
1

<210> SEQ ID NO 17
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Val
<220> FEATURE:
<221> NAME/KEY: VARIANT
<222> LOCATION: 3
<223> OTHER INFORMATION: Xaa = Asp(OMe)-fluoromethylketone

<400> SEQUENCE: 17

Xaa Ala Xaa
1

<210> SEQ ID NO 18
```

```
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Tyr
<220> FEATURE:
<221> NAME/KEY: VARIANT
<222> LOCATION: 4
<223> OTHER INFORMATION: Xaa = Asp(OMe)-fluoromethylketone

<400> SEQUENCE: 18

Xaa Val Ala Xaa
1

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Val
<220> FEATURE:
<221> NAME/KEY: VARIANT
<222> LOCATION: 2
<223> OTHER INFORMATION: Xaa = Asp(OMe)
<220> FEATURE:
<221> NAME/KEY: VARIANT
<222> LOCATION: 5
<223> OTHER INFORMATION: Xaa = Asp(OMe)-fluoromethylketone

<400> SEQUENCE: 19

Xaa Xaa Val Ala Xaa
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = quinoline-2-carbonyl-Asp(OMe)
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-2,6-difluorophenoxymethylketone

<400> SEQUENCE: 20

Xaa Xaa Val Xaa
1

<210> SEQ ID NO 21
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
```

```
<223> OTHER INFORMATION: Xaa = benzyloxycarbonyl-Asp(OMe)
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-fluoromethylketone

<400> SEQUENCE: 21

Xaa Xaa Val Xaa
1

<210> SEQ ID NO 22
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Asp(OMe)
<220> FEATURE:
<221> NAME/KEY: VARIANT
<222> LOCATION: 4
<223> OTHER INFORMATION: Xaa = Asp(OMe)-fluoromethylketone

<400> SEQUENCE: 22

Xaa Gln Met Xaa
1

<210> SEQ ID NO 23
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Leu
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-fluoromethylketone

<400> SEQUENCE: 23

Xaa Xaa Val Xaa
1

<210> SEQ ID NO 24
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Trp
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
```

<223> OTHER INFORMATION: Xaa = Asp(OMe)-fluoromethylketone

<400> SEQUENCE: 24

Xaa Xaa His Xaa
1

<210> SEQ ID NO 25
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Val
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-fluoromethylketone

<400> SEQUENCE: 25

Xaa Xaa Ile Xaa
1

<210> SEQ ID NO 26
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = quinoline-2-carbonyl-Ile
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-2,6-difluorophenoxymethylketone

<400> SEQUENCE: 26

Xaa Xaa Thr Xaa
1

<210> SEQ ID NO 27
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Ile
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-fluoromethylketone

<400> SEQUENCE: 27

Xaa Xaa Thr Xaa
1

<210> SEQ ID NO 28
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = quinoline-2-carbonyl-Leu
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-2,6-difluorophenoxymethylketone

<400> SEQUENCE: 28

Xaa Xaa His Xaa
1

<210> SEQ ID NO 29
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Leu
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-fluoromethylketone

<400> SEQUENCE: 29

Xaa Xaa His Xaa
1

<210> SEQ ID NO 30
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Ala
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-fluoromethylketone

<400> SEQUENCE: 30

Xaa Xaa Val Xaa
1

```
<210> SEQ ID NO 31
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Ala
<220> FEATURE:
<221> NAME/KEY: VARIANT
<222> LOCATION: 4
<223> OTHER INFORMATION: Xaa = Asp(OMe)-fluoromethylketone

<400> SEQUENCE: 31

Xaa Thr Ala Xaa
1

<210> SEQ ID NO 32
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = benzyloxycarbonyl-Leu
<220> FEATURE:
<221> NAME/KEY: VARIANT
<222> LOCATION: 2
<223> OTHER INFORMATION: Xaa = Glu(OMe)
<220> FEATURE:
<221> NAME/KEY: VARIANT
<222> LOCATION: 3
<223> OTHER INFORMATION: Xaa = Glu(OMe)
<220> FEATURE:
<221> NAME/KEY: VARIANT
<222> LOCATION: 4
<223> OTHER INFORMATION: Xaa = Asp(OMe)-fluoromethylketone

<400> SEQUENCE: 32

Xaa Xaa Xaa Xaa
1
```

TREATMENT OF AGE-RELATED MACULAR DEGENERATION AND OTHER EYE DISEASES WITH APOLIPOPROTEIN MIMETICS

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 774462000100SEQLISTING.txt, date recorded: Mar. 30, 2017, size: 12 KB).

BACKGROUND OF THE DISCLOSURE

Age-related macular degeneration (AMD) affects about 14-24% of the people aged 65 to 74 and about 35% of the people over 75 around the world, and results in vision impairment or loss in the center of the visual field (the macula) because of damage to the retina. It is a major cause of vision loss and potentially blindness in people over 50 years of age. The two principal forms of AMD are atrophic (non-exudative or "dry") AMD and neovascular (exudative or "wet") AMD. Atrophic AMD is characterized by geographic atrophy (GA) at the center of the macula in the advanced stage of AMD, and vision can slowly deteriorate over many years due to loss of photoreceptors and development of GA. Neovascular AMD is a more severe form of AMD and is characterized by neovascularization (e.g., choroidal neovascularization) in the advanced stage of AMD, which can rapidly lead to blindness. Neovascular AMD affects more than 30 million patients worldwide and is a leading cause of vision loss in people aged 60 years or older—if untreated, patients are likely to lose central vision in the affected eye within 24 months of disease onset. About 90% of AMD patients have the dry form, and about 10% develop neovascular AMD. There is no approved treatment for atrophic AMD in the United States, while approved treatments for neovascular AMD (primarily anti-angiogenic agents) show efficacy in about 50% of neovascular AMD patients.

SUMMARY OF THE DISCLOSURE

The present disclosure provides apolipoprotein (apo) mimetics for the treatment of AMD and other eye diseases and disorders. In some embodiments, an apoA-I mimetic and/or an apoE mimetic are administered to treat AMD or another eye disorder. In certain embodiments, the apoA-I mimetic comprises, or is, L-4F or D-4F. In some embodiments, the apoE mimetic comprises, or is, AEM-28-14. One or more other therapeutic agents can be administered in combination with an apo mimetic to treat AMD or another eye disorder. The one or more other therapeutic agents can be selected to target different underlying factors of AMD or the other eye disorder. An apo mimetic, optionally in conjunction with another therapeutic agent, can be administered to treat, e.g., AMD in different stages (including the early, intermediate and advanced stages) of AMD and for different phenotypes of AMD (including geographic atrophy and neovascular AMD), and to prevent or slow the progression to the next stage of AMD.

In addition to apolipoprotein mimetics, other therapeutic agents that can be used to treat AMD and other eye diseases and disorders include without limitation:

1) anti-dyslipidemic agents;
2) PPAR-α agonists, PPAR-δ agonists and PPAR-γ agonists;
3) anti-amyloid agents;
4) inhibitors of lipofuscin or components thereof;
5) visual/light cycle modulators and dark adaptation agents;
6) antioxidants;
7) neuroprotectors (neuroprotectants);
8) apoptosis inhibitors and necrosis inhibitors;
9) C-reactive protein inhibitors;
10) inhibitors of the complement system or components (e.g., proteins) thereof;
11) inhibitors of inflammasomes;
12) anti-inflammatory agents;
13) immunosuppressants;
14) modulators of matrix metalloproteinases; and
15) anti-angiogenic agents.

Besides AMD, other eye diseases and disorders that can be treated with an apolipoprotein mimetic, optionally in conjunction with one or more other therapeutic agents, include without limitation maculopathy (e.g., age-related maculopathy and diabetic maculopathy), macular edema (e.g., diabetic macular edema [DME] and macular edema following retinal vein occlusion [RVO]), retinopathy (e.g., diabetic retinopathy [including in patients with DME]), RVO (e.g., central RVO and branch RVO), Coats' disease (exudative retinitis), uveitis, retinal pigment epithelium detachment, and diseases associated with increased intra- or extracellular lipid storage or accumulation in addition to AMD.

BRIEF DESCRIPTION OF THE DRAWINGS

A better understanding of features and advantages of the present disclosure will be obtained by reference to the following detailed description, which sets forth illustrative embodiments of the disclosure, and the accompanying drawings.

DETAILED DESCRIPTION OF THE DISCLOSURE

Figure 1:
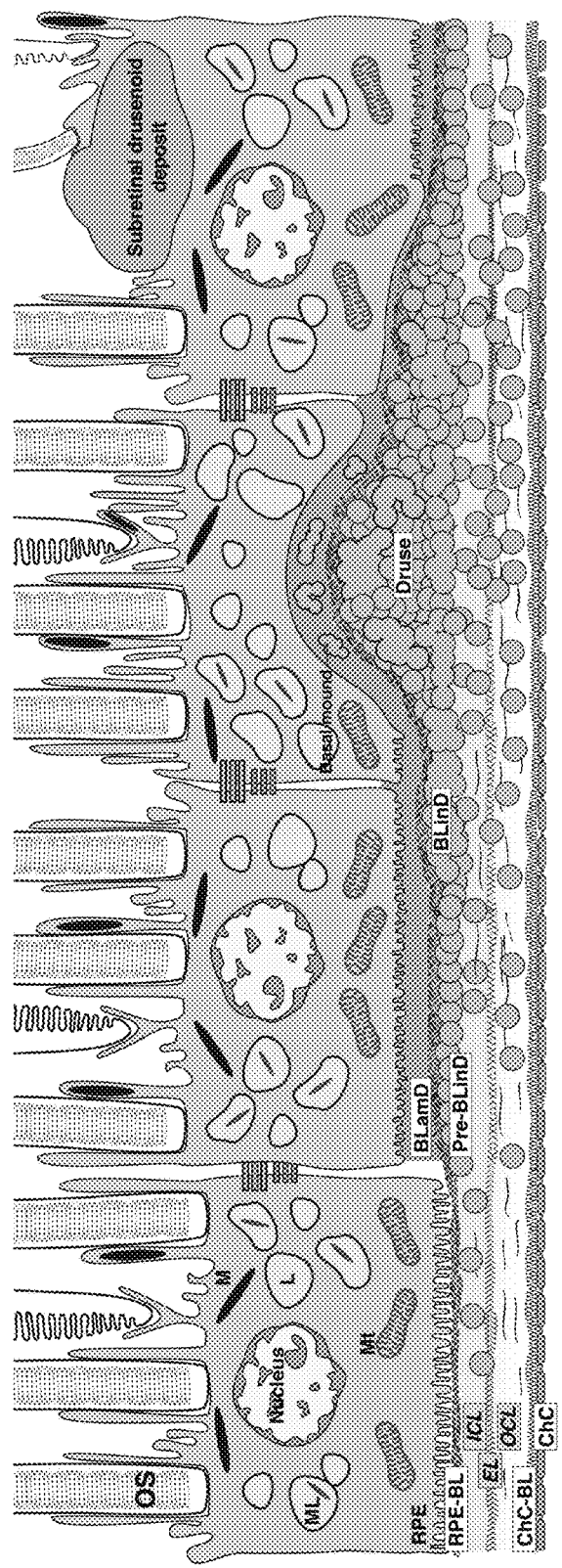
FIG. 1 illustrates tissue layers involved in AMD pathology and the role of lipid accumulation in AMD pathogenesis. OS: outer segment of photoreceptors; RPE: retinal pigment epithelium; RPE-BL: RPE basal lamina; ICL: inner collagenous layer; EL: elastic layer; OCL: outer collagenous layer; ChC-BL: ChC basal lamina; ChC: choriocapillaris endothelium; BLamD: basal laminar deposit; BLinD: basal linear deposit; pre-BLinD: pre-basal linear deposit; L: lipofuscin; M: melanosome; ML: melanolipofuscin; Mt: mitochondria; circles: lipoprotein particles. The Bruch's membrane (BrM) consists of the ICL, EL and OCL. BlamD is a thickening of the RPE-BL. Basal mound is soft druse material within BLamD. RPE cells contain melanosome, lipofuscin and melanolipofuscin, which provide signals for, e.g., color fundus photography, fundus autofluorescence and optical coherence tomography.

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein may be employed in practicing the disclosure. It is also understood that every embodiment of the disclosure may optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act, the order of the acts of the method is not necessarily limited to the order in which the acts of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

It is further understood that the present disclosure encompasses analogs, derivatives, prodrugs, fragments, salts, solvates, hydrates, clathrates and polymorphs of all of the compounds/substances disclosed herein, as appropriate. The specific recitation of "analogs", "derivatives", "prodrugs", "fragments", "salts", "solvates", "hydrates", "clathrates" or "polymorphs" with respect to a compound/substance or a group of compounds/substances in certain instances of the disclosure shall not be interpreted as an intended omission of any of these forms in other instances of the disclosure where the compound/substance or the group of compounds/substances is mentioned without recitation of any of these forms.

Headings are included herein for reference and to aid in locating certain sections. Headings are not intended to limit the scope of the embodiments and concepts described in the sections under those headings, and those embodiments and concepts may have applicability in other sections throughout the entire disclosure.

All patent literature and all non-patent literature cited herein are incorporated herein by reference in their entirety to the same extent as if each patent literature or non-patent literature were specifically and individually indicated to be incorporated herein by reference in its entirety.

I. Definitions

As used in the specification and the appended claims, the indefinite articles "a" and "an" and the definite article "the" can include plural referents as well as singular referents unless specifically stated otherwise.

The term "exemplary" as used herein means "serving as an example, instance, or illustration". Any embodiment characterized herein as "exemplary" is not necessarily to be construed as preferred or advantageous over other embodiments.

The term "about" or "approximately" means an acceptable error for a particular value as determined by one of ordinary skill in the art, which depends in part on how the value is measured or determined. In certain embodiments, the term "about" or "approximately" means within one standard deviation. In some embodiments, when no particular margin of error (e.g., a standard deviation to a mean value given in a chart or table of data) is recited, the term "about" or "approximately" means that range which would encompass the recited value and the range which would be included by rounding up or down to the recited value as well, taking into account significant figures. In certain embodiments, the term "about" or "approximately" means within 20%, 15%, 10% or 5% of the specified value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The term "antioxidants" includes without limitation substances that inhibit the oxidation of other substances, substances that retard the deterioration of other substances by oxidation, and scavengers of free radical species, reactive oxygen species, hydroxyl radical species, and oxidized lipids and lipid peroxidation products.

The term "apolipoprotein mimetics" encompasses apolipoprotein peptide mimetics and apolipoprotein mimetic peptides.

The term "conservative substitution" refers to substitution of an amino acid in a polypeptide with a functionally, structurally or chemically similar natural or unnatural amino acid. In certain embodiments, the following groups each contain natural amino acids that are conservative substitutions for one another:

1) Glycine (G), Alanine (A);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V), Alanine (A);
6) Phenylalanine (F), Tyrosine (Y), Tryptophan (W); and
7) Serine (S), Threonine (T), Cysteine (C).

In other embodiments, amino acids may be grouped as set out below:

1) hydrophobic: Met (M), Ala (A), Val (V), Leu (L), Ile (I), Phe (F), Trp (W);
2) neutral hydrophilic: Cys (C), Ser (S), Thr (T), Asn (N), Gln (Q);
3) acidic: Asp (D), Glu (E);
4) basic: His (H), Lys (K), Arg (R);
5) residues that influence backbone orientation: Gly (G), Pro (P); and
6) aromatic: Trp (W), Tyr (Y), Phe (F), His (H).

In further embodiments, the following groups each contain natural amino acids that are conservative substitutions for one another:

1) acidic: Asp, Glu;
2) basic: Lys, Arg, His;
3) uncharged polar: Gly, Ser, Thr, Cys, Tyr, Asn, Gln;
4) aliphatic hydroxyl- or sulfhydryl-containing: Ser, Thr, Cys;
5) amide-containing: Asn, Gln;
6) non-polar: Ala, Val, Leu, Ile, Met, Pro, Phe, Trp;
7) hydrophobic: Val, Leu, Ile, Phe;
8) aliphatic: Ala, Val, Leu, Ile;
9) aromatic: Phe, Trp, Tyr, His; and
10) small: Gly, Ala, Ser, Cys.

The term "pharmaceutically acceptable" refers to a substance (e.g., an active ingredient or an excipient) that is suitable for use in contact with the tissues and organs of a subject without excessive irritation, allergic response, immunogenicity and toxicity, is commensurate with a reasonable benefit/risk ratio, and is effective for its intended use. A "pharmaceutically acceptable" carrier or excipient of a pharmaceutical composition is also compatible with the other ingredients of the composition.

The term "therapeutically effective amount" refers to an amount of a substance that, when administered to a subject, is sufficient to prevent, reduce the risk of developing, delay the onset of, or slow the progression of the medical condition being treated (e.g., age-related macular degeneration [AMD]), or to alleviate to some extent one or more symptoms or complications of that condition. The term "therapeutically effective amount" also refers to an amount of a substance that is sufficient to elicit the biological or medical response of a cell, tissue, organ, system, animal or human which is sought by a researcher, veterinarian, medical doctor or clinician.

The terms "treat", "treating", and "treatment" include alleviating or abrogating a medical condition or one or more symptoms or complications associated with the condition, and alleviating or eradicating one or more causes of the condition. Reference to "treatment" of a medical condition (e.g., AMD) includes preventing (precluding), reducing the risk of developing, delaying the onset of, and slowing the progression of, the condition or one or more symptoms or complications associated with the condition.

The term "subject" refers to an animal, including a mammal, such as a primate (e.g., a human, a chimpanzee, or a monkey), a rodent (e.g., a rat, a mouse, a gerbil, or a hamster), a lagomorph (e.g., a rabbit), a swine (e.g., a pig), an equine (e.g., a horse), a canine (e.g., a dog) and a feline (e.g., a cat). The terms "subject" and "patient" are used interchangeably herein in reference, e.g., to a mammalian subject, such as a human subject.

II. Pathogenesis and Pathophysiology of AMD

Age-related changes to the retina and the choroid of the eye which contribute to the development of age-related macular degeneration (AMD) include the loss of rod photoreceptors, the thinning of the choroid, and the accumulation of lipofuscin and reportedly components thereof (e.g., A2E [N-retinylidene-N-retinyl-ethanolamine]) in the retinal pigment epithelium (RPE) as well as lipids in the sub-RPE basal lamina (sub-RPE-BL) space and the Bruch's membrane (BrM, which is part of the choroid). Lipoprotein particles and reportedly beta-amyloid (Aβ) accumulate to form basal linear deposits (BLinD) on the BrM. BLinD and drusen are believed to develop from a lipid wall that forms on the BrM. The lipid wall, and accumulation of abnormal deposits resulting in part from abnormalities in proteolytic processes in regulating the BrM, stimulate chronic inflammation. The abnormal aggregates of material, combined with the loss of normal extracellular matrix (ECM) maintenance function (partially mediated by altered ratios of matrix metalloproteinases [MMPs] and tissue inhibitors of MMPs [TIMPs]), result in alterations in the BrM, with consequent formation of BLinD and drusen. Drusen are extracellular deposits rich in lipids (e.g., esterifed cholesterol [EC] and phospholipids) and lipoprotein components (e.g., apolipoprotein B [apoB] and/or apoE) and form in the sub-RPE-BL space between the RPE-BL and the inner collagenous layer of the BrM, possibly as a result of RPE secretion of EC-rich very low-density lipoproteins (VLDLs) basolaterally. Esterified cholesterol and phospholipids (in the form of lipoprotein particles of 60-80 nm diameter) accumulate in the BrM throughout adulthood and eventually aggregate as BLinD on the BrM or soft drusen in the sub-RPE-BL space of older eyes. Soft drusen and BLinD are two forms (a lump and a thin layer, respectively) of the same lesion containing lipoprotein-derived debris. EC-rich, apoB/apoE-containing lipoproteins (e.g., VLDLs) secreted by RPE cells are retained by a BrM that progressively thickens with age, until an oily layer forms on the BrM, with oxidation of lipids or other modifications followed by fusion of individual lipoproteins over time to form BLinD. Inflammation results, and by altering the BrM with subsequent calcification and fracture, the accumulation of lipid-containing material leads to neovascularization in the sub-RPE-BL space and breakthrough to the subretinal space, the potential space between the photoreceptors and the RPE. Furthermore, the lipid-rich drusen in the sub-RPE-BL space and BLinD overlying the BrM block nutrients (including vitamin A) from reaching the photoreceptors (rods and cones) in the retina, which results in their atrophy/degeneration and eventually death. Other extracellular lesions associated with AMD include subretinal drusenoid deposits (SDD), which are compositionally distinct from drusen, contain unesterified (free) cholesterol (UC) and form between the RPE and photoreceptors, possibly as a result of RPE secretion of UC-rich lipoproteins apically. The formation of SDD in the subretinal space may also lead to sequelae such as inflammation and neovascularization (e.g., type 2 or 3).

FIG. 1 illustrates tissue layers involved in AMD pathology and the role of lipid accumulation in AMD pathogenesis. The BrM consists of three layers: the inner collagenous layer (ICL), the elastic layer (EL) and the outer collagenous layer (OCL). In healthy eyes, the RPE basal lamina (RPE-BL) is attached to the ICL of the BrM, and there is no space between the RPE-BL and the ICL (the sub-RPE-BL space is a "potential" space). Throughout adulthood RPE cells secrete lipoprotein particles (circles in FIG. 1) basally, which are dispersed in the ICL and the OCL of the BrM (the left-most panel in FIG. 1). As more lipoprotein particles are secreted and accumulate over the years, they form pre-BLinD on the tightly packed ICL of the BrM (the second-from-left panel in FIG. 1). Secretion and accumulation of more lipoprotein particles over the years result in aggregation of the lipoprotein particles to form BLinD (a layer) on the BrM ICL and soft drusen (lumps) (the two middle panels in FIG. 1). The formation of pre-BLinD creates a space between the RPE-BL and the BrM ICL (sub-RPE-BL space), which increases with the formation of BLinD and soft drusen and with a greater amount of them. The accumulation of lipid deposits, BLinD and soft drusen, elevates the RPE off the BrM ICL (the second-from-right panel in FIG. 1), and if the elevation (the sub-RPE-BL space) is sufficiently large, the RPE-BL can become detached from the BrM ICL. For instance, drusenoid pigment epithelial detachment (PED) can occur as a result of formation of soft drusen with a diameter of about 350 microns or more. As drusen grow over time, RPE cells become increasingly removed from their source of nutrients and oxygen in the choriocapillaris. Some RPE cells on the top of drusen migrate anteriorly into the neurosensory retina to seek retinal vasculature, and the RPE layer breaks up as RPE cells die, resulting in atrophy of the RPE layer. Furthermore, the lipid barrier created by BLinD and soft drusen blocks the exchange of incoming nutrients (including vitamin A) and outgoing waste between the choriocapillaris and the RPE cells, which leads to RPE cell atrophy and then death. RPE cell atrophy and death also result in the atrophy and death of photoreceptors as the RPE cells can no longer shuttle nutrients to the photoreceptors. In addition, BLinD on the BrM and soft drusen in the sub-RPE-BL space are rich sources of lipids that can be oxidized to form highly anti-inflammatory, and thus pro-angiogenic, oxidized lipids such as oxidized phospholipids. The biomechanically fragile cleavage plane created by BLinD and soft drusen are vulnerable to ramification by new blood vessels emanating from the choroid, crossing the BrM, and infiltrating the sub-RPE-BL space in type 1 neovascularization (NV) and breaking through to the subretinal space in type 2 NV, which are described below. Leakage of fluid from the neovessels into the sub-RPE-BL space in types 1 and 2 NV further contributes to the volume of the sub-RPE-BL space and the elevation of the RPE off the BrM, and thereby can cause PED.

Chronic inflammatory responses to the changes described above include complement-mediated pathways, infiltration by circulating macrophages, and activation of inflammasomes and microglia. Activation of the complement cascade leads to activation of the central component 3 (C3) and initiation of the terminal pathway with the cleavage of component 5 (C5) into C5a and C5b. The terminal pathway results in the assembly of a membrane attack complex (MAC), e.g., in the basal RPE membrane, the BrM or the choriocapillary endothelial cell membrane, by stepwise binding of C5b, C6, C7, C8 and polymerized C9 to form a pore in the lipid bilayer of the membrane. The MAC can lead to the dysfunction and death of the RPE, the BrM and/or the choriocapillary endothelium, with outer retinal atrophy ensuing. In addition, C5a elicits pro-angiogenic effects, and combined with calcification and fracture of the BrM, can contribute to NV, including choroidal NV (CNV).

The early stage of AMD (which is atrophic AMD) is characterized by the presence of a few medium-size drusen and pigmentary abnormalities such as hyperpigmentation or hypopigmentation of the RPE. The intermediate stage of AMD (which is atrophic AMD) is characterized by the presence of at least one large druse, numerous medium-size drusen, hyperpigmentation or hypopigmentation of the RPE, and geographic atrophy (GA) that does not extend to the center of the macula (non-central [or para-central] GA). GA represents the absence of a continuous pigmented layer and the death of at least some portion of RPE cells. Non-central GA spares the fovea and thus preserves central vision. However, patients with non-central GA can experience visual disturbances such as paracentral scotomas, which can impair vision in dim light, decrease contrast sensitivity and impair reading ability. Sub-RPE-BL drusen elevate the RPE off the BrM and thereby can cause mild vision loss, including metamorphopsia (a vision defect in which objects appear to be distorted) through disturbance of overlying photoreceptors and slowing of rod-mediated dark adaptation.

The advanced (late) stage of AMD that remains atrophic AMD is characterized by the presence of drusen and GA that extends to the center of the macula (central GA). Central GA includes macular atrophy. Central GA involves the fovea and thus results in significant loss of central vision and visual acuity. RPE below the retina atrophies, which causes vision loss through the death of photoreceptors. RPE atrophy can result from a large accumulation of drusen and/or BLinD that contributes to the death of the overlying RPE, when the drusen become thick and the RPE is far removed from the choriocapillaris. Drusen may include calcification in the form of hydroxyapatite, and may progress to complete calcification, at which stage RPE cells have died. The RPE-BL thickens in a stereotypic manner to form basal laminar deposits (BLamD); RPE cells hence reside on a thick layer of BLamD. Junctions between the normally hexagonal-shaped RPE cells may be perturbed, and individual RPE cells may round up, stack and migrate anteriorly into the neurosensory retina, where the RPE cells are farther from their supply of nutrients and oxygen in the choriocapillaris. Once RPE cells begin the anterior migration, the overall RPE layer begins to atrophy.

The advanced stage of AMD that becomes neovascular AMD is characterized by neovascularization and any of its potential sequelae, including leakage (e.g., of plasma), plasma lipid and lipoprotein deposition, sub-RPE-BL, subretinal and intraretinal fluid, hemorrhage, fibrin, fibrovascular scars and RPE detachment. In CNV, new blood vessels grow up from the choriocapillaris and through the BrM, which causes vision loss via the aforementioned sequelae. There are three types of neovascularization (NV). Type 1 NV occurs in the sub-RPE-BL space, and new blood vessels emanate from the choroid under the macular region. Type 2 NV occurs in the subretinal space above the RPE, and new blood vessels emanate from the choroid and break through to the subretinal space. In types 1 and 2 NV, new blood vessels cross the BrM and may ramify in the pro-angiogenic cleavage plane created by soft drusen and BLinD. Type 3

NV (retinal angiomatous proliferation) occurs predominantly within the retina (intraretinal), but can also occur in the subretinal space, and new blood vessels emanate from the retina with possible anastomoses to the choroidal circulation. Type 3 NV is the most difficult subtype of NV to diagnose and has the most devastating consequences in terms of photoreceptor damage, but type 3 NV responds well to treatment with an anti-VEGF agent. A neovascular AMD patient can also have a mixture of subtypes of NV, including type 1 plus type 2, type 1 plus type 3, and type 2 plus type 3. The approximate occurrence of the different subtypes of NV among newly presenting neovascular AMD patients is: 40% type 1, 9% type 2, 34% type 3, and 17% mixed (of the mixed, 80% type 1 plus type 2, 16% type 1 plus type 3, and 4% type 2 plus type 3). Another form of NV is polypoidal vasculopathy, which is of choroidal origin and is the most common form of NV among Asians, whose eyes generally have few drusen but may have BLinD. The RPE can become detached from the BrM in each subtype of NV. For instance, leakage of fluid from neovessels into the sub-RPE-BL space in type 1 NV can result in pigment epithelium detachment. The new blood vessels generated by NV are fragile, leading to leakage of fluid, blood and proteins below the macula. Leakage of blood into the subretinal space is particularly toxic to photoreceptors, and intraretinal fluid signifies a poor prognosis for vision. Bleeding and leaking from the new blood vessels, with subsequent fibrosis, can cause irreversible damage to the retina and rapid vision loss if left untreated.

Modified lipids, including peroxidized lipids, can be strongly pro-inflammatory and thus can be pro-angiogenic. Therefore, modification (including oxidation) of lipids can be an important step leading to the development of NV, including type 1 NV. For example, the modified lipids linoleate hydroperoxide and 7-ketocholesterol can be present in and on the BrM and can stimulate NV. NV can be regarded as a wound-healing process following inflammation.

Both eyes of a patient with AMD, whether atrophic or neovascular, typically are in a diseased state. However, one of the eyes typically is in a more diseased condition than the other eye.

For a description of the different stages of AMD, see, e.g., R. Jager et al., *N. Engl. J. Med.*, 358:2606-2617 (2008). The Age-Related Eye Disease Study (AREDS) Research Group has also developed a fundus photographic severity scale for AMD. See, e.g., M. Davis et al., *Arch. Ophthalmol.*, 123: 1484-1498 (2005).

For discussions of the pathogenesis and pathophysiology of AMD, see, e.g., C. A. Curcio et al., The oil spill in ageing Bruch membrane, *Br. J. Ophthalmol.*, 95(12):1638-1645 (2011); J. W. Miller, Age-Related Macular Degeneration Revisited—Piecing the Puzzle, *Am. J. Ophthalmol.*, 155(1): 1-35 (2013); R. Spaide et al., Choroidal neovascularization in age-related macular degeneration—what is the cause?, *Retina*, 23:595-614 (2003); and S. Bressler et al., Age-Related Macular Degeneration: Non-neovascular Early AMD, Intermediate AMD, and Geographic Atrophy, in Retina, S. Ryan et al., Eds., pp. 1150-1182, Elsevier (London 2013).

III. Apolipoprotein Mimetics

As described above, age-related macular degeneration (AMD) is a disease or disorder that has a variety of underlying factors. Three of the major factors of AMD are formation of lipid-rich deposits, inflammation and neovascularization in the retina, the subretinal space, the sub-RPE-BL space and the BrM. Formation of lipid-containing deposits is one of the initial major factors that leads to sequelae such as chronic inflammation, non-central and/or central geographic atrophy (GA) of the retina, neovascularization (including CNV) and ultimately central vision loss or legal blindness. Lipid-scavenging apolipoprotein mimetics, which also possess other beneficial properties such as anti-inflammatory, antioxidant and anti-angiogenic properties, can be used to treat AMD and complications thereof.

Apolipoprotein peptide mimetics can effectively reduce the accumulation of lipid-rich deposits in the eye. Apolipoprotein (apo) mimetics can modulate (e.g., inhibit) the production of lipoproteins (e.g., VLDLs), modulate (e.g., inhibit) cellular uptake of plasma lipids (e.g., cholesterol) and lipoproteins (e.g., VLDLs), mediate the clearance or scavenging of lipids (e.g., cholesterol and oxidized lipids, such as oxysterols) and lipoproteins (e.g., VLDLs) and remnants thereof (e.g., low-density lipoproteins [LDLs] and chylomicron remnants), and inhibit the formation of lipid-containing lesions. For example, apoE mimetics increase lipid (e.g., cholesterol) efflux, mediate the clearance of lipids (e.g., cholesterol) and lipoproteins (e.g., VLDLs and chylomicrons), reduce cholesterol and triglyceride levels, decrease the formation of lipid-containing lesions, and possess antioxidant and anti-inflammatory properties. As another example, apoA-I mimetics promote lipid (e.g., cholesterol) efflux, reduce the formation of lipid-containing lesions (in the eye and arterial intima), and exhibit antioxidant and anti-inflammatory properties. As a further example, apoA-V mimetics decrease VLDL-triglyceride (TG) production and stimulate lipoprotein lipase-mediated lipolysis of VLDL-TG. As an additional example, apoC-II mimetics increase lipid (e.g., cholesterol) efflux and activate lipoprotein lipase-mediated lipolysis of lipoproteins. A beneficial effect of increased lipoprotein lipase-mediated lipolysis of lipoproteins can be, e.g., reduced tissue availability of dietary-derived lipids, which may affect the upstream sources to RPE-derived lipoproteins that are secreted into the BrM, the sub-RPE-BL space and the subretinal space.

As an illustrative example, apoA-I mimetics such as those described herein (e.g., L-4F and D-4F) can dissolve, mobilize and remove accumulated extracellular, and potentially intracellular, lipid deposits in the eye. For instance, L-4F and D-4F may be able to remove intracellular lipids via the LDL-receptor by forming pre-βHDL particles. Lipid deposits on the BrM form a lipid wall that acts as a diffusion barrier between the RPE and the choriocapillaris, promotes the formation of basal linear deposits (BLinD) and soft drusen, and is implicated in local inflammation and oxidative stress. ApoA-I mimetics (e.g., L-4F) can clear lipid deposits from the BrM, thereby remodeling the BrM structure to a normal or healthier state and restoring the BrM function, including reduced hydraulic resistivity and increased metabolite and micronutrient exchange between the choriocapillaris and the RPE, which improves RPE health. In addition, apoA-I mimetics (e.g., L-4F) can facilitate the clearance of lipids, lipoproteins and lipoprotein components via the BrM into the choriocapillaris and systemic circulation and ultimately to the liver for their metabolism and excretion into the bile. Moreover, apoA-I mimetics (e.g., L-4F) can reduce local inflammation and oxidative stress by, e.g., clearing lipid deposits from the BrM, BLinD and soft drusen. Furthermore, apoA-I mimetics (e.g., L-4F) can protect phospholipids from oxidation by, e.g., binding seeding molecules required for formation of pro-inflammatory oxidized phospholipids, such as Ox-PAPC (PAPC is L-α-1-palmitoyl-2-arachidonoyl-sn-glycero-3-phosphocholine), POVPC (1-palmitoyl-2-[5-oxovaleryl]-sn-glycero-3-phosphocholine), PGPC (1-palmitoyl-2-glutaryl-sn-glycero-3-phosphocholine), and PEIPC (1-palmitoyl-2-[5,6-epoxyisoprostane $E_2$]-sn-glycero-3-phosphocholine). ApoA-I mimetics (e.g., L-4F) can also have high affinity for pro-inflammatory oxidized lipids and mediate their removal, adding to the high anti-inflammatory potential of the mimetics. The majority of AMD-associated lipid deposits are extracellular and accessible to lipid-clearing apoA-I mimetics. Therefore, apoA-I mimetics (e.g., L-4F) can be used at any stage of AMD, including from early- to advanced-stage AMD, to treat an important upstream factor of AMD—accumulation of lipid deposits such as BlinD on the BrM and soft drusen in the sub-RPE-BL space—and, through the removal of such deposits, to inhibit or curtail downstream factors of AMD, such as local inflammation and oxidative stress.

In some embodiments, apolipoprotein mimetics include amphipathic helical domains of apolipoproteins which bind to/associate with lipids and are capable of removing/clearing lipids. In certain embodiments, lipid-binding, amphipathic helical domains of apolipoproteins include:

1) sequences from about amino acid (aa) 209 to about aa 219, sequences from about aa 220 to about aa 241, and sequences from about aa 209 to about aa 241 of wild-type (wt) human apoA-I;

2) sequences from about aa 39 or 40 to about aa 50, sequences from about aa 51 to about aa 71 or 77, sequences from about aa 39 or 40 to about aa 71, and sequences from about aa 39 or 40 to about aa 77 of wt human apoA-II;

3) sequences from about aa 7 to about aa 32, sequences from about aa 33 to about aa 53, and sequences from about aa 7 to about aa 53 of wt human apoC-I;

4) sequences from about aa 43 to about aa 55 of wt human apoC-II;

5) sequences from about aa 40 to about aa 67 of wt human apoC-III; and 6) sequences from about aa 203 to about aa 266 of wt human apoE.

In further embodiments, apolipoprotein mimetics include polypeptides (including fusion proteins and chimeras) that comprise such lipid-binding, amphipathic helical domains of apolipoproteins or variants thereof.

Non-limiting examples of apoA-I mimetics include 2F, 3F, 3F-1, 3F-2, 3F-14, 4F (e.g., L-4F and D-4F), 4F2, 5A, 5F, 6F, 7F, 18F, 37 pA, 4F-P-4F, 4F-IHS-4F, ELK-2K2A2E (or ELK-2A2K2E), FAMP (Fukuoka apoA-I mimetic peptide), FREL, KRES, apoJ (113-122), CGVLESFKASFLSALEEWTKKLQ-NH$_2$ (monomer, dimers and trimers) (SEQ. ID. NO. 1), DWLKAFYDKVAEKLKE (monomer, dimers and trimers) (SEQ. ID. NO. 2), DWFKAFYDKVAEKFKE (monomer, dimers and trimers) (SEQ. ID. NO. 3), DWFKAFYDKVAEKFKEAF (4F) (monomer, dimers and trimers) (SEQ. ID. NO. 4), DWLKAFYDKVAEKLKEAFPDWLKAFYDKVAEKLKEAF (SEQ. ID. NO. 5), DWLKAFYDKVAEKLKEFFPDWLKAFYDKVAEKLKEFF (SEQ. ID. NO. 6), DWFKAFYDKVAEKLKEAFPDWFKAFYDKVAEKLKEAF (SEQ. ID. NO. 7), DKLKAFYDKVFEWAKEAFPDKLKAFYDKVFEWLKEAF (SEQ. ID. NO. 8), DKWKAVYDKFAEAFKEFLPDKWKAVYDKFAEAFKEFL (SEQ. ID. NO. 9), DWFKAFYDKVAEKFKEAFPDWFKAFYDKVAEKFKEAF (4F-P-4F) (SEQ. ID. NO. 10), and the corresponding apoA-I mimetics having one or more, or all, D-amino acids (e.g., D-4F having all D-amino acids) and/or the reverse order of amino acid sequence (e.g., Rev-L-4F and Rev-D-4F).

Non-limiting examples of apoE mimetics include Ac-hE18A-NH$_2$ (AEM-28) (a dual-domain [apoE and apoA-I] mimetic), Ac-[R]hE18A-NH$_2$, AEM-28-14, mR18L, ATI-5261, COG-1410, apoE (130-149) monomer and dimers (including N-acetylated dimers), and apoE (141-155) monomer and dimers (including N-acetylated dimers). Examples of apoC-II mimetics include without limitation C-II-a.

The present disclosure encompasses the following apolipoprotein peptide mimetics:

1) apo mimetics in which all of the amino acid residues have the L stereochemistry;

2) apo mimetics in which one or more, or all, of the amino acid residues have the D stereochemistry;

3) apo mimetics which have the reverse order of amino acid sequence and in which all of the amino acid residues have the L stereochemistry;

4) apo mimetics which have the reverse order of amino acid sequence and in which one or more, or all, of the amino acid residues have the D stereochemistry; and 5) multimers (including dimers and trimers) of an apo mimetic, in which two or more units of an apo mimetic are directly or indirectly attached to one another, such as via a linker or spacer group containing one or more amino acid residues or a group having multiple (e.g., two, three or more) points of attachment.

The apolipoprotein mimetics described herein can have a protecting group at the N-terminus and/or the C-terminus. In some embodiments, the apo mimetics have an N-terminal protecting group that is an unsubstituted or substituted $C_2$-$C_{10}$ acyl group (e.g., acetyl, propionyl, butanoyl, pentanoyl or hexanoyl), an unsubstituted or substituted benzoyl group, a carbobenzoxy group, or one or two unsubstituted or substituted $C_1$-$C_{20}$ or $C_2$-$C_{20}$ alkyl groups (e.g., one or two methyl, ethyl, propyl, butyl, pentyl or hexyl groups). Furthermore, the apo mimetics can have a functional group other than —$CO_2H$ at the C-terminus, such as a —C(O)NH$_2$ or —C(O)NR$^1$R$^2$ amide group, wherein R$^1$ and R$^2$ independently are hydrogen, alkyl, cycloalkyl, heterocyclyl, aryl or heteroaryl, or R$^1$ and R$^2$ and the nitrogen atom to which they are connected form a heterocyclic or heteroaryl ring. An amide group at the C-terminus can be regarded as a protecting group at the C-terminus. Therefore, the disclosure encompasses apo mimetics having, e.g., both an acetyl group at the N-terminus and a —C(O)NH$_2$ group at the C-terminus.

The disclosure also encompasses variants of the apolipoprotein mimetics described herein, wherein the variants of the apo mimetics can comprise one or more amino acid additions/insertions, deletions and/or substitutions. In other words, the disclosure encompasses variants in which one or more natural and/or unnatural amino acids are added to or inserted in, one or more amino acid residues are deleted from, or one or more natural and/or unnatural amino acids are substituted (conservative and/or non-conservative substitutions) for one or more amino acid residues of, any of the apo mimetics described herein, or any combination or all thereof. An unnatural amino acid can have the same chemical structure as the counterpart natural amino acid but have the D stereochemistry, or it can have a different chemical structure and the D or L stereochemistry. Unnatural amino acids can be utilized, e.g., to promote α-helix formation and/or increase the stability of the peptide (e.g., resist proteolytic degradation). For example, D-4F is resistant to intestinal peptidases and thus is suitable for oral use. Examples of unnatural amino acids include without limitation proline analogs (e.g., CMePro), phenylalanine analogs

[e.g., Bip, Bip2EtMeO, Nal(1), Nal(2), 2FPhe, Tmp, Tic, CMePhe and CMe2FPhe], tyrosine analogs (e.g., Dmt and CMeTyr), glutamine analogs (e.g., citrulline [Cit]), lysine analogs (e.g, homo-lysine, ornithine [Orn] and CMeLys), arginine analogs (e.g., homo-arginine [Har]), C-α-disubstituted amino acids (e.g., Aib, Ac4c, Ac5c, Ac6c and Deg), and other unnatural amino acids disclosed in US 2015/031630 and WO 2014/081872. One or more peptidomimetic moieties can also be used in additions/insertions and/or substitutions. The variants can have a protecting group at the N-terminus and/or the C-terminus, such as an acyl (e.g., acetyl) group at the N-terminus and/or an amide group [e.g., —C(O)NH$_2$] at the C-terminus. In some embodiments, a biological or pharmacological activity of a variant of an apo mimetic is enhanced relative to, or substantially similar to (e.g., not diminished by more than about 10%, 20% or 30% relative to), that of the apo mimetic with a native amino acid sequence. As a non-limiting example, the disclosure encompasses a variant of 4F called 4F2, which has the sequence DWFKAFYDKV-Aib-EKFKE-Aib-F (SEQ. ID. NO. 11) in which A$^{11}$ and A$^{17}$ are substituted with α-aminoisobutyric acid (Aib). In certain embodiments, 4F2 has the structure Ac-DWFKAFYDKV-Aib-EKFKE-Aib-F—NH$_2$ (SEQ. ID. NO. 12), where all the amino acid residues have the L-form (L-4F2), or one or more, or all, of the amino acid residues have the D-form.

Variants of the apoliprotein mimetics described herein also include analogs and derivatives of the apo mimetics that have another kind of modification alternative to or in addition to an amino acid addition/insertion, deletion and/or substitution. As an example, variants of apo mimetics include fusion proteins and chimeras comprising a lipid-binding, amphipathic helical domain of an apolipoprotein or a variant thereof (e.g., 4F) which is directly or indirectly (e.g., via a linker) attached to a heterologous peptide. The heterologous peptide can impart a beneficial property, such as increased half-life. For instance, the heterologous peptide can be an Fc domain of an immunoglobulin (e.g., an IgG, such as IgG1), or a modified Fc domain of an immunoglobulin which has, e.g., one or more amino acid substitutions or mutations that alter (e.g., reduce) the effector functions of the Fc domain. An Fc domain can be modified to have reduced ability, e.g., to bind to an Fc receptor, activate the complement system, stimulate an attack by phagocytic cells, or interfere with the physiological metabolism or functioning of retinal cells, or any combination or all thereof. Inclusion of an Fc domain in a fusion protein or chimera can permit dimerization of the fusion protein or chimera (e.g., via formation of an intermolecular disulfide bond between two Fc domains), which may enhance the biological or pharmacological activity of the fusion protein or chimera. Alternatively, a longevity-enhancing heterologous peptide can be, e.g., a carboxy-terminal peptide (CTP) derived from the beta chain of human chorionic gonadotropin, such as CTP-001, CTP-002 or CTP-003 as disclosed in WO 2014/159813. As another example, an apo mimetic, such as an apoA-I mimetic (e.g., L-4F) or an apoE mimetic (e.g., AEM-28-14), can be directly or indirectly (e.g., via a linker) attached to a natural or synthetic polymer (e.g., polyethylene glycol [PEG]) at the N-terminus, the C-terminus and/or one or more side chains. PEGylation of an apo mimetic (with, e.g., about 2-20 or 2-10 PEG units) may increase the protease resistance, stability and half-life, reduce the aggregation, increase the solubility and enhance the activity of the apo mimetic. As a further example, an apo mimetic can be glycosylated (comprise a carbohydrate or sugar moiety), such as an apoC-III mimetic containing one or more sialic acid residues. As a still further example, an apo mimetic can be phosphorylated. As an additional example, an apo mimetic can be complexed to a phospholipid (e.g., L-4F complexed to DMPC [1,2-dimyristoyl-sn-glycero-3-phosphocholine] or POPC [1-palmitoyl-2-oleoyl-sn-glycero-3-phosphocholine]).

In addition to or alternative to the use of an apolipoprotein mimetic, an agent that increases the level of an apolipoprotein (e.g., apoE, apoA-I, apoA-V or apoC-II), e.g., by stimulating its production, can be used. For example, an agent that increases the level of apoA-I (e.g., 1,2-dimyristoyl-α-glycero-3-phosphocholine [DMPC]) can be administered in addition to or alternative to the use of an apoA-I mimetic.

Apolipoprotein peptide mimetics, or apolipoprotein mimetic peptides, can be prepared according to procedures known to those of skill in the art. As a non-limiting example, apo mimetics and salts thereof can be prepared by sequentially condensing protected amino acids on a suitable resin support and removing the protecting groups, removing the resin support, and purifying the products by methods known in the art. Solid-phase synthesis of peptides and salts thereof can be facilitated through the use of, e.g., microwave, and can be automated through the use of commercially available peptide synthesizers. Solid-phase synthesis of peptides and salts thereof is described in, e.g., J. M. Palomo, *RSC Adv.*, 4:32658-32672 (2014); M. Amblard et al., *Mol. Biotechnol.*, 33(3):239-254 (2006); and M. Stawikowski and G. B. Fields, *Curr. Protoc. Protein Sci.*, Unit 18.1: Introduction to Peptide Synthesis (2012). Protecting groups suitable for the synthesis of peptides and salts thereof are described in, e.g., P. Wuts and T. Greene, Greene's Protective Groups in Organic Synthesis, 4$^{th}$ Ed., John Wiley and Sons (New York 2006). Methods for purifying peptides and salts thereof include without limitation crystallization, column (e.g., silica gel) chromatography, high-pressure liquid chromatograpy (including reverse-phase HPLC), hydrophobic adsorption chromatography, silica gel adsorption chromatography, partition chromatography, supercritical fluid chromatography, counter-current distribution, ion exchange chromatography, and ion exchange using basic and acidic resins.

IV. Treatment of AMD Using an Apolipoprotein Mimetic

Some embodiments of the disclosure relate to a method of treating age-related macular degeneration (AMD), comprising administering to a subject in need of treatment a therapeutically effective amount of an apolipoprotein (apo) mimetic. In some embodiments, the apo mimetic is administered locally to, into, in or around the eye in a dose from about 0.1 or 0.3 mg to about 1.5 mg per administration (e.g., per injection), or in a total dose from about 0.5 or 1 mg to about 10 mg over a period of about 6 months.

The apo mimetic is used in a substantially pure form. In certain embodiments, the apo mimetic has a purity of at least about 90%, 95%, 96%, 97%, 98% or 99% (e.g., at least about 95% or 98%). The apo mimetic can be purified, that is, substantially free from undesired chemical or biochemical components resulting from its preparation or isolation that are unsuitable for use in a pharmaceutical formulation, or having a level of such undesired chemical or biochemical components sufficiently low so as not to prevent use of the apo mimetic in a pharmaceutical formulation.

Non-limiting examples of apolipoprotein mimetics, including apoA-I mimetics and apoE mimetics, include those described elsewhere herein. In some embodiments, the apo mimetic includes, or is, an apoE mimetic. In certain embodiments, the apoE mimetic includes, or is, AEM-28-14 or a variant or salt thereof.

In further embodiments, the apo mimetic includes, or is, an apoA-I mimetic alternative to or in addition to an apoE mimetic (e.g., AEM-28-14). In certain embodiments, the apoA-I mimetic includes, or is, 4F or a variant or salt (e.g., acetate salt) thereof. In some embodiments, all the amino acid residues of 4F have the L stereochemistry (L-4F). In other embodiments, one or more, or all, of the amino acid residues of 4F have the D stereochemistry (e.g., D-4F having all D-amino acids). In yet other embodiments, the apo mimetic has the reverse order of amino acid sequence of 4F (e.g., Rev-L-4F or Rev-D-4F). The apo mimetic can have a protecting group at the N-terminus and/or the C-terminus, such as an acyl (e.g., acetyl) group at the N-terminus and/or an amide group (e.g., —C(O)NH$_2$) at the C-terminus. In certain embodiments, the apo mimetic includes, or is, L-4F having the structure Ac-DWFKAFYDKVAEKFKEAF-NH$_2$ (SEQ. ID. NO. 13). When folded into the appropriate secondary structure, L-4F is an amphipathic α-helix that has opposing polar and hydrophobic faces and mimics apoA-I, the predominant apolipoprotein of HDL.

The apoA-I mimetic 4F, including L-4F and D-4F, possesses anti-dyslipidemic properties. For example, L-4F is capable of binding both oxidized lipids and unoxidized lipids with a greater affinity than apoA-I itself and reduces lipid deposits, e.g., in the sub-RPE-BL space and on the Bruch's membrane (BrM). L-4F is a potent lipid acceptor and scavenger that removes extracellular lipids (and potentially intracellular lipids), including neutral lipids, esterified cholesterol and phospholipids, from, e.g., the BrM and the sub-RPE-BL space, thereby improving, e.g., the BrM structure (e.g., reducing the thickness and normalizing the layer arrangement of the BrM) and the BrM function (e.g., decreasing hydraulic resistivity of the BrM and increasing metabolite and micronutrient exchange between the RPE and the choriocapillaris, including facilitating multimolecular complexes carrying such nutrients). Extracellular age-related lipid deposits at, e.g., the BrM form a hydrophobic diffusion barrier that causes oxidative stress and inflammation in, e.g., the RPE and the retina, and removal of such lipid deposits by L-4F curtails such oxidative stress and inflammation.

L-4F possesses additional beneficial properties. For instance, L-4F exhibits a strong anti-inflammatory property, due in part to its high-affinity binding to pro-inflammatory oxidized lipids (e.g., oxidized phospholipids) and fatty acid hydroperoxides and its clearance of such oxidized lipids. L-4F can also enhance the ability of HDL-cholesterol to protect LDL-cholesterol from oxidation, thereby curtailing the formation of pro-inflammatory oxidized lipids. Furthermore, L-4F inhibits complement activation and reduces the levels of complement factor D and the membrane attack complex, which can be additional reasons for its antioxidant and anti-inflammatory properties and can result from its inhibition of downstream effects of lipid deposition. In addition, L-4F has anti-angiogenic property. Extracellular lipid-rich deposits in the sub-RPE-BL space provide a biomechanically fragile, pro-inflammatory milieu into which new blood vessels can enter and propagate, unimpeded by RPE basal lamina connections to the rest of the BrM. Removal of such lipid deposits by L-4F can close up or substantially reduce this pro-angiogenic cleavage plane.

In a study conducted on a macaque model of human early AMD and described below, L-4F demonstrated an effective ability to scavenge neutral lipids and esterified cholesterol, to rejuvenate/normalize the BrM, and to curtail downstream effects of lipid deposition such as complement activation and local inflammation. L-4F also appeared to effectively scavenge phospholipids, a major source of pro-inflammatory oxidized lipids, although staining for phospholipids was not done in the study. The results of the macaque study are expected to be translatable to all stages and forms of AMD in humans in which extracellular lipid deposits play a pathological role, including early AMD, intermediate AMD and advanced AMD, and including atrophic AMD and neovascular AMD. Drusen are rich in esterified cholesterol and phospholipids, attributed to the core and the surface, respectively, of RPE-secreted lipoproteins. Furthermore, because lipoproteins (both native and modified) in drusen are not bound to structural collagen and elastin fibrils, unlike lipoproteins in the BrM, the former are more loosely bound than the latter and hence are easier to remove. Therefore, the great reduction of esterified cholesterol and lipid deposits from the BrM in the macaque study demonstrates the ability of L-4F to effectively reduce soft drusen and scavenge lipids, including esterified cholesterol, from eye tissues, including the BrM. Although the RPE has active proteases, intravitreally injected L-4F readily crossed the RPE and reached the BrM, and effectively removed lipid deposits from the BrM in the macaque study. Removal of lipid deposits from the BrM by L-4F normalizes the structure and function of the BrM. In addition, reduction of drusen volume by L-4F can decrease elevation of the RPE layer off the BrM and thereby can reduce metamorphopsia, and can prevent, delay the onset of or slow the progression of non-central or central geographic atrophy and thereby can improve vision. Reduction of drusen volume in humans can be readily quantified using spectral domain optical coherence tomography (SDOCT) and commercially available software.

By reducing lipid deposits, L-4F can maintain or improve the health of the RPE and thereby can prevent or forestall RPE atrophy, including in non-central and central geographic atrophy. Soft drusen and drusenoid pigment epithelial detachments (PED) grow over time because RPE cells continue to secrete lipoproteins. The RPE layer over the drusen and drusenoid PED roughens over time, and RPE cells migrate out of the RPE layer and anteriorly into the neurosensory retina, preferentially over the apices, where the RPE cells are farther from the choriocapillaris and thus seek oxygen from the retinal circulation. By removing native and modified lipids from drusen, L-4F can prevent the anterior migration of RPE cells and thereby can keep RPE cells sufficiently close to the choriocapillaris so that RPE cells are not energetically and metabolically decompensated and hence do not atrophy. Furthermore, removal of lipid deposits from the BrM improves the transport of incoming micronutrients (including vitamin A) and outgoing waste between the choriocapillaris and the RPE. By reducing drusen and removing lipid deposits from the BrM, L-4F can maintain RPE health and forestall RPE atrophy, and thereby can preserve photoreceptors and vision. Health of the RPE overlying drusen can be monitored by SDOCT of the macula.

Reduction of lipid deposits had downstream benefits in the macaque study, including a great decrease in the number of membrane attack complexes (MAC) present in the BrM and the choriocapillaris. The MAC (C5b-9) is the final product of activation of the complement system, and builds up in the BrM-choriocapillaris complex during a person's lifespan, starting in childhood. By decreasing the level of MAC, L-4F can improve the health of the BrM and the choriocapillaris endothelium, and thereby can improve the blood supply to the outer retina and micronutrient exchange between the choriocapillaris and the RPE and can promote the clearing of lipoprotein particles secreted by the RPE into the systemic circulation.

In addition, by removing lipids L-4F can prevent or forestall neovascularization (NV). Basal linear deposits and soft drusen are major sources of potentially pro-inflammatory lipids in the sub-RPE-BL space where type 1 NV, the most common type of NV, occurs. Removal of native lipids, including esterified cholesterol in lipoprotein deposits, from eye tissues by L-4F, as demonstrated in the macaque study, reduces the amount of native lipids available for modifications such as peroxidation. Modified lipids, including peroxidized lipids, can be strongly pro-inflammatory and thus can stimulate NV. L-4F can also scavenge any peroxidized lipids and other modified lipids formed. Furthermore, by reducing the bulk size of drusen, L-4F can prevent the migration of RPE cells away from the nutrient-transporting choriocapillaris and hence their secretion of distress-induced VEGF, a potent stimulus of NV. Moreover, normalization of the BrM as a result of removal of lipid deposits from the BrM by L-4F suppresses choroidal NV by reinforcing the natural barrier between the choriocapillaris and the sub-RPE-BL space. Therefore, through its ability to scavenge native lipids and modified (e.g., oxidized) lipids, L-4F can prevent or curtail NV, including type 1 NV, and can improve the treatment of neovascular AMD, and reduce the treatment burden, with anti-angiogenic agents, including intravitreally injected anti-VEGF agents.

In some embodiments, the apo mimetic [e.g., an apoA-I mimetic (e.g., L-4F) and/or an apoE mimetic (e.g., AEM-28-14)] is administered locally in a dose of about 0.1-0.5 mg, 0.5-1 mg or 1-1.5 mg per administration (e.g., per injection). In further embodiments, the apo mimetic [e.g., an apoA-I mimetic (e.g., L-4F) and/or an apoE mimetic (e.g., AEM-28-14)] is administered locally in a dose of about 0.1-0.3 mg, 0.3-0.5 mg, 0.5-0.75 mg, 0.75-1 mg, 1-1.25 mg or 1.25-1.5 mg per administration (e.g., per injection). The apo mimetic can also be administered locally in a dose greater than 1.5 mg per administration (e.g., per injection), such as up to about 2 mg or more per administration (e.g., per injection). In certain embodiments, the apo mimetic [e.g., an apoA-I mimetic (e.g., L-4F) and/or an apoE mimetic (e.g., AEM-28-14)] is administered locally in a dose of about 0.1-0.5 mg or 0.5-1 mg per administration (e.g., per injection).

In further embodiments, the apo mimetic [e.g., an apoA-I mimetic (e.g., L-4F) and/or an apoE mimetic (e.g., AEM-28-14)] is administered locally in a total or cumulative dose of about 0.5 or 1-5 mg or 5-10 mg over a period of about 6 months. In some embodiments, the apo mimetic [e.g., an apoA-I mimetic (e.g., L-4F) and/or an apoE mimetic (e.g., AEM-28-14)] is administered locally in a total or cumulative dose of about 0.5 or 1-3 mg, 3-5 mg, 5-7.5 mg or 7.5-10 mg over a period of about 6 months. The apo mimetic can also be administered locally in a total or cumulative dose greater than 10 mg over a period of about 6 months, such as up to about 15 mg or more over a period of about 6 months. In certain embodiments, the apo mimetic [e.g., an apoA-I mimetic (e.g., L-4F) and/or an apoE mimetic (e.g., AEM-28-14)] is administered locally in a total or cumulative dose of about 0.5-3 mg or 3-5 mg over a period of about 6 months.

In still further embodiments, the apo mimetic [e.g., an apoA-I mimetic (e.g., L-4F) and/or an apoE mimetic (e.g., AEM-28-14)] is administered locally in a total or cumulative dose of about 1 or 2-20 mg or 5-15 mg for the whole or entire treatment regimen. In certain embodiments, the apo mimetic [e.g., an apoA-I mimetic (e.g., L-4F) and/or an apoE mimetic (e.g., AEM-28-14)] is administered locally in a total or cumulative dose of about 1-5 mg, 5-10 mg, 10-15 mg or 15-20 mg for the entire treatment regimen. In some embodiments, the apo mimetic [e.g., an apoA-I mimetic (e.g., L-4F) and/or an apoE mimetic (e.g., AEM-28-14)] is administered locally in a total or cumulative dose of about 1-3 mg, 3-5 mg, 5-7.5 mg, 7.5-10 mg, 10-12.5 mg, 12.5-15 mg, 15-17.5 mg or 17.5-20 mg for the entire treatment regimen. The apo mimetic can also be administered locally in a total or cumulative dose greater than 20 mg for the entire treatment regimen, such as up to about 25 mg, 30 mg, 40 mg, 50 mg or more for the entire treatment regimen. In certain embodiments, the apo mimetic [e.g., an apoA-I mimetic (e.g., L-4F) and/or an apoE mimetic (e.g., AEM-28-14)] is administered locally in a total or cumulative dose of about 1-5 mg or 5-10 mg for the entire treatment regimen.

In some embodiments, the apo mimetic [e.g., an apoA-I mimetic (e.g., L-4F) and/or an apoE mimetic (e.g., AEM-28-14)] is administered locally to, into, in or around the eye. In some embodiments, the apo mimetic [e.g., an apoA-I mimetic (e.g., L-4F) and/or an apoE mimetic (e.g., AEM-28-14)] is administered by injection (e.g., intravitreal, subconjunctival, subretinal or sub-Tenon's injection), eye drop or implant (e.g., intravitreal, intraaqueous, subretinal or sub-Tenon's implant). In certain embodiments, the apo mimetic [e.g., an apoA-I mimetic (e.g., L-4F) and/or an apoE mimetic (e.g., AEM-28-14)] is administered by injection (e.g., intravitreal, subconjunctival, subretinal or sub-Tenon's injection). An intravitreally injected apo mimetic can readily reach target sites such as the sub-RPE-BL space and the BrM from the vitreous cavity. In doing so, the apo mimetic can be distributed in different tissue layers of the eye, such as the neurosensory retina, the BrM and the choroid. The apo mimetic can have a long duration of action (e.g., at least about 2, 3 or 4 weeks or longer) through, e.g., a continuous and slow re-supply or "washout" from the various tissue layers between the inner and outer retinal layers in which the apo mimetic can be distributed. In further embodiments, the apo mimetic [e.g., an apoA-I mimetic (e.g., L-4F) and/or an apoE mimetic (e.g., AEM-28-14)] is administered by eye drop. In additional embodiments, the apo mimetic [e.g., an apoA-I mimetic (e.g., L-4F) and/or an apoE mimetic (e.g., AEM-28-14)] is administered by implanting in or injecting into, e.g., the vitreal chamber, the space below the retina or the aqueous humor devices or materials that deliver the apo mimetic in a controlled and/or sustained manner, such as microdevices, bioabsorbable polymeric materials, or bioabsorbable microparticles or nanoparticles. In other embodiments, the apo mimetic [e.g., an apoA-I mimetic (e.g., L-4F) and/or an apoE mimetic (e.g., AEM-28-14)] is administered by injection or implantation in the eye of genetically engineered cells (e.g., RPE cells containing an expression vector that includes a gene encoding the apo mimetic) or a viral (e.g., adenoviral or lentiviral) vector containing a gene or expression construct (e.g., a plasmid) that expresses the apo mimetic. Such a delivery method would have the benefit of requiring only a one-time injection or implant of the apo mimetic-encoding expression construct in the eye. If two or more apo mimetics [e.g., an apoA-I mimetic (e.g., L-4F) and an apoE mimetic (e.g., AEM-28-14)] are utilized, the same expression construct or different expression constructs can express the two or more apo mimetics.

In embodiments where the apo mimetic [e.g., an apoA-I mimetic (e.g., L-4F) and/or an apoE mimetic (e.g., AEM- 28-14)] is administered locally to, into, in or around the eye, the dose per administration, the total dose over a period of about 6 months, and the total dose for the whole treatment regimen are per administered eye in certain embodiments and for both eyes in other embodiments. The blood system may allow some amount (e.g., a therapeutically effective amount) of the apo mimetic locally administered (e.g., injected) into or in one eye to be distributed to the other eye, in which case the dose of the apo mimetic can optionally be adjusted (e.g., increased) to take into account the other eye (which may be in a less diseased condition), and which may allow both eyes to be treated with the apo mimetic at the same time without an additional administration (e.g., injection) of the apo mimetic into or in the other eye. For example, an intravitreally injected apo mimetic can move with the natural fluid flow from the vitreous humor toward the choroid via the retina and the RPE and cross the blood-retinal barrier (maintained by the retinal vascular endothelium and the RPE) to reach two of the target areas, the sub-RPE-BL space and the Bruch's membrane, from where the apo mimetic may enter the choriocapillaris and ultimately the fellow non-administered eye. Also without intending to be bound by theory, some amount of the apo mimetic may enter the fellow non-administered eye by way of the aqueous humor, which drains via the trabecular meshwork and Schlemm's canal that flows into the blood system. Accordingly, some embodiments relate to a method of treating AMD, comprising administering to a subject in need of treatment a therapeutically effective amount of an apo mimetic, wherein the apo mimetic is administered locally to, into, in or around one eye and has a therapeutic effect in both eyes.

In certain embodiments, the apo mimetic [e.g., an apoA-I mimetic (e.g., L-4F) and/or an apoE mimetic (e.g., AEM-28-14)] is administered locally to, into, in or around the eye in the early phase of treatment, and then the apo mimetic is administered systemically. As a non-limiting example, the initial administration(s) (e.g., the first one to five administrations) of the apo mimetic can be local via injection (e.g., intravitreal, subconjunctival, subretinal or sub-Tenon's injection), and then subsequent administration(s) of the apo mimetic can be systemic, such as oral, parenteral (e.g., subcutaneous, intramuscular or intravenous), or topical (e.g., intranasal or pulmonary). In other embodiments, the apo mimetic is administered only locally (e.g., via injection, eye drop or an implant). In yet other embodiments, the apo mimetic is administered only systemically.

In some embodiments, the apo mimetic [e.g., an apoA-I mimetic (e.g., L-4F) and/or an apoE mimetic (e.g., AEM-28-14)] is administered, whether locally (e.g., by intravitreal injection) or systemically, in a dose concentration from about 1, 2, 3, 4 or 5 mg/mL to about 12 or 15 mg/mL. If two or more apo mimetics (e.g., an apoA-I mimetic and an apoE mimetic) are used, they can be administered in the same formulation or in different formulations. In certain embodiments, the apo mimetic [e.g., an apoA-I mimetic (e.g., L-4F) and/or an apoE mimetic (e.g., AEM-28-14)] is administered (e.g., by intravitreal injection) in a dose concentration of about 1-4 mg/mL, 4-8 mg/mL, 8-12 mg/mL, 1-5 mg/mL, 5-10 mg/mL or 10-15 mg/mL. In some embodiments, the apo mimetic [e.g., an apoA-I mimetic (e.g., L-4F) and/or an apoE mimetic (e.g., AEM-28-14)] is administered (e.g., by intravitreal injection) in a dose concentration of about 1-3 mg/mL, 3-5 mg/mL, 5-7.5 mg/mL, 6-8 mg/mL, 7.5-10 mg/mL, 10-12.5 mg/mL or 12.5-15 mg/mL. The apo mimetic can also be administered, whether locally (e.g., by intravitreal injection) or systemically, in a dose concentration greater than 15 mg/mL, such as up to about 20 mg/mL or more. In certain embodiments, the apo mimetic [e.g., an apoA-I mimetic (e.g., L-4F) and/or an apoE mimetic (e.g., AEM-28-14)] is administered (e.g., by intravitreal injection) in a dose concentration of about 1-5 mg/mL, 5-10 mg/mL or 6-8 mg/mL.

In further embodiments, the apo mimetic [e.g., an apoA-I mimetic (e.g., L-4F) and/or an apoE mimetic (e.g., AEM-28-14)] is administered locally (e.g., by intravitreal injection) in a dose volume of about 50-150 µL or 50-100 µL. In certain embodiments, the apo mimetic [e.g., an apoA-I mimetic (e.g., L-4F) and/or an apoE mimetic (e.g., AEM-28-14)] is administered locally (e.g., by intravitreal injection) in a dose volume of about 50-75 µL, 75-100 µL, 100-125 µL or 125-150 µL. In some embodiments, the apo mimetic [e.g., an apoA-I mimetic (e.g., L-4F) and/or an apoE mimetic (e.g., AEM-28-14)] is administered locally (e.g., by intravitreal injection) in a dose volume of about 50 µL, 75 µL, 100 µL, 125 µL or 150 µL. The apo mimetic may also be administered locally (e.g., by injection to, into, in or around the eye) in a dose volume greater than 150 µL, such as up to about 200 µL, as long as the administered volume does not significantly increase intraocular pressure. In certain embodiments, the apo mimetic [e.g., an apoA-I mimetic (e.g., L-4F) and/or an apoE mimetic (e.g., AEM-28-14)] is administered locally (e.g., by intravitreal injection) in a dose volume of about 100 µL (0.1 mL).

In additional embodiments, the apo mimetic [e.g., an apoA-I mimetic (e.g., L-4F) and/or an apoE mimetic (e.g., AEM-28-14)] is administered locally (e.g., by intravitreal injection) once every month (4 weeks) or 1.5 months (6 weeks). In other embodiments, the apo mimetic [e.g., an apoA-I mimetic (e.g., L-4F) and/or an apoE mimetic (e.g., AEM-28-14)] is administered locally (e.g., by intravitreal injection) once every 2 months (8 weeks), 2.5 months (10 weeks) or 3 months (12 weeks). In yet other embodiments, the apo mimetic [e.g., an apoA-I mimetic (e.g., L-4F) and/or an apoE mimetic (e.g., AEM-28-14)] is administered locally (e.g., by intravitreal injection or an intravitreal implant) once every 4, 5 or 6 months. In some embodiments, the apo mimetic [e.g., an apoA-I mimetic (e.g., L-4F) and/or an apoE mimetic (e.g., AEM-28-14)] is administered locally (e.g., by intravitreal injection) more frequently and/or in a higher dose in the early phase of treatment.

In further embodiments, the apo mimetic [e.g., an apoA-I mimetic (e.g., L-4F) and/or an apoE mimetic (e.g., AEM-28-14)] is administered locally in a total of about 15 or less, 12 or less, 9 or less, 6 or less, or 3 or less administrations (e.g., intravitreal injections). In certain embodiments, the apo mimetic [e.g., an apoA-I mimetic (e.g., L-4F) and/or an apoE mimetic (e.g., AEM-28-14)] is administered locally in a total of about 3-6, 6-9, 9-12 or 12-15 administrations (e.g., intravitreal injections). The apo mimetic can also be administered locally in a total of more than 15 administrations (e.g., intravitreal injections), such as up to about 20 or more administrations (e.g., intravitreal injections). In some embodiments, the apo mimetic [e.g., an apoA-I mimetic (e.g., L-4F) and/or an apoE mimetic (e.g., AEM-28-14)] is administered locally in a total of about 15, 14, 13, 12, 11 or 10 administrations (e.g., intravitreal injections). In other embodiments, the apo mimetic [e.g., an apoA-I mimetic (e.g., L-4F) and/or an apoE mimetic (e.g., AEM-28-14)] is administered locally in a total of about 9, 8, 7, 6, 5, 4 or 3 administrations (e.g., intravitreal injections). In certain embodiments, the apo mimetic [e.g., an apoA-I mimetic (e.g., L-4F) and/or an apoE mimetic (e.g., AEM-28-14)] is administered locally in a total of about 3-6 or 7-10 administrations (e.g., intravitreal injections). In embodiments where the apo mimetic is administered locally to, into, in or around the eye, the frequency of administration and the total number of administrations (e.g., injections) are per administered eye in certain embodiments and for both eyes in other embodiments, as the apo mimetic may also have a therapeutic effect in the fellow non-administered eye.

As with dosage per administration, total dosage over a period of about 6 months, total dosage for the entire treatment regimen, dosing frequency and total number of administrations, the duration/length of treatment with the apolipoprotein mimetic can be adjusted if desired and can be selected by the treating physician to minimize treatment burden and to achieve desired outcome(s), such as reduction of lipid deposits to a desired level (e.g., the presence of a few medium-size drusen or the absence of any large druse) and elimination or reduction of geographic atrophy (non-central or central) to a desired level. In some embodiments, the treatment regimen with the apo mimetic [e.g., an apoA-I mimetic (e.g., L-4F) and/or an apoE mimetic (e.g., AEM-28-14)] lasts for about 24 months or less, 18 months or less, 12 months or less, or 6 months or less. In further embodiments, the treatment regimen with the apo mimetic [e.g., an apoA-I mimetic (e.g., L-4F) and/or an apoE mimetic (e.g., AEM-28-14)] lasts for about 18-24 months, 12-18 months or 6-12 months. Treatment with the apo mimetic can also last longer than 24 months (2 years), such as up to about 2.5 years, 3 years, 3.5 years, 4 years or longer. In some embodiments, the treatment regimen with the apo mimetic [e.g., an apoA-I mimetic (e.g., L-4F) and/or an apoE mimetic (e.g., AEM-28-14)] lasts for about 24, 21, 18, 15, 12, 9 or 6 months. In certain embodiments, the treatment regimen with the apo mimetic [e.g., an apoA-I mimetic (e.g., L-4F) and/or an apoE mimetic (e.g., AEM-28-14)] lasts for about 6-12 or 12-24 months.

In some embodiments, the apo mimetic [e.g., an apoA-I mimetic (e.g., L-4F) and/or an apoE mimetic (e.g., AEM-28-14)] is administered at least in the advanced (late) stage of AMD. In certain embodiments, the apo mimetic [e.g., an apoA-I mimetic (e.g., L-4F) and/or an apoE mimetic (e.g., AEM-28-14)] is administered at least in the advanced stage of AMD to treat or slow the progression of central geographic atrophy (GA), and/or to prevent or delay the onset of neovascular AMD. In further embodiments, the apo mimetic [e.g., an apoA-I mimetic (e.g., L-4F) and/or an apoE mimetic (e.g., AEM-28-14)] is administered at least in the advanced stage of AMD to treat or slow the progression of neovascular AMD.

In additional embodiments, the apo mimetic [e.g., an apoA-I mimetic (e.g., L-4F) and/or an apoE mimetic (e.g., AEM-28-14)] is administered at least in the intermediate stage of AMD. In certain embodiments, the apo mimetic [e.g., an apoA-I mimetic (e.g., L-4F) and/or an apoE mimetic (e.g., AEM-28-14)] is administered at least in the intermediate stage of AMD to treat or slow the progression of non-central GA, and/or to prevent or delay the onset of central GA and/or neovascular AMD. In further embodiments, the apo mimetic [e.g., an apoA-I mimetic (e.g., L-4F) and/or an apoE mimetic (e.g., AEM-28-14)] is administered at least in the early phase of intermediate AMD to prevent or delay the onset of non-central GA. Intermediate AMD is characterized by a substantial amount of confluent soft drusen, which can mainly comprise esterified cholesterol and phospholipids. Reduction of confluent soft drusen in intermediate AMD using the apo mimetic [e.g., an apoA-I mimetic (e.g., L-4F) and/or an apoE mimetic (e.g., AEM-28-14)] can result in decrease in the thickness ("thinning") and normalization of the Bruch's membrane, as well as renewal of the overlying RPE cell layer due to improved exchange of micronutrients and metabolites between the choriocapillaris and the RPE. Reduction of confluent soft drusen can be observed by non-invasive techniques such as spectral domain optical coherence tomography (SDOCT).

In further embodiments, the apo mimetic [e.g., an apoA-I mimetic (e.g., L-4F) and/or an apoE mimetic (e.g., AEM-28-14)] is administered at least in the early stage of AMD. The apo mimetic can be administered at an earlier stage (e.g., the early stage or the intermediate stage) of AMD to slow or stop the progression of AMD. In some embodiments, the apo mimetic [e.g., an apoA-I mimetic (e.g., L-4F) and/or an apoE mimetic (e.g., AEM-28-14)] is administered at least in the early stage of AMD to prevent or delay the onset of non-central GA. In certain embodiments, the apo mimetic is administered locally to, into, in or around the eye (e.g., by intravitreal, subconjunctival, subretinal or sub-Tenon's injection or eye drop) in the early stage of AMD. If the apo mimetic [e.g., an apoA-I mimetic (e.g., L-4F) and/or an apoE mimetic (e.g., AEM-28-14)] is administered locally in an invasive manner (e.g., by intravitreal, subconjunctival, subretinal or sub-Tenon's injection), the apo mimetic can be administered less frequently (e.g., an injection every about 3, 4 or 6 months), in a smaller total number of administrations (e.g., about 1, 2 or 3 injections) or in a higher dose per administration (e.g., about 0.5-1 mg or 1-1.5 mg per injection), or any combination or all thereof, to minimize the treatment burden. The apo mimetic does not need to eliminate or remove all or most of the abnormal lipid deposits from the eye to have a therapeutic or prophylactic effect in AMD. If a threshold amount of abnormal lipids is cleared from the eye, natural transport mechanisms, including traffic between the choriocapillaris endothelium and the RPE layer, can properly work again and can clear remaining abnormal lipids from the eye. Furthermore, lipids accumulate in the eye slowly over a period of years (although fluctuations in druse volume in a shorter time frame are detectable). Therefore, less frequent administration (e.g., an intravitreal injection every about 3, 4 or 6 months) and/or a smaller total number of administrations (e.g., about 1, 2 or 3 intravitreal injections) of the apo mimetic can still have a therapeutic or prophylactic effect in early AMD.

In other embodiments, the apo mimetic [e.g., an apoA-I mimetic (e.g., D-4F) and/or an apoE mimetic (e.g., AEM-28-14)] is administered systemically (e.g., orally or parenterally, such as intravenously) in the early stage of AMD. To increase the resistance of an apo mimetic peptide to peptidases/proteases, a variant of the apo mimetic containing one or more, or all, D-amino acids (e.g., D-4F having all D-amino acid residues) can be administered systemically (or by eye drop, because the ocular surface contains peptidases/proteases). The dose of the apo mimetic for systemic administration can be much higher than its dose for local administration (e.g., by intravitreal injection or eye drop) to take into account its systemic distribution and its potential systemic anti-dyslipidemic effects, such as reduction or removal of atherosclerotic plaques in the systemic vasculature, which may be a major target (and thus a sink) for the apo mimetic in systemic circulation. In certain embodiments, the dose of the apo mimetic [e.g., an apoA-I mimetic (e.g., D-4F) and/or an apoE mimetic (e.g., AEM-28-14)] for systemic administration is at least about 50, 100, 200, 300, 400, 500 or 1,000 times (e.g., at least about 100 or 500 times) greater than its dose for local administration. In some embodiments, the dose of the apo mimetic [e.g., an apoA-I mimetic (e.g., D-4F) and/or an apoE mimetic (e.g., AEM- 28-14)] for systemic administration amounts to at least about 50 mg, 100 mg, 200 mg, 300 mg, 400 mg or 500 mg per day (e.g., amounts to at least about 50 mg or 100 mg per day if administered intravenously or amounts to at least about 200 or 300 mg per day if administered orally). In further embodiments, the apo mimetic is administered, whether systemically (e.g., orally or parenterally, such as intravenously) or locally into the eye in a non-invasive manner (e.g., by eye drop), one, two or more times daily, once every two days, once every three days, once a week, once every two weeks or once a month (e.g., once daily or once every two days) in the early stage of AMD for a length of time selected by the treating physician (e.g., at least about 3 months, 6 months, 12 months, 18 months, 24 months or longer) or until the disease has been successfully treated according to selected outcome measure(s) (e.g., elimination of all or most soft drusen or reduction of soft drusen volume to a certain level).

In certain embodiments, the apo mimetic [e.g., an apoA-I mimetic (e.g., L-4F) and/or an apoE mimetic (e.g., AEM-28-14)] is administered (e.g., by intravitreal injection) less frequently, and/or in a lower dose, the earlier the stage of AMD. A higher dose of the apo mimetic can also be administered the earlier the stage of AMD. Phrased another way, in certain embodiments, the apo mimetic [e.g., an apoA-I mimetic (e.g., L-4F) and/or an apoE mimetic (e.g., AEM-28-14)] is administered (e.g., by intravitreal injection) more frequently (which can result in a greater total number of administrations), and/or in a higher dose (higher dose per administration and/or higher total dose for the entire treatment regimen), the later the stage of AMD or the more severe the AMD condition. As a non-limiting example, in intermediate AMD and advanced AMD (including atrophic AMD and neovascular AMD), the apo mimetic can be administered by injection (e.g., intravitreal, subconjunctival, subretinal or sub-Tenon's injection) more frequently (e.g., once every about 4-12 or 4-8 weeks in intermediate AMD, and once every about 4-8 or 4-6 weeks in advanced AMD), in a greater total number of injections (e.g., about 4-8 injections or more in intermediate AMD, and about 8-12 injections or more in advanced AMD), in a higher dose per injection (e.g., up to about 1-1.5 mg per injection), or in a larger total dose for the entire treatment regimen (e.g., up to about 10-15 mg or more in intermediate AMD, and up to about 15-20 mg or more in advanced AMD), or any combination or all thereof, to remove a greater amount of lipid deposits, including drusen and basal linear deposits, from the eye, including from the sub-RPE-BL space and the Bruch's membrane.

In the early, intermediate and advanced stages of AMD, and in atrophic AMD and neovascular AMD, the progression and treatment of AMD can be monitored using various methods known in the art (called "diagnostic" methods herein for simplicity). Such methods include without limitation structural SDOCT (which reveals drusen and RPE and can quantify total drusen volume and monitor progression of the disease), hyperspectral autofluorescence (which can detect fluorophores unique to drusen and basal linear deposits), color fundus photography, quantitative fundus autofluorescence (qAF) and OCT-fluorescein angiography (FA), and can examine parameters such as cone-mediated vision (e.g., best-corrected visual acuity [BCVA, which persists until late in the disease], visual acuity with an ETDRS chart, contrast sensitivity with a Pelli-Robson chart, low-luminance visual acuity [visual acuity measured with a neutral-density filter to reduce retinal illuminance], and development of metamorphopsia) and rod-mediated vision (e.g., dark adaptation kinetics [which is a sensitive measure of macular function that tracks with progression of the disease]). For example, treatment is expected to keep stable, or to improve, photopic (daylight) vision mediated by cone photoreceptors and scotopic (night) vision mediated by rod photoreceptors. As another example, the health of RPE cells can be assessed with qAF, where stability of or increase in qAF intensity can indicate stable or improved RPE health, as a reduction in qAF intensity can signify degeneration of RPE cells. qAF can be used to quantify the area or size of geographic atrophy, and hence to monitor the progression of non-central GA or central GA, as was done in the MAHALO Phase II study on lampalizumab. The health of RPE cells can also be assessed with SDOCT, where the presence of hyper-reflective foci located vertically above drusen within the retina indicates migratory RPE cells, which signifies that the RPE layer is about to disintegrate just before atrophy of RPE cells and photoreceptors. Poor RPE health can be an indicator of poor visual outcome in atrophic AMD and neovascular AMD. As a further example, OCT-FA can detect the presence of sub-RPE-BL, subretinal or intraretinal fluid, which can signify active neovascularization and leakage of fluid from new blood vessels.

Employment of diagnostic methods allows the course of treatment of early, intermediate or advanced AMD, or atrophic AMD or neovascular AMD, using one or more therapeutic agents (e.g., an apo mimetic, an anti-angiogenic agent or a complement inhibitor, or any combination or all thereof), to be monitored and adjusted. As an example, an apo mimetic [e.g., an apoA-I mimetic (e.g., L-4F) and/or an apoE mimetic (e.g., AEM-28-14)] can be administered by injection (e.g., intravitreal, subconjunctival, subretinal or sub-Tenon's injection) for the treatment of early, intermediate or advanced AMD, or atrophic AMD or neovascular AMD. During the initial phase of treatment, the apo mimetic can be administered in a certain frequency of injections and in a certain dose per injection. If one or more diagnostic methods show substantial improvement in the disease, or stability in the disease after a significant length of treatment (e.g., SDOCT shows substantial reduction of soft drusen volume, or stability in soft drusen volume after a significant length of treatment), the apo mimetic can be injected less frequently and/or in a lower dose per injection, or the apo mimetic can be injected less frequently and in a higher dose per injection so that a substantially similar total dose is administered over a certain time period. On the other hand, if one or more diagnostic methods show a worsening of the disease, or no change in the disease (particularly in a more severe form of the disease, such as non-central or central geographic atrophy or neovascular AMD) after the initial phase of treatment (e.g., SDOCT shows an increase in soft drusen volume, or no change in soft drusen volume after the initial phase of treatment), the apo mimetic can be injected more frequently and/or in a higher dose per injection. If one or more diagnostic methods show stark improvement in the disease (e.g., SDOCT shows elimination of all or most soft drusen), treatment with the apo mimetic can be paused or stopped. However, if one or more diagnostic methods show return of the disease after a certain period of time (e.g., SDOCT shows an appreciable or significant amount of soft drusen), treatment with the apo mimetic, such as the treatment regimen that had resulted in the stark improvement, can be resumed. The progression and treatment of AMD can be monitored using diagnostic methods to adjust the treatment accordingly. Such a treatment regimen can be called an "as-needed" or "pro re nata" regimen. An as-needed regimen involves routine clinic visits (e.g., once every 4, 6 or 8 weeks) so that one or more diagnostic methods can be performed to monitor the progression and treatment of AMD, although the therapeutic agent might not be administered during a clinic visit depending on the results of the diagnostic tests.

As another example of treatment of early, intermediate or advanced AMD, or atrophic AMD or neovascular AMD, with an apo mimetic [e.g., an apoA-I mimetic (e.g., L-4F) and/or an apoE mimetic (e.g., AEM-28-14)] administered by injection (e.g., intravitreal, subconjunctival, subretinal or sub-Tenon's injection), the apo mimetic can be administered in a certain frequency of injections (e.g., once monthly) and in a certain dose per injection during the initial phase of treatment. During the second phase of treatment, the apo mimetic can be injected less frequently (e.g., once every 6 or 8 weeks), and in the same dose per injection as the initial dose per injection or in a higher dose per injection so that a substantially similar total dose is administered over a certain time period. The second phase of treatment can last for a selected period of time. During an optional third phase of treatment, the apo mimetic can be injected even less frequently (e.g., once every 10 or 12 weeks), and in the same dose per injection as the initial dose per injection or in a higher dose per injection so that a substantially similar total dose is administered over a certain time period. The optional third phase of treatment can last for a selected period of time. And so on. Such a treatment regimen can be called a "treat-and-extend" regimen. In the initial/first phase, the second phase, the optional third phase and any additional optional phase of treatment, one or more diagnostic methods can be performed to monitor the progression and treatment of AMD and possibly to adjust the treatment depending on the results of the diagnostic tests. For example, if one or more diagnostic methods show a worsening of the disease (e.g., SDOCT shows an increase in soft drusen volume), the apo mimetic can be injected more frequently and/or in a higher dose per injection. In contrast, if one or more diagnostic methods show stability or an improvement in the disease (e.g., SDOCT shows stability or a reduction of soft drusen volume), the apo mimetic can be injected less frequently and/or in a lower dose per injection, or the apo mimetic can be injected less frequently and in a higher dose per injection so that a substantially similar total dose is administered over a certain time period. Unlike an as-needed regimen, a treat-and-extend regimen does not involve routine diagnostic visits, but the therapeutic agent is administered in routine treatment visits (whose frequency decreases in the second phase and the optional third phase of treatment), even though the therapeutic agent, or the dose administered, might not be medically needed at that time. Frequent clinic visits (whether for monitoring and/or treatment) and frequent (e.g., monthly) injections can have negative consequences, such as decreased patient compliance, adverse medical effects (e.g. tachyphylaxis), and increased healthcare cost. A potential advantage of a treat-and-extend regimen over an as-needed regimen is that it can decrease the total number of clinic visits made for monitoring and treatment.

As a non-limiting example of a treat-and-extend regimen, for the treatment of neovascular AMD an anti-angiogenic agent (e.g., an anti-VEGF agent such as aflibercept, bevacizumab or ranibizumab), whether alone or in combination with another therapeutic agent (e.g., an apo mimetic such as an apoA-I mimetic [e.g., L-4F] or an apoE mimetic [e.g., AEM-28-14]) can be injected (e.g., intravitreally) once every 4, 6 or 8 weeks until achievement of a maximal effect, such as substantially complete resolution of subretinal fluid and/or intraretinal fluid without new retinal hemorrhage, or no further reduction of subretinal fluid and/or intraretinal fluid in OCT-FA for at least two consecutive clinic visits in the absence of new retinal hemorrhage. In such a case, the anti-angiogenic agent can be injected less frequently (the interval between injections can be extended by, e.g., about 2 or 4 weeks). If the disease remains stable, the interval between injections can be extended by, e.g., about 2 or 4 weeks at a time, and the total extension period can be up to, e.g., about 3, 4, 5 or 6 months. If the patient shows a relatively mild deterioration in the disease (e.g., reappearance of a relatively small amount of subretinal fluid and/or intraretinal fluid or a relatively small increase in the amount thereof), the interval between injections of the anti-angiogenic agent can be shortened by, e.g., about 1 or 2 weeks. If the disease deterioration is severe, frequent injections (e.g., once every 4, 6 or 8 weeks) of the anti-angiogenic agent can be resumed. Similar principles are also applicable to a treat-and-extend regimen for the treatment of atrophic AMD or neovascular AMD with any other kind of therapeutic agent, including without limitation an apo mimetic (e.g., an apoA-I mimetic such as L-4F or an apoE mimetic such as AEM-28-14) and a complement inhibitor (e.g., a complement factor D inhibitor such as lampalizumab).

Alternative to an as-needed regimen or a treat-and-extend regimen, for the treatment of early, intermediate or advanced AMD, or atrophic AMD or neovascular AMD, a therapeutic agent (e.g., an apo mimetic, an anti-angiogenic agent or a complement inhibitor) can be administered in substantially the same frequency of administration and in substantially the same dose per administration for substantially the entire length of treatment selected by the treating physician or until one or more diagnostic methods indicate that the disease has been successfully treated according to any selected outcome measure(s). Such a treatment regimen can be called a "fixed-routine" regimen.

The apo mimetic [e.g., an apoA-I mimetic (e.g., L-4F) and/or an apoE mimetic (e.g., AEM-28-14)] can be administered as a composition comprising one or more pharmaceutically acceptable excipients or carriers. If two or more apo mimetics (e.g., an apoA-I mimetic and an apoE mimetic) are used, they can be administered in the same composition or in different compositions. In some embodiments, the composition containing the apo mimetic [e.g., an apoA-I mimetic (e.g., L-4F) and/or an apoE mimetic (e.g., AEM-28-14)] comprises about 75-95% (e.g., about 90%) of the apo mimetic(s) and about 5-25% (e.g., about 10%) of the corresponding apolipoprotein(s) (e.g., apoA-I and/or apoE) or an active portion or domain thereof by weight or molarity relative to their combined amount. In certain embodiments, the composition containing the apo mimetic [e.g., an apoA-I mimetic (e.g., L-4F) and/or an apoE mimetic (e.g., AEM-28-14)] is formulated for injection (e.g., intravitreal, subconjunctival, subretinal or sub-Tenon's injection). Examples of formulations for injection into the eye include without limitation those described elsewhere herein. In other embodiments, the composition containing the apo mimetic [e.g., an apoA-I mimetic (e.g., L-4F) and/or an apoE mimetic (e.g., AEM-28-14)] is formulated as an eye drop or an implant (e.g., an intravitreal, subretinal or sub-Tenon's implant). Use of an eye drop, or implantation of the implant one or two times, can avoid potential issues associated with repeated injections.

In further embodiments, the composition containing the apo mimetic [e.g., an apoA-I mimetic (e.g., L-4F) and/or an apoE mimetic (e.g., AEM-28-14)] is configured for sustained release of the apo mimetic. Non-limiting examples of sustained-release compositions include those described elsewhere herein. In certain embodiments, the apo mimetic [e.g., an apoA-I mimetic (e.g., L-4F) and/or an apoE mimetic (e.g., AEM-28-14)] is administered via microparticles, such as polymeric microparticles or microparticles comprising primarily or consisting essentially of the apo mimetic. Use of a sustained-release composition or such microparticles can decrease the number of times a potentially invasive procedure (e.g., intravitreal injection) is performed to administer a drug, and can improve the profile of the amount of the drug delivered to the target site over a period of time.

In some embodiments, the composition containing the apo mimetic [e.g., an apoA-I mimetic (e.g., L-4F) and/or an apoE mimetic (e.g., AEM-28-14)] comprises one or more excipients that inhibit peptide/protein aggregation, increase peptide/protein solubility, reduce solution viscosity or increase peptide/protein stability, or any combination or all thereof. Examples of such excipients include without limitation those described elsewhere herein. Such excipients can improve the injectability of the composition containing the apo mimetic. Therefore, such excipients enable the use of a needle (e.g., an injection needle) having a smaller gauge (e.g., smaller than 30 G) in the administration (e.g., by intravitreal injection) of the composition containing the apo mimetic.

Because such excipients inhibit peptide/protein aggregation and increase peptide/protein solubility, for example, they can be employed to increase the concentration of a peptide or protein in a solution or suspension. Increased peptide/protein concentration decreases the volume needed to administer a given amount of the peptide or protein, which can have beneficial effects such as reduced ocular pressure if the peptide or protein is administered by injection into the eye. Moreover, increased peptide/protein concentration allows a greater dose of the peptide or protein to be administered for a given volume, which can permit the peptide or protein to be administered less frequently for a given total dose administered over a time period. Less frequent administration (e.g., by intravitreal injection) of the peptide or protein can have benefits, such as improved patient compliance and health due to fewer invasive procedures being performed.

The apo mimetic [e.g., an apoA-I mimetic (e.g., L-4F) and/or an apoE mimetic (e.g., AEM-28-14)] can be used alone or in combination with one or more other therapeutic agents to treat AMD. Examples of other therapeutic agents include without limitation those described elsewhere herein. One or more other therapeutic agents can be administered in conjunction with the apo mimetic at different stages of AMD (e.g., the early stage, the intermediate stage or the advanced stage of AMD) and for the treatment of different phenotypes of AMD (e.g., geographic atrophy or neovascular AMD), as described elsewhere herein.

An apolipoprotein mimetic (e.g., an apoA-I mimetic [e.g., L-4F] and/or an apoE mimetic [e.g., AEM-28-14]), optionally in conjunction with one or more other therapeutic agents, can be used to treat any symptoms or complications associated with AMD. Examples of such symptoms and complications include without limitation accumulation of lipids (including neutral lipids and modified lipids) on the BrM, thickening of the BrM, accumulation of lipid-rich debris, deposition of lipid-rich debris (including basal linear deposits and drusen) between the RPE-BL and the BrM ICL, formation of a diffusion barrier between the RPE and the choriocapillaris, degeneration of photoreceptors, geographic atrophy (including non-central and central GA), RPE atrophy, neovascularization (including types 1, 2 and 3 NV), leakage, bleeding and scarring in the eye, and vision impairment and loss.

As a non-limiting example, some embodiments of the disclosure relate to a method of preventing, delaying the onset of, slowing the progression of or reducing the extent of vision impairment or loss associated with AMD, comprising administering to a subject a therapeutically effective amount of an apo mimetic (e.g., an apoA-I mimetic [e.g., L-4F] and/or an apoE mimetic [e.g., AEM-28-14]). One or more other therapeutic agents can optionally be administered. The vision impairment or loss can be associated with atrophic AMD (including non-central and/or central geographic atrophy) or neovascular AMD (including types 1, 2 and/or 3 neovascularization).

V. Other Kinds of Therapeutic Agents

As described above, AMD has a variety of underlying factors, including formation of lipid-containing deposits, formation of toxic byproducts, oxidation, inflammation, neovascularization and cell death. A plurality of therapeutic agents targeting multiple underlying factors of AMD, or having different mechanisms of action, can be utilized for the treatment of AMD. Therapeutic agents that can be used, optionally in combination with apolipoprotein mimetics, to treat AMD include without limitation:
1) anti-dyslipidemic agents;
2) PPAR-α agonists, PPAR-δ agonists and PPAR-γ agonists;
3) anti-amyloid agents;
4) inhibitors of lipofuscin or components thereof;
5) visual/light cycle modulators and dark adaptation agents;
6) antioxidants;
7) neuroprotectors (neuroprotectants);
8) apoptosis inhibitors and necrosis inhibitors;
9) C-reactive protein (CRP) inhibitors;
10) inhibitors of the complement system or components (e.g., proteins) thereof;
11) inhibitors of inflammasomes;
12) anti-inflammatory agents;
13) immunosuppressants;
14) modulators of matrix metalloproteinases (MMPs); and
15) anti-angiogenic agents.

A particular therapeutic agent may exert more than one biological or pharmacological effect and may be classified in more than one category.

A therapeutic agent is used in a therapeutically effective amount. When used in combination with another therapeutic agent (e.g., an apolipoprotein mimetic), a therapeutic agent can be administered substantially simultaneously with the other therapeutic agent (such as during the same doctor's visit, or within about 30 or 60 minutes of each other), or prior to or subsequent to administration of the other therapeutic agent. When administered simultaneously with another therapeutic agent, a therapeutic agent can be administered in the same formulation or in separate formulations as the other therapeutic agent.

Formation of lipid-rich deposits is an important upstream cause of AMD that leads to complications such as non-central and central geographic atrophy and neovascularization. One multi-pronged approach to preventing or minimizing the accumulation of lipid-rich material is to inhibit the production of lipids (e.g., cholesterol and fatty acids) and lipoproteins (e.g., VLDLs) by RPE cells, to inhibit the uptake of plasma lipids (e.g., cholesterol and fatty acids) and lipoproteins (e.g., VLDLs) by RPE cells, to inhibit the secretion of lipids (e.g., cholesterol and fatty acids) and lipoproteins (e.g., VLDLs) and components thereof (e.g., apoB and apoE) by RPE cells into the BrM, the sub-RPE-BL space and the subretinal space, and to clear lipids (e.g., cholesterol and oxidized lipids) and lipoproteins (e.g., VLDLs) and components thereof (e.g., apoB and apoE) from the BrM, the sub-RPE-BL space and the subretinal space. For example, apoB is involved in the formation of at least hepatic VLDL, which is the parent of at least plasma LDL. Inhibition of apoB production by RPE cells and inhibition of the uptake by RPE cells of fatty acids available to lipidate apoB could curtail the production of VLDLs, and hence possibly LDLs, by RPE cells.

Anti-dyslipidemic agents modulate inter alia the production, uptake and clearance of lipids, lipoproteins and other substances that play a role in the formation of lipid-containing deposits in the retina, the subretinal space, the sub-RPE-BL space, and the choroid (e.g., the BrM). One class of anti-dyslipidemic agents is fibrates, which activate peroxisome proliferator-activated receptor-alpha (PPAR-α). Fibrates are hypolipidemic agents that reduce fatty acid and triglyceride production, induce lipoprotein lipolysis but stimulate the production of high-density lipoprotein (HDL, which mediates reverse cholesterol transport), increase LDL removal from plasma, and stimulate reverse cholesterol transport from cells to the circulation and ultimately the liver, where cholesterol is metabolized and excreted into the bile. (Cholesterol can also be cleared through, e.g., the removal of HDL-cholesteryl ester by the gut. Lecithin-cholesterol acyltransferase [LCAT], a plasma enzyme that is activated by, e.g., apolipoprotein A-I, converts free cholesterol into cholesteryl ester, which is then sequestered into the core of HDL particles.) Examples of fibrates include without limitation bezafibrate, ciprofibrate, clinofibrate, clofibric acid, clofibrate, aluminum clofibrate, clofibride, etofibrate, fenofibrate, gemfibrozil, ronifibrate, simfibrate, and analogs, derivatives and salts thereof. Other hypotriglyceridemic agents include omega-3 fatty acids, such as docosahexaenoic acid (DHA) and eicosapentaenoic acid (EPA).

Another class of anti-dyslipidemic agents is HMG-CoA reductase inhibitors (statins). Statins inhibit cholesterol synthesis, decrease the production of VLDL and LDL apoB (or the production of apoB-containing VLDLs and LDLs), reduce apoB secretion, and lower the level of plasma lipids. Examples of statins include, but are not limited to, atorvastatin, cerivastatin, fluvastatin, mevastatin, monacolins (e.g., monacolin K [lovastatin]), pitavastatin, pravastatin, rosuvastatin, simvastatin, and analogs, derivatives and salts thereof.

Other anti-dyslipidemic agents include acetyl-CoA carboxylase (ACC) inhibitors. ACC inhibitors inhibit fatty acid and triglyceride (TG) synthesis and decrease VLDL-TG secretion. Non-limiting examples of ACC inhibitors include anthocyanins, avenaciolides, benzodioxepines {e.g., 7-(4-propyloxy-phenylethynyl)-3,3-dimethyl-3,4 dihydro-2H-benzo[b][1,4]dioxepine}, benzothiophenes [e.g., N-ethyl-N'-(3-{[4-(3,3-dimethyl-1-oxo-2-oxa-7-azaspiro[4.5]dec-7-yl)piperidin-1-yl]-carbonyl}-1-benzothien-2-yl)urea], bis-piperidinylcarboxamides (e.g., CP-640186), chloroacetylated biotin, cyclodim, diclofop, haloxyfop, biphenyl- and 3-phenyl pyridines, phenoxythiazoles {e.g., 5-(3-acetamidobut-1-ynyl)-2-(4-propyloxyphenoxy)thiazole}, piperazine oxadiazoles, (4-piperidinyl)-piperazines, soraphens (e.g., soraphen $A_{1\alpha}$), spiro-piperidines, spiro-pyrazolidinediones, spiro[chroman-2,4'-piperidin]-4-ones, 5-(tetradecyloxy)-2-furancarboxylic acid (TOFA), thiazolyl phenyl ethers, thiophenes [e.g., 1-(3-{[4-(3,3-dimethyl-1-oxo-2-oxa-7-azaspiro[4.5]dec-7-yl)piperidin-1-yl]-carbonyl}-5-(pyridin-2-yl)-2-thienyl)-3-ethylurea], and analogs, derivatives and salts thereof.

Acyl-CoA cholesterol acyltransferase (ACAT) inhibitors can also be used as anti-dyslipidemic agents. ACAT inhibitors inhibit cholesterol esterification and decrease the production of VLDL and LDL apoB (or the production of apoB-containing VLDLs and LDLs). Examples of ACAT inhibitors include without limitation avasimibe, pactimibe, pellitorine, terpendole C, and analogs, derivatives and salts thereof.

Another class of anti-dyslipidemic agents is glucagon-like peptide-1 (GLP-1) receptor agonists. GLP-1 receptor agonists reduce the production of apoB and VLDL particles and hence VLDL-apoB and VLDL-TG, decrease the cellular content of cholesterol and triglycerides, and reduce or reverse hepatic steatosis (fatty liver) by decreasing hepatic lipogenesis. Non-limiting examples of GLP-1 receptor agonists include exendin-4, albiglutide, dulaglutide, exenatide, liraglutide, lixisenatide, semaglutide, taspoglutide, CNTO736, CNTO3649, and analogs, derivatives and salts thereof. Because GLP-1, the endogenous ligand of the GLP-1 receptor, is rapidly degraded by dipeptidyl peptidase 4 (DPP-4), anti-dyslipidemic effects similar to those of GLP-1 receptor agonists can be achieved with the use of a DPP-4 inhibitor, albeit with potentially lower potency. Non-limiting examples of DPP-4 inhibitors include alogliptin, anagliptin, dutogliptin, gemigliptin, linagliptin, saxagliptin, sitagliptin, tenegliptin, vildagliptin, berberine, lupeol, and analogs, derivatives and salts thereof.

Additional anti-dyslipidemic agents include inhibitors of the microsomal triglyceride transfer protein (MTTP), which is expressed in RPE cells. MTTP catalyzes the assembly of cholesterol, triglycerides and apoB to chylomicrons and VLDLs. MTTP inhibitors inhibit the synthesis of apoB-containing chylomicrons and VLDLs, and inhibit the secretion of these lipoproteins. Examples of MTTP inhibitors include, but are not limited to, microRNA (e.g., miRNA-30c), implitapide, lomitapide, dirlotapide, mitratapide, CP-346086, JTT-130, SLx-4090, and analogs, derivatives and salts thereof. Systemic administration of an MTTP inhibitor may result in hepatic steatosis (e.g., accumulation of triglycerides in the liver), which can be averted by, e.g., local administration of the MTTP inhibitor, use of an MTTP inhibitor that is not systemically absorbed (e.g., SLx-4090), or co-administration of a GLP-1 receptor agonist, or any combination or all thereof. Another option for avoiding hepatic steatosis is the use of miRNA-30c. One region of the sequence of miRNA-30c decreases MTTP expression and apoB secretion, and another region decreases fatty acid synthesis, with no deleterious effect to the liver.

Other kinds of anti-dyslipidemic polynucleotides include anti-sense polynucleotides that target mRNA for apoB, including apoB48 and apoB100. ApoB is important in the formation of VLDLs and subsequently LDLs. Use of an anti-sense polynucleotide wholly or partially (e.g., at least about 50%, 60%, 70%, 80%, 90% or 95%) complementary to mRNA for apoB blocks translational expression of apoB and hence the production of VLDLs and LDLs. Examples of anti-sense polynucleotides targeting mRNA for apoB include without limitation mipomersen. Other anti-dyslipidemic anti-sense polynucleotides include those targeting miRNA-33a and miRNA-33b. miRNA-33a and miRNA-33b repress the expression of the ATP-binding cassette transporter ABCA1 (cholesterol efflux regulatory protein

[CERP]), which mediates the efflux of cholesterol and phospholipids. Use of an anti-sense polynucleotide wholly or partially (e.g., at least about 50%, 60%, 70%, 80%, 90% or 95%) complementary to miRNA-33a and/or miRNA-33b increases reverse cholesterol transport and HDL production and decreases VLDL-TG and fatty acid production. Increased expression of ABCA1 is also protective against angiogenesis in AMD.

Furthermore, cholesterylester transfer protein (CETP) inhibitors can be used as anti-dyslipidemic agents. CETP transfers cholesterol from HDLs to VLDLs and LDLs. CETP inhibitors increase HDL level, decrease VLDL and LDL levels, and increase reverse cholesterol transport from cells to the circulation and ultimately the liver, where cholesterol is metabolized and excreted into the bile. Examples of CETP inhibitors include, but are not limited to, anacetrapib, dalcetrapib, evacetrapib, torcetrapib, AMG 899 (TA-8995) and analogs, derivatives and salts thereof.

Other anti-dyslipidemic agents that increase cellular lipid (e.g., cholesterol) efflux include liver X receptor (LXR) agonists and retinoid X receptor (RXR) agonists. LXR heterodimerizes with the obligate partner RXR. The LXR/RXR heterodimer can be activated with either an LXR agonist or an RXR agonist. Activation of the LXR/RXR heterodimer decreases fatty acid synthesis and increases lipid (e.g., cholesterol) efflux from cells to the circulation and ultimately the liver, where lipids are metabolized and excreted into the bile. Non-limiting examples of LXR agonists include endogenous ligands such as oxysterols (e.g., 22(R)-hydroxycholesterol, 24(S)-hydroxycholesterol, 27-hydroxycholesterol and cholestenoic acid), and synthetic agonists such as acetyl-podocarpic dimer, hypocholamide, N,N-dimethyl-3β-hydroxy-cholenamide (DMHCA), GW3965, T0901317, and analogs, derivatives and salts thereof. Non-limiting examples of RXR agonists include endogenous ligands such as 9-cis-retinoic acid, and synthetic agonists such as bexarotene, AGN 191659, AGN 191701, AGN 192849, BMS649, LG100268, LG100754, LGD346, and analogs, derivatives and salts thereof.

PPAR-α agonists and PPAR-γ agonists can also be used to treat AMD. The hypolipidemic effects of the PPAR-α-activating fibrates are described above. Fibrates also decrease the expression of vascular endothelial growth factor (VEGF) and VEGF receptor 2 (VEGFR2), which play an important role in the development of neovascularization, including CNV. Examples of PPAR-α agonists include, but are not limited to, fibrates and perfluoroalkanoic acids (e.g., perfluorooctanoic acid and perfluorononanoic acid). PPAR-γ-activating thiazolidinediones also have anti-dyslipidemic effects. Like LXR, PPAR-γ heterodimerizes with RXR. Thiazolidinediones decrease the level of lipids (e.g., fatty acids and triglycerides), increase the level of HDLs (which mediate reverse cholesterol transport), and increase the efflux of lipids (e.g., cholesterol) from cells to the circulation and ultimately the liver, where lipids are metabolized and excreted into the bile. Like fibrates, thiazolidinediones also inhibit VEGF-induced angiogenesis. Examples of PPAR-γ agonists include without limitation thiazolidinediones (e.g., ciglitazone, lobeglitazone, netoglitazone, pioglitazone, rivoglitazone, rosiglitazone and troglitazone), rhodanine, berberine, honokiol, perfluorononanoic acid, and analogs, derivatives and salts thereof.

Other anti-dyslipidemic PPAR modulators include PPAR-δ agonists. PPAR-δ agonists increase HDL level, reduce VLDL level, and increase the expression of cholesterol efflux transporters (e.g., ABCA1). Non-limiting examples of PPAR-δ agonists include GFT505 (a dual PPAR-ca/6 agonist), GW0742, GW501516, sodelglitazar (GW677954), MBX-8025, and analogs, derivatives and salts thereof.

Anti-dyslipidemic agents also include apolipoprotein peptide mimetics, which are described elsewhere herein.

Another way to increase cholesterol efflux from cells is to increase the level of cardiolipin in the inner mitochondrial membrane. Increased cardiolipin content may also prevent or curtail mitochondrial dysfunction. A non-limiting example of agents that increase the level of cardiolipin in the inner mitochondrial membrane is elamipretide (MTP-131), a cardiolipin peroxidase inhibitor and a mitochondria-targeting peptide.

If systemic administration of an anti-dyslipidemic agent that increases lipid efflux (e.g., reverse cholesterol transport) results in hepatic steatosis or abnormal levels of lipids in the blood, or risks doing so, hepatic steatosis or abnormal levels of lipids in the blood can be averted or treated by, e.g., local administration of the anti-dyslipidemic agent to the eye, co-use of an agent that reduces or reverses hepatic steatosis, or co-use of an agent that decreases lipid levels in the blood, or any combination or all thereof. Examples of agents that reduce or reverse hepatic steatosis include without limitation agents that reduce hepatic lipogenesis, such as GLP-1 receptor agonists, which can be administered, e.g., systemically for this purpose. A non-limiting example of agents that decrease lipid levels in the blood is statins, which can be administered systemically for this purpose.

Other compounds that bind to and neutralize and/or facilitate clearance of lipids and toxic lipid byproducts (e.g., oxidized lipids) can also be used. For example, cyclodextrins have a hydrophilic exterior but a hydrophobic interior, and hence can form water-soluble complexes with hydrophobic molecules. Therefore, cyclodextrins, including α-cyclodextrins (6-membered sugar ring molecules), β-cyclodextrins (7-membered sugar ring molecules), γ-cyclodextrins (8-membered sugar ring molecules) and derivatives thereof (e.g., methyl-β-cyclodextrin), can form water-soluble inclusion complexes with lipids (e.g., cholesterol) and toxic lipid byproducts (e.g., oxidized lipids) and thereby can neutralize their effect and/or facilitate their removal.

Another kind of anti-dyslipidemic agents is endoplasmic reticulum (ER) modulators that restore proper ER function, including without limitation azoramide. The ER plays an important role in lipid metabolism. ER dysfunction and chronic ER stress are associated with many pathologies, including obesity and inflammation. Azoramide improves ER protein-folding ability and activates ER chaperone capacity to protect cells against ER stress.

AMD reportedly is associated with extracellular deposits of apoE and amyloid-beta (Aβ), including in drusen. Aβ deposits reportedly are involved in inflammatory events. Accordingly, anti-amyloid agents (e.g., inhibitors of Aβ formation or aggregation into plaques/deposits, and promoters of Aβ clearance) can potentially be useful for treating AMD. Examples of anti-amyloid agents (e.g., anti-Aβ agents) include without limitation anti-Aβ antibodies (e.g., bapineuzumab, solanezumab, GSK933776, RN6G [PF4382923], AN-1792, 2H6 and deglycosylated 2H6), anti-apoE antibodies (e.g., HJ6.3), apoE mimetics (e.g., AEM-28), cystatin C, berberine, L-3-n-butylphthalide, T0901317, and analogs, derivatives, fragments and salts thereof.

Elevated levels of other toxic byproducts are also associated with AMD. For example, elevated levels of toxic aldehydes such as 4-hydroxynonenal (HNE) and malondialdehyde (MDA) are present in patients with AMD, particularly atrophic AMD. An agent that inhibits the formation of toxic aldehydes, binds to them and lowers their level, or promotes their breakdown or clearance, such as the aldehyde trap NS2, can be used to treat AMD.

In addition, with age lipofuscin and components thereof (e.g., A2E) reportedly accumulate in the RPE as a byproduct of visual cycling. The lipofuscin bisretinoid A2E reportedly inhibits lysosomal degradative function and cholesterol metabolism in the RPE, induces the complement system and mediates blue light-induced apoptosis, and thus has been implicated in the atrophy and cell death of RPE cells. Accordingly, inhibitors of lipofuscin or components thereof (e.g., A2E), including inhibitors of their formation or accumulation and promoters of their breakdown or clearance, can potentially be useful for treating AMD. Examples of inhibitors of lipofuscin or components thereof (e.g., A2E) include without limitation isotretinoin, which inhibits the formation of A2E and accumulation of lipofuscin pigments; soraprazan, which promotes the release of lipofuscin from RPE cells; and retinol-binding protein 4 (RBP4) antagonists (e.g., A1120 and compound 43 [a cyclopentyl-fused pyrrolidine]), which inhibit the formation of lipofuscin bisretinoids such as A2E.

Another potential way to prevent or curtail the accumulation of lipofuscin bisretinoids (e.g., A2E) is to interfere with the visual/light cycle in photoreceptors. For example, the visual/light cycle modulator fenretinide reduces serum levels of retinol and RBP4 and inhibits retinol binding to RBP4, which decreases the level of light cycle retinoids and halts the accumulation of lipofuscin bisretinoids (e.g., A2E). Other visual/light cycle modulators include without limitation inhibitors of the trans-to-cis-retinol isomerase RPE65 (e.g., emixustat [ACU-4429] and retinylamine), which, by inhibiting the conversion of all-trans retinol to 11-cis retinol in the RPE, reduce the amount of retinol available and its downstream byproduct A2E. Treatment with a light cycle modulator may slow the rate of the patient's rod-mediated dark adaptation. To speed up the rate of dark adaptation, a dark adaptation agent can be administered. Non-limiting examples of dark adaptation agents include carotenoids (e.g., carotenes, such as β-carotene), retinoids (e.g., all-trans retinol [vitamin A], 11-cis retinol, all-trans retinal [vitamin A aldehyde], 11-cis retinal, all-trans retinoic acid [tretinoin] and esters thereof, 9-cis-retinoic acid [alitretinoin] and esters thereof, 11-cis retinoic acid and esters thereof, 13-cis-retinoic acid [isotretinoin] and esters thereof, etretinate, acitretin, adapalene, bexarotene and tazarotene), and analogs, derivatives and salts thereof.

Oxidative events play a significant role in the pathogenesis of AMD. For instance, accumulation of peroxidized lipids can lead to inflammation and neovascularization. To prevent, delay the onset of or slow the progression of AMD, antioxidants can be administered. In addition, antioxidants can be neuroprotective by preventing or curtailing toxicity in the retina and interfering with cell-death pathways. For example, the mitochondria-targeting electron scavenger XJB-5-131 inhibits oxidation of cardiolipin, a mitochondria-specific polyunsaturated phospholipid, thereby curtailing cell death, including in the brain. As another example, crocin and crocetin, carotenoids found in saffron, can protect cells from apoptosis. As yet another example, xanthophylls (e.g., lutein and zeaxanthin) can protect against development of drusen-like lesions at the RPE, loss of macular pigment and light-induced photoreceptor apoptosis. As still another example, carnosic acid, a benzenediol abietane diterpene found in rosemary and sage, can upregulate antioxidant enzymes, protect retinal cells from hydrogen peroxide toxicity, and increase the thickness of the outer nuclear layer. As a further example, curcuminoids (e.g., curcumin) found in turmeric can upregulate hemeoxygenase-1, thereby protecting RPE cells from hydrogen peroxide-induced apoptosis. As a yet further example, zinc increases catalase and glutathione peroxidase activity, thereby protecting RPE cells and photoreceptors from hydrogen peroxide and tert-butyl hydroperoxide, and protects photoreceptors and other retinal cells from caspase-mediated cell death. As a still further example, cyclopentenone prostaglandins (e.g., cyclopentenone 15-deoxy-A-prostaglandin $J_2$ [15d-$PGJ_2$], a ligand for PPAR-γ) can protect RPE cells from oxidative injury by, e.g., upregulating the synthesis of glutathione, an antioxidant. Cyclopentenone prostaglandins also possess anti-inflammatory property.

Non-limiting examples of antioxidants include anthocyanins, apolipoprotein mimetics (e.g., apoA-I mimetics and apoE mimetics), benzenediol abietane diterpenes (e.g., carnosic acid), carnosine, carotenoids (e.g., carotenes [e.g., β-carotene], xanthophylls [e.g., lutein, zeaxanthin and meso-zeaxanthin], and carotenoids in saffron [e.g., crocin and crocetin]), curcuminoids (e.g., curcumin), cyclopentenone prostaglandins (e.g., 15d-$PGJ_2$), flavonoids (e.g., flavonoids in *Ginkgo biloba* [e.g., myricetin and quercetin]), prenylflavonoids (e.g., isoxanthohumol), retinoids, stilbenoids (e.g., resveratrol), uric acid, vitamin A, vitamin $B_1$ (thiamine), vitamin $B_2$ (riboflavin), vitamin $B_3$ (niacin), vitamin $B_6$ (e.g., pyridoxal, pyridoxamine, 4-pyridoxic acid and pyridoxine), vitamin $B_9$ (folic acid), vitamin $B_{12}$ (cobalamin), vitamin C, vitamin E (e.g., tocopherols and tocotrienols), selenium, zinc (e.g., zinc monocysteine), inhibitors and scavengers of lipid peroxidation and byproducts thereof (e.g., vitamin E [e.g., α-tocopherol], tirilazad, NXY-059 and XJB-5-131), activators of nuclear factor (erythroid-derived 2)-like 2 (NFE2L2 or NRF2) (e.g., OT-551), superoxide dismutase (SOD) mimetics (e.g., OT-551), and analogs, derivatives and salts thereof.

Antioxidants can be provided by way of, e.g., a dietary supplement, such as an AREDS or AREDS2 formulation, an ICAPS® formulation, an Ocuvite® formulation, Saffron 2020™ or Phototrop®. If a supplement contains a relatively high amount of zinc (e.g., zinc acetate, zinc oxide or zinc sulfate), copper (e.g., cupric oxide or cupric sulfate) can optionally be co-administered with zinc to prevent copper-deficiency anemia associated with high zinc intake. Saffron 2020™ contains saffron, resveratrol, lutein, zeaxanthin, vitamins A, $B_2$, C and E, zinc and copper. Phototrop® comprises acetyl-L-carnitine, omega-3 fatty acids and coenzyme $Q_{10}$. An exemplary Age-Related Eye Disease Study (AREDS) formulation includes β-carotene, vitamin C, vitamin E, zinc (e.g., zinc oxide) and copper (e.g., cupric oxide). Exemplary AREDS2 formulations contain:
1) β-carotene, vitamin C, vitamin E and zinc; or
2) vitamin C, vitamin E, zinc and copper; or
3) vitamin C, vitamin E and zinc; or
4) β-carotene, vitamin C, vitamin E, omega-3 fatty acids, zinc and copper; or
5) β-carotene, vitamin C, vitamin E, lutein, zeaxanthin, zinc and copper; or
6) β-carotene, vitamin C, vitamin E, lutein, zeaxanthin, omega-3 fatty acids, zinc and copper.

Exemplary ICAPS® formulations include:
1) vitamin A, vitamin C, vitamin E, zinc and copper; or
2) vitamin A, vitamin $B_2$, vitamin C, vitamin E, lutein, zeaxanthin, zinc, copper and selenium.

Exemplary Ocuvite® formulations contain:
1) vitamin C, vitamin E, lutein, zeaxanthin, zinc and copper; or
2) vitamin C, vitamin E, lutein, zeaxanthin, omega-3 fatty acids, zinc and copper; or
3) vitamin A, vitamin C, vitamin E, lutein, zeaxanthin, zinc, copper and selenium.

Alternative to or in addition to antioxidants, other neuroprotectors (neuroprotectants) can be administered to treat AMD. Neuroprotectors can be used, e.g., to promote the health and/or growth of cells in the retina, and/or to prevent cell death regardless of the initiating event. For instance, ciliary neurotrophic factor (CNTF) rescues photoreceptors from degeneration. As another example, glatiramer acetate reduces retinal microglial cytotoxicity (and inflammation). Examples of neuroprotectors include without limitation berberine, glatiramer acetate, $\alpha_2$-adrenergic receptor agonists (e.g., apraclonidine and brimonidine), serotonin $5-HT_{1A}$ receptor agonists (e.g., AL-8309B and azapirones [e.g., buspirone, gepirone and tandospirone]), neuroprotectins (e.g., neuroprotectins A, B and D1), endogenous neuroprotectors {e.g., carnosine, CNTF, glial cell-derived neurotrophic factor (GDNF) family (e.g., GDNF, artemin, neurturin and persephin), and neurotrophins (e.g., brain-derived neurotrophic factor [BDNF], nerve growth factor [NGF], neurotrophin-3 [NT-3] and neurotrophin-4 [NT-4])}, prostaglandin analogs (e.g., unoprostone isopropyl [UF-021]), and analogs, derivatives, fragments and salts thereof.

Furthermore, other neuroprotectors that can be used to treat AMD include agents that prevent the death of retina-associated cells (e.g., RPE cells and photoreceptors) by apoptosis (programmed cell death) and/or necrosis (characterized by cell swelling and rupture). For example, nucleoside reverse transcriptase inhibitors (NRTIs) block the death of RPE cells via inhibition of P2X7-mediated NLRP3 inflammasome activation of caspase-1, and reduce geographic atrophy and CNV. If apoptosis is reduced (e.g., through inhibition of caspases), necrosis may increase to compensate for the reduction in apoptosis, so an effective strategy for preventing or curtailing the death of retina-associated cells can involve inhibition of both apoptosis and necrosis. Non-limiting examples of apoptosis inhibitors include inhibitors of caspases (e.g., caspase family [e.g., Q-VD(OMe)—OPh (SEQ. ID. NO. 14), Boc-D-FMK (SEQ. ID. NO. 15), Z-VAD (SEQ. ID. NO. 16) and Z-VAD-FMK (SEQ. ID. NO. 17)], caspase-1 [e.g., Z-YVAD-FMK (SEQ. ID. NO. 18)], caspase-2 [e.g., Z-VDVAD-FMK (SEQ. ID. NO. 19)], caspase-3 [e.g., Q-DEVD-OPh (SEQ. ID. NO. 20), Z-DEVD-FMK (SEQ. ID. NO. 21) and Z-DQMD-FMK (SEQ. ID. NO. 22)], caspase-4 [e.g., Z-LEVD-FMK (SEQ. ID. NO. 23)], caspase-5 [e.g., Z-WEHD-FMK (SEQ. ID. NO. 24)], caspase-6 [e.g., Z-VEID-FMK (SEQ. ID. NO. 25)], caspase-8 [e.g., Q-IETD-OPh (SEQ. ID. NO. 26) and Z-IETD-FMK (SEQ. ID. NO. 27)], caspase-9 [e.g., Q-LEHD-OPh (SEQ. ID. NO. 28) and Z-LEHD-FMK (SEQ. ID. NO. 29)], caspase-10 [e.g., AEVD-FMK (SEQ. ID. NO. 30)], caspase-12 [e.g., Z-ATAD-FMK (SEQ. ID. NO. 31)] and caspase-13 [e.g., LEED-FMK (SEQ. ID. NO. 32)]), inhibitors of inflammasomes, inhibitors of P2X7-mediated NLRP3 activation of caspase-1 (e.g., NRTIs, such as abacavir [ABC], lamivudine [3TC], stavudine [d4T], me-d4T and zidovudine [AZT]), neuroprotectins, and analogs, derivatives and salts thereof. Examples of necrosis inhibitors include without limitation caspase inhibitors, inhibitors of receptor-interacting protein (RIP) kinases (e.g., necrostatins, such as necrostatins 1, 5 and 7), Necrox compounds (e.g., Necrox-2 and Necrox-5), Nec-1s, and analogs, derivatives and salts thereof.

Elevated levels of C-reactive protein (CRP) are found in the blood and eyes of patients with AMD. Elevated CRP levels can increase VEGF production and thereby lead to neovascularization. In addition, CRP is implicated in the pathogenesis of inflammation, and inhibits cholesterol efflux through down-regulation of the cholesterol efflux proteins ABCA1 and ABCG1. Moreover, monomeric CRP can bind to the complement protein C1q and subsequently activate the classical complement pathway, which in tandem with the alternative complement pathway can result in the formation of the membrane attack complex (MAC) and eventually cell lysis. Accordingly, CRP inhibitors that curtail the level (e.g., via decreased production or increased breakdown or clearance) or the activity of CRP can be used to treat AMD. Examples of CRP inhibitors include without limitation DPP-4 inhibitors, thiazolidinediones, stilbenoids, statins, epigallocatechin-3-gallate (EGCG), CRP-i2, and analogs, derivatives and salts thereof.

The complement system of the innate immune system is implicated in the pathogenesis of AMD. For example, variants of the CFH gene resulting in defective or deficient complement factor H (CFH) are strongly associated with risk for AMD. Further, the alternative complement pathway may be activated by the accumulation of apolipoproteins (e.g., apoE) and lipofuscin or components thereof (e.g., A2E). In addition, the membrane attack complex (MAC, C5b-9) has been documented on choroidal blood vessels, the Bruch's membrane (BrM) and the RPE and is associated with abnormal RPE cells, suggesting that complement-mediated cell lysis may accelerate RPE dysfunction and death in AMD. Moreover, there is a marked accumulation of the MAC in the BrM and the choriocapillaris endothelium of the aging macula. The complement system also plays a significant role in inflammatory and oxidative events. As an example, the anaphylatoxins C3a, C4a and C5a mediate inflammation and generation of cytotoxic oxygen radicals. For instance, binding of C3a and C5a to the C3a and C5a receptors, respectively, leads to an inflammatory response, e.g., by stimulating mast cell-mediated inflammation via histamine release. Activation of the complement cascade and local inflammation are implicated in, e.g., drusen formation, a hallmark of atrophic AMD that can lead to neovascular AMD. In addition, the complement system is implicated in neovascularization, including CNV. For instance, activation of the complement system may result in formation of the MAC in the choriocapillary endothelium, whose breakdown by the MAC can lead to hypoxia and thus CNV. Furthermore, some complement components (e.g., C5a) exhibit pro-angiogenic properties—e.g., the C5a receptor mediates increased VEGF secretion in RPE cells. Moreover, the MAC releases pro-angiogenic molecules (e.g., PDGF and VEGF).

Alternative to or in addition to inhibition of the alternative complement pathway, inhibition of the lectin complement pathway (and/or classic complement pathway) can be beneficial in the treatment of atrophic AMD and/or neovascular AMD. For example, inhibition of a mannan-binding lectin serine protease (or mannose-associated serine protease [MASP]) (e.g., MASP-1, -2 or -3) using, e.g., an antibody or a fragment thereof (e.g., OMS721, an anti-MASP-2 antibody), can dampen amplification of complement activation and sequelae thereof, such as inflammation. In the lectin pathway, MASPs cleave C2 and C4 to form C2aC4b, a C3-convertase. At the border of the lectin and alternative pathways, the C3-convertase cleaves C3 into C3a and C3b. C3b binds to C2aC4b to form a C5-convertase, which cleaves C5 into C5a and C5b. C5b, C6, C7, C8 and C9 together form the membrane attack complex (MAC), which may result in cell lysis via cell swelling and bursting. Complement factors H and I inactivate C3b and downregulate the alternative pathway, thereby suppressing inflammation, for example. By inhibiting the formation of the C3-convertase C2aC4b, a MASP inhibitor can be useful for treating atrophic AMD and/or neovascular AMD.

Accordingly, AMD can be treated using inhibitors of the complement system or components (e.g., proteins and factors) thereof (e.g., CFB, CFD, C2, C2a, C2b, C4, C4a, C4b, C3-convertases [e.g., C2aC4b and C3bBb], C3, C3a, C3b, C3a receptor, C3[$H_2O$], C3[$H_2O$]Bb, C5-convertases [e.g., C2aC3bC4b and C3bBbC3b], C5, C5a, C5b, C5a receptors, C6, C7, C8, C9 and MAC [C5b-9]). As an illustrative example, lampalizumab is an antigen-binding fragment ($F_{ab}$) of a humanized monoclonal antibody targeting complement factor D (CFD), the rate-limiting enzyme involved in the activation of the alternative complement pathway (ACP). CFD cleaves CFB into the proteolytically active factor Bb. Bb binds to spontaneously hydrolysed C3 [C3($H_2O$)], which leads to the formation of the C5-convertase C3bBbC3b. Hyperactivity of the ACP is implicated in the development of AMD, including geographic atrophy (GA). Lampalizumab inhibits complement activation and inflammation and can be used to treat or slow the progression of AMD, including GA. Atrophic AMD patients with a mutation in complement factor I (CFI) appear to exhibit a more positive response to lampalizumab treatment. In the MAHALO Phase II trial, patients receiving monthly intravitreal injections of 10 mg lampalizumab in one eye for 18 months exhibited a reduction in the area of geographic atrophy in the injected eye by about 20% according to fundus autofluorescence compared to patients receiving a placebo. A subgroup of patients positive for the CFI biomarker and receiving monthly intravitreal injections of 10 mg lampalizumab for 18 months exhibited an enhanced reduction in the area of geographic atrophy by about 44%. CFI, a C3b/C4b inactivator, regulates complement activation by cleaving cell-bound or fluid-phase C3b and C4b.

Non-limiting examples of inhibitors of the complement system or components thereof include sCR1 (a soluble form of complement receptor 1 [CR1] that promotes the degradation of C3bBb and inhibits the classic and alternative complement pathways), TT30 (a fusion protein containing domains of complement receptor 2 [CR2] and CFH which inhibits the alternative pathway), anti-CFB antibodies and fragments thereof (e.g., TA106), anti-CFD antibodies and fragments thereof (e.g., lampalizumab [FCFD4514S]), compstatin and derivatives thereof (e.g., POT-4 [AL-78898A]) (inhibit C3 and MAC formation), mycophenolic acid-glucosamine conjugates (downregulators of C3), soluble forms of proteins or fragments thereof as C3 inhibitors (e.g., CR1, decay acceleration factor [DAF] and membrane cofactor protein [MCP or CD46]), 3E7 (an anti-C3b/iC3b monoclonal antibody), anti-C5 antibodies and fragments thereof (e.g., eculizumab [inhibits C5 and MAC formation] and LFG316), anti-C5 aptamers (e.g., ARC1905 [Zimura®], an inhibitor of C5 cleavage), other C5 inhibitors (e.g., Coversin), C5a receptor antagonists (e.g., JPE-1375, JSM-7717, PMX-025, Ac-F[OPdChaWR] {PMX-53}, and anti-C5aR antibodies and fragments thereof [e.g., neutrazimab]), apoA-I mimetics (e.g., L-4F, an inhibitor of complement activation), CD59 and modified CD59 having a glycolipid anchor (inhibitors of the MAC), tandospirone (reduces complement deposits), zinc (an inhibitor of complement activation and MAC deposition), and analogs, derivatives, fragments and salts thereof.

Inflammation is also an important contributor to the pathogenesis of AMD. For example, inflammatory responses may be involved in drusen formation, and can upregulate the expression of VEGF and other pro-angiogenic factors that cause neovascularization, including CNV. Inflammation can be mediated by the cellular immune system (e.g., dendritic cells) and/or the humoral immune system (e.g., the complement system). Inflammation can also be mediated by inflammasomes, which are components of the innate immune system. For example, accumulation of material (e.g., lipoprotein-like particles, lipids and possibly lipofuscin or components thereof [e.g., A2E]) in the BrM may activate the NLRP3 inflammasome, leading to a chronic inflammatory response. In addition, assembly of inflammasomes (e.g., NLRP3) in response to cell-stress signals activates caspases (e.g., caspase-1), which results in inflammation (e.g., via production of pro-inflammatory interleukin-1β) and ultimately cell death (e.g., of RPE cells).

Many of the substances mentioned in this disclosure possess anti-inflammatory property in addition to the property or properties described for them. Other anti-inflammatory agents include without limitation hydroxychloroquine, corticosteroids (e.g., fluocinolone acetonide and triamcinolone acetonide), steroids having little glucocorticoid activity (e.g., anecortave [anecortave acetate]), non-steroidal anti-inflammatory drugs (e.g., non-selective cyclooxygenase [COX] 1/COX-2 inhibitors [e.g., aspirin] and COX-2-selective inhibitors [e.g., coxibs]), mast cell stabilizers and inflammasome inhibitors. Examples of inhibitors of inflammasomes (e.g., inhibitors of their assembly or function) include without limitation NLRP3 (NALP3) inhibitors (e.g., interleukin-4 [IL-4], omega-3 fatty acids, anthraquinones [e.g., chrysophanol], sesquiterpene lactones [e.g., parthenolide], sulfonylureas [e.g., glyburide], triterpenoids [e.g., asiatic acid] and vinyl sulfones [e.g., Bay 11-7082]), NLRP3/AIM2 inhibitors (e.g. diarylsulfonylureas [e.g., CP-456,773]), NLRP1 inhibitors (e.g., Bcl-2, the loop region of Bcl-2, and Bcl-X[L]), NLRP1B inhibitors (e.g., auranofin), and analogs, derivatives, fragments and salts thereof.

Non-limiting examples of corticosteroids (not including mineralocorticoids) include hydrocortisone types (e.g., cortisone, hydrocortisone [cortisol], prednisolone, methylprednisolone, prednisone and tixocortol), betamethasone types (e.g., betamethasone, dexamethasone and fluocortolone), halogenated steroids (e.g., alclometasone, beclometasone, clobetasol, clobetasone, desoximetasone, diflorasone, diflucortolone, fluprednidene, fluticasone, halobetasol [ulobetasol], halometasone and mometasone), acetonides and related substances (e.g., amcinonide, budesonide, ciclesonide, desonide, fluocinonide, fluocinolone acetonide, flurandrenolide [fludroxycortide], halcinonide, triamcinolone acetonide and triamcinolone), carbonates (e.g., prednicarbate), and analogs, derivatives and salts thereof.

Examples of non-steroidal anti-inflammatory drugs (NSAIDs) include without limitation:

acetic acid derivatives, such as aceclofenac, bromfenac, diclofenac, etodolac, indomethacin, ketorolac, nabumetone, sulindac, sulindac sulfide, sulindac sulfone and tolmetin;

anthranilic acid derivatives (fenamates), such as flufenamic acid, meclofenamic acid, mefenamic acid and tolfenamic acid;

enolic acid derivatives (oxicams), such as droxicam, isoxicam, lornoxicam, meloxicam, piroxicam and tenoxicam;

propionic acid derivatives, such as fenoprofen, flurbiprofen, ibuprofen, dexibuprofen, ketoprofen, dexketoprofen, loxoprofen, naproxen and oxaprozin;

salicylates, such as diflunisal, salicylic acid, acetylsalicylic acid (aspirin), choline magnesium trisalicylate, and salsalate;

COX-2-selective inhibitors, such as apricoxib, celecoxib, etoricoxib, firocoxib, fluorocoxibs (e.g., fluorocoxibs A-C), lumiracoxib, mavacoxib, parecoxib, rofecoxib, tilmacoxib (JTE-522), valdecoxib, 4-O-methylhonokiol, niflumic acid, DuP-697, CG100649, GW406381, NS-398, SC-58125, benzothieno[3,2-d]pyrimidin-4-one sulfonamide thio-derivatives, and COX-2 inhibitors derived from *Tribulus terrestris*;

other kinds of NSAIDs, such as anilinopyridinecarboxylic acids (e.g., clonixin), sulfonanilides (e.g., nimesulide), and dual inhibitors of lipooxygenase (e.g., 5-LOX) and cyclooxygenase (e.g., COX-2) (e.g., chebulagic acid, licofelone, 2-(3,4,5-trimethoxyphenyl)-4-(N-methylindol-3-yl)thiophene, and di-tert-butylphenol-based compounds [e.g., DTPBHZ, DTPINH, DTPNHZ and DTPSAL]); and analogs, derivatives and salts thereof.

In non-central and central geographic atrophy, mast cells degranulate in the choroid, releasing histamine and other mediators of inflammation. Mast cell stabilizers block a calcium channel essential for mast cell degranulation, stabilizing the mast cell and thereby preventing the release of histamine and other inflammation mediators. Examples of mast cell stabilizers include without limitation $\beta_2$-adrenergic receptor agonists, cromoglicic acid, ketotifen, methylxanthines, nedocromil, olopatadine, omalizumab, pemirolast, quercetin, tranilast, and analogs, derivatives and salts thereof. Examples of short-acting β-adrenergic agonists include without limitation bitolterol, fenoterol, isoprenaline (isoproterenol), levosalbutamol (levalbuterol), orciprenaline (metaproterenol), pirbuterol, procaterol, ritodrine, salbutamol (albuterol), terbutaline, and analogs, derivatives and salts thereof. Non-limiting examples of long-acting β-adrenergic agonists include arformoterol, bambuterol, clenbuterol, formoterol, salmeterol, and analogs, derivatives and salts thereof. Examples of ultralong-acting $3_2$-adrenergic agonists include without limitation carmoterol, indacaterol, milveterol, olodaterol, vilanterol, and analogs, derivatives and salts thereof.

In summary, examples of anti-inflammatory agents include without limitation hydroxychloroquine, anti-amyloid agents, antioxidants, apolipoprotein mimetics (e.g., apoA-I mimetics and apoE mimetics), C-reactive protein inhibitors, complement inhibitors, inflammasome inhibitors, neuroprotectors (e.g., glatiramer acetate), corticosteroids, steroids having little glucocorticoid activity (e.g., anecortave), non-steroidal anti-inflammatory drugs (NSAIDs), mast cell stabilizers, cyclopentenone prostaglandins, anti-angiogenic agents (e.g., anti-VEGF/VEGFR agents), and immunosuppressants.

Other therapeutic agents that can be used to treat atrophic AMD and/or neovascular AMD include immunosuppressants. Immunosuppressants can have anti-inflammatory property. Examples of immunosuppressants include, but are not limited to, inhibitors of interleukin-2 (IL-2) signaling, production or secretion (e.g., antagonists of the IL-2 receptor alpha subunit [e.g., basiliximab and daclizumab], mTOR inhibitors [e.g., rapamycin (sirolimus), deforolimus (ridaforolimus), everolimus, temsirolimus, umirolimus (biolimus A9) and zotarolimus], and calcineurin inhibitors [e.g., cyclosporine, pimecrolimus and tacrolimus]) and inhibitors of tumour necrosis factors (e.g., TNF-α) (e.g., adalimumab, certolizumab pegol, etanercept, golimumab and infliximab).

As a non-limiting example of the potential benefits of the use of an immunosuppressant, an immunosuppressant can reduce the number or frequency of administration of an anti-angiogenic agent (e.g., the number or frequency of injections of an anti-VEGF/VEGFR agent) in the treatment of neovascular AMD.

Matrix metalloproteinases (MMPs) degrade extracellular matrix (ECM) proteins and play an important role in cell migration (dispersion and adhesion), cell proliferation, cell differentiation, angiogenesis and apoptosis. For example, as AMD progresses to the advanced stage, elevated levels of MMPs can degrade the Bruch's membrane (BrM), an ECM and part of the choroid. Endothelial cells migrate along the ECM to the site of injury, proliferate, form endothelial tubes, and mature into new blood vessels that arise from capillaries in the choroid and grow through the fractured BrM. Furthermore, breakage in the BrM may allow endothelial cells to migrate into the sub-RPE-BL space and form immature blood vessels that are leaky and tortuous and may extend into the subretinal space. The net result is neovascularization (including CNV) and development of neovascular AMD. MMPs can also cleave peptide bonds of cell-surface receptors, releasing pro-apoptotic ligands such as FAS. MMP inhibitors can be used, e.g., to inhibit angiogenesis and apoptosis, and to treat neovascular AMD (including types 1, 2 and/or 3 neovascularization) or atrophic AMD (including non-central and/or central geographic atrophy). For example, doxycycline curtails loss of photoreceptors. Non-limiting examples of MMP inhibitors include tissue inhibitors of metalloproteinases (e.g., TIMPs 1, 2, 3 and 4), tetracyclines (e.g., doxycycline, incyclinide and minocycline), dichloromethylenediphosphonic acid, batimastat, cipemastat, ilomastat, marimastat, prinomastat, rebimastat, tanomastat, ABT-770, MMI-166, MMI-270, Ro 28-2653, RS-130830, CAS Reg. No. (CRN) 239796-97-5, CRN 420121-84-2, CRN 544678-85-5, CRN 556052-30-3, CRN 582311-81-7, CRN 848773-43-3, CRN 868368-30-3, and analogs, derivatives, fragments and salts thereof.

Alternative to or in addition to MMP inhibitors, other kinds of inhibitors of cell migration can be utilized. For example, rho kinase (ROCK) inhibitors, including ROCK1 and ROCK2 inhibitors, block cell migration, including endothelial cell migration in the early stages of neovascularization. Examples of ROCK inhibitors include without limitation fasudil, netarsudil, ripasudil, GSK-429286A, RKI-1447, Y-27632 and Y-30141.

In some circumstances, the use of an MMP activator rather than an MMP inhibitor may be desired. The BrM undergoes constant turnover, mediated by MMPs and TIMPs. The BrM thickens progressively with age, partly because of increased levels of TIMPs and a resulting reduction in ECM turnover. Thickening of ECM in the BrM with age may result in the BrM's retention of lipoproteins secreted by the RPE, eventually leading to the formation of BLinD and drusen. The accumulation of lipid-rich BLinD and basal laminar deposits (BlamD, which are excess extracellular matrix in thickened RPE-BL) lengthen the diffusion distance between the choriocapillaris and the RPE. An MMP activator can be used to achieve greater BrM turnover and less thickening of the BrM, but not to the point where the BrM becomes so degraded that new blood vessels can grow through the BrM. Examples of MMP activators include without limitation basigin (extracellular matrix metalloproteinase inducer [EMMPRIN] or CD147), concanavalin A, cytochalasin D, and analogs, derivatives, fragments and salts thereof. Similarly, a matrix metalloproteinase can be employed to reduce the thickness of BLamD persisting over the BrM.

Angiogenesis is the underlying mechanism of neovascularization (including types 1, 2 and 3), which can occur in the advanced stage of AMD to lead to neovascular AMD and severe vision loss if left untreated. Neovascular AMD is characterized by vascular growth and fluid leakage in the choroid, the sub-RPE-BL space, the subretinal space and the neural retina. Leakage from blood vessels can be more responsible for vision loss associated with neovascular AMD than growth of new blood vessels. Vascular endothelial growth factors (VEGFs) are pivotal in the pathogenesis of neovascular AMD. VEGFs are potent, secreted endothelial-cell mitogens that stimulate the migration and proliferation of endothelial cells, and increase the permeability of new blood vessels, resulting in leakage of fluid, blood and proteins from them. In addition, VEGFs increase the level of MMPs, which degrade the ECM further. Moreover, VEGFs enhance the inflammatory response. However, VEGFs or receptors therefor are not the only potential targets for anti-angiogenic agents. For example, targeting integrins associated with receptor tyrosine kinases using an integrin inhibitor (e.g., ALG-1001) inhibits the production and growth of new blood vessels and reduces the permeability (leakage) of blood vessels. Angiogenesis can also be inhibited through inhibition of other targets, including without limitation kinases (e.g., tyrosine kinases, such as receptor tyrosine kinases) and phosphatases (e.g., tyrosine phosphatases, such as receptor tyrosine phosphatases).

Anti-angiogenic agents can be used to prevent or curtail neovascularization (including types 1, 2 and 3), and to reduce the permeability/leakage of blood vessels. For example, interleukin-18 (IL-18) eliminates VEGFs from the eye, thereby inhibiting the formation of damaging blood vessels behind the retina. Non-limiting examples of anti-angiogenic agents include inhibitors of VEGFs (e.g., squalamine, PAN-90806, anti-VEGF antibodies and fragments thereof such as bevacizumab [AVASTIN®], ranibizumab [LUCENTIS®], ESBA1008 and ESBA903, anti-VEGF aptamers such as pegaptanib [MACUGEN®], anti-VEGF designed ankyrin repeat proteins [DARPins] such as abicipar pegol [AGN-150998 or MP0112], soluble VEGFRs [e.g., VEGFR1], and soluble fusion proteins containing one or more extracellular domains of one or more VEGFRs [e.g., VEGFR1 and VEGFR2], such as aflibercept [EYLEA®] and conbercept), inhibitors of receptors for VEGFs (VEGFRs) (e.g., axitinib, pazopanib, sorafenib, sunitinib, X-82, PF-337210, isoxanthohumol, and anti-VEGFR antibodies and fragments thereof), inhibitors of platelet-derived growth factors (PDGFs) (e.g., squalamine, anti-PDGF aptamers such as E10030 [FOVISTA®], anti-PDGF antibodies and fragments thereof, and soluble PDGFRs) or receptors therefor (PDGFRs) (e.g., axitinib, pazopanib, sorafenib, sunitinib, X-82, and anti-PDGF antibodies and fragments thereof [e.g., REGN2176-3]), inhibitors of fibroblast growth factors (FGFs) (e.g., squalamine, anti-FGF antibodies and fragments thereof, anti-FGF aptamers and soluble FGFRs) or receptors therefor (FGFRs) (e.g., anti-FGFR antibodies and fragments thereof), inhibitors of angiopoietins (e.g., anti-angiopoietin antibodies and fragments thereof such as nesvacumab [REGN910] and REGN910-3, and soluble angiopoietin receptors) or receptors therefor (e.g, antibodies and fragments thereof against angiopoietin receptors), inhibitors of integrins (e.g., ALG-1001, JSM-6427, and anti-integrin antibodies and fragments thereof), anecortave (anecortave acetate), angiostatin (e.g., angiostatin K1-3), $\alpha_v\beta_3$ inhibitors (e.g., etaracizumab), apoA-I mimetics (e.g., L-4F and L-5F), berberine, bleomycins, borrelidin, carboxyamidotriazole, cartilage-derived angiogenesis inhibitors (e.g., chondromodulin I and troponin I), castanospermine, CM101, inhibitors of the complement system, cyclopropene fatty acids (e.g., sterculic acid), $\alpha$-difluoromethylornithine, endostatin, everolimus, fumagillin, genistein, interferon-$\alpha$, interleukin-12, interleukin-18, itraconazole, linomide, MMP inhibitors, 2-methoxyestradiol, pigment epithelium-derived factor (PEDF), platelet factor-4, PPAR-$\alpha$ agonists (e.g., fibrates), PPAR-$\gamma$ agonists (e.g., thiazolidinediones), prolactin, anti-angiogenic siRNA, sphingosine-1-phosphate inhibitors (e.g., sonepcizumab), squalene, staurosporine, angiostatic steroids (e.g., tetrahydrocortisol) plus heparin, stilbenoids, suramin, SU5416, tasquinimod, tecogalan, tetrathiomolybdate, thalidomide and derivatives thereof (e.g., lenalidomide and pomalidomide), thiabendazole, thrombospondins (e.g., thrombospondin 1), TNP-470, tranilast, Withaferin A, and analogs, derivatives, fragments and salts thereof.

One or more anti-angiogenic agents can be administered at an appropriate time to prevent or reduce the risk of developing pathologies that can lead to severe vision loss. In certain embodiments, one or more anti-angiogenic agents are administered prior to occurrence of scar formation (fibrosis) or a substantial amount thereof.

The anti-angiogenic agents described herein may have additional beneficial properties. For example, the anti-PDGF aptamer E10030 may also have an antifibrotic effect by reducing subretinal fibrosis, which can lead to central vision loss in about 10-15% of people with neovascular AMD.

In some embodiments, two or more anti-angiogenic agents targeting different mechanisms of angiogenesis are used to inhibit neovascularization (including types 1, 2 and 3), decrease the permeability/leakage of blood vessels and treat neovascular AMD. In certain embodiments, the two or more anti-angiogenic agents comprise an anti-VEGF/VEGFR agent (e.g., aflibercept, bevacizumab or ranibizumab) and an agent targeting a different mechanism of angiogenesis. In some embodiments, the two or more anti-angiogenic agents comprise an anti-VEGF/VEGFR agent and an anti-PDGF/PDGFR agent, such as bevacizumab or ranibizumab and E10030, or aflibercept and REGN2176-3. E10030 blocks PDGF-B from binding to its natural receptor on pericytes, causing pericytes to be stripped from newly formed abnormal blood vessels. Left unprotected, the endothelial cells are highly vulnerable to the effects of an anti-VEGF agent. Because of this ability to strip pericytes, E10030 may have an effect on both immature blood vessels and more mature blood vessels slightly later in the disease process. In further embodiments, the two or more anti-angiogenic agents comprise an anti-VEGF/VEGFR agent and an anti-angiopoietin/angiopoietin receptor agent, such as aflibercept and nesvacumab or REGN910-3.

Alternatively, an anti-angiogenic agent targeting different mechanisms of angiogenesis can be employed to treat, e.g., neovascular AMD. For example, a bispecific antibody or DARPin targeting VEGF/VEGFR and PDGF/PDGFR, or a bispecific antibody or DARPin targeting VEGF/VEGFR and angiopoietin/angiopoietin receptor, can be used.

AMD can also be treated with other kinds of therapy, including laser photocoagulation therapy (LPT), photodynamic therapy (PDT) and radiation therapy (RT). LPT employs, e.g., an argon (Ar) laser, a micropulse laser or a nanosecond laser, or any combination thereof, and can reduce or eliminate drusen in patients with atrophic AMD or neovascular AMD. Laser surgery can also be employed to destroy abnormal blood vessels in the eye and generally is suitable if the growth of abnormal blood vessels is not too extensive and the abnormal blood vessels are not close to the fovea. PDT utilizes a laser in combination with a compound (e.g., verteporfin) that, upon activation by light of a particular wavelength, injures target cells and not normal cells. A steroid can optionally be administered in PDT. PDT is often employed to treat polypoidal neovasculopathy, the most common form of neovascularization in Asian populations. Examples of RT include without limitation external beam irradiation, focal radiation (e.g., via intravitreal, transvitreal or transpupillary delivery) (e.g., transvitreal delivery of strontium 90 [$^{90}$Sr] X-ray at 15 Gy or 24 Gy doses), and radiation in combination with an anti-VEGF/VEGFR agent (e.g., transvitreal delivery of $^{90}$Sr X-ray at a single 24 Gy dose combined with bevacizumab, or 16 Gy X-ray combined with ranibizumab). PDT or RT can be provided to reduce neovascularization (e.g., CNV) and limit vision loss or improve visual acuity in patients with neovascular AMD. In some embodiments, LPT, PDT or RT, or any combination or all thereof, is provided to a patient with neovascular AMD who does not respond adequately to treatment with an anti-angiogenic agent (e.g., an anti-VEGF/VEGFR agent).

Furthermore, cell replacement therapies and stem cell-based therapies, such as stem cell-derived retinal pigment epithelium (RPE) cells, can be employed to treat AMD. As an illustrative example, an apolipoprotein mimetic [e.g., an apoA-I mimetic (e.g., L-4F) and/or an apoE mimetic (e.g., AEM-28-14)] can be used in combination with RPE cell replacement to treat, e.g., advanced-stage AMD, including central geographic atrophy and neovascular AMD. RPE cells may atrophy and die as a result of rampant lipid deposition in the sub-RPE-BL space and over the BrM. Removal of lipid deposits from the sub-RPE-BL space and the BrM normalizes the BrM structure and function and improves the transport of incoming micronutrients (including vitamin A) and outgoing waste between the choriocapillaris and the RPE and thereby improves the health of RPE cells. Therefore, an advanced-stage AMD patient can first be treated with a lipid-clearing apo mimetic [e.g., an apoA-I mimetic (e.g., L-4F) and/or an apoE mimetic (e.g., AEM-28-14)] and then receive RPE cell replacement (e.g., via one or more injections into or implantations in, e.g., the space below the retina). The RPE cells can be, e.g., RPE cells derived from stem cells (e.g., human embryonic stem cells [hESC], human neural stem cells [hNSC], bone marrow stem cells and induced pluripotent stem cells [iPSC], including autologous stem cells) or RPE cells obtained from the translocation of full-thickness retina. Removal of lipid deposits in the eye by the apo mimetic can lead to beneficial effects such as curtailment of local inflammation, oxidative stress and complement activation, which can aid in preventing or forestalling RPE cell atrophy and death.

As an example of an RPE cell replacement therapy, RPE cells can be introduced as a sheet on a polymer or other suitable carrier material that allows the cells to interdigitate with remaining photoreceptors and to resume vital phagocytosis and vitamin A transfer functions, among other functions. A lipid-clearing apo mimetic [e.g., an apoA-I mimetic (e.g., L-4F) and/or an apoE mimetic (e.g., AEM-28-14)] improves traffic of incoming nutrients and outgoing waste across the BrM and thereby improves the health of cells in the surrounding area. Optionally in combination with an agent (e.g., a matrix metalloproteinase) that reduces the thickness of basal laminar deposits (BLamD) persisting over the BrM, the apo mimetic aids in the preparation of a suitable transplant bed for the sheet of RPE cells, which benefit from a clear path from the choriocapillaris to the transplant scaffolding.

As another example of an RPE cell replacement therapy, cells can be introduced into the eye by a non-surgical method. Bone marrow cells can be re-programmed to home in on the RPE layer and to take up residence among the native RPE cells. An apo mimetic [e.g., an apoA-I mimetic (e.g., L-4F) and/or an apoE mimetic (e.g., AEM-28-14)], optionally in combination with an agent (e.g., a matrix metalloproteinase) that reduces the thickness of BLamD persisting over the BrM, increases the transport of incoming nutrients and outgoing waste across the BrM and thereby improves the health of cells in the RPE layer.

RPE rejuvenation can also be practiced. For example, free-floating cells (e.g., umbilical cells) can be injected to provide trophic support to existing cells (e.g., neuronal and RPE cells). A lipid-clearing apo mimetic [e.g., an apoA-I mimetic (e.g., L-4F) and/or an apoE mimetic (e.g., AEM-28-14)] improves traffic of incoming nutrients and outgoing waste across the BrM and thereby improves the health of cells in the area of the choroidal watershed. Optionally in combination with an agent (e.g., a matrix metalloproteinase) that reduces the thickness of BLamD persisting over the BrM, the apo mimetic aids in the preparation of a suitable dispersion bed for the injected cells.

In addition, AMD can be treated by cell replacement therapies for the choriocapillaris. For instance, the choriocapillaris endothelium can be replaced with stem cell-derived choriocapillaris endothelial cells.

Choriocapillaris vascular dropout/loss and reduced choroidal blood flow can occur early in the pathogenesis of AMD. In early AMD, the vascular density of the choriocapillaris is inversely correlated with the density of sub-RPE-BL deposits (e.g., drusen and BLinD), and the number of "ghost" vessels (remnants of previously healthy capillaries) is positively correlated with sub-RPE-BL deposit density. Vascular endothelial-cell loss may result from activation of the complement system and formation of MACs in the choriocapillaris, which can be inhibited by the use of a complement inhibitor (e.g., an inhibitor of MAC formation, deposition or function). Endothelial dysfunction may also be caused by: 1) a diminished amount of nitric oxide, which can be due to a high level of dimethylarginine (which interferes with L-arginine-stimulated nitric oxide synthesis) and can be corrected by the use of an agent that increases the level of nitric oxide (e.g., a stimulator of nitric oxide synthesis or an inhibitor of dimethylarginine formation; 2) an increase in reactive oxygen species, which can impair nitric oxide synthesis and activity and can be inhibited by the use of an antioxidant (e.g., a scavenger of reactive oxygen species); and 3) inflammatory events, which can be inhibited by an agent that inhibits endothelial inflammatory events (e.g., an apoA-I mimetic such as Rev-D-4F). Reduced choroidal blood flow (CBF) can be improved by using an agent that increases CBF, such as a CBF facilitator (e.g., MC-1101) or a vasodilator (e.g., hyperpolarization-mediated [calcium channel blocker, e.g., adenosine], cAMP-mediated [e.g., prostacyclin], cGMP-mediated [e.g., nitric oxide], inhibition of a phosphodiesterase [PDE] [e.g., moxaverine or sildenafil {a PDE5 inhibitor}], or inhibition of complement polypeptides that cause smooth muscle contraction [e.g., C3a, C4a and C5a]). Increasing CBF can prevent rupture of the BrM. To treat vascular loss and/or decreased CBF, one or more therapeutic agents that preserve or improve the health of the endothelium and/or the blood flow of the vascular system of the eye, including the therapeutic agents described herein, can be administered at least in early AMD.

In some embodiments, an apolipoprotein mimetic (e.g., an apoA-I mimetic [e.g., L-4F] and/or an apoE mimetic [e.g., AEM-28-14]) is used in conjunction with one or more additional therapeutic agents to treat AMD. In certain embodiments, the apo mimetic and the one or more additional therapeutic agents have a synergistic effect.

VI. Treatment of AMD with an Apoliprotein Mimetic and an Anti-Angiogenic Agent Some embodiments of the disclosure relate to a method of treating AMD, comprising administering to a subject in need of treatment a therapeutically effective amount of an apolipoprotein (apo) mimetic and a therapeutically effective amount of an anti-angiogenic agent, whether or not the apo mimetic is administered locally to, into, in or around the eye in a dose from about 0.1 or 0.3 mg to about 1.5 mg per administration (e.g., per injection), or in a total dose from about 0.5 or 1 mg to about 10 mg over a period of about 6 months. All of the embodiments relating to the treatment of AMD with an apolipoprotein mimetic which are described in Section IV and elsewhere herein also apply to the treatment of AMD with an apo mimetic and an anti-angiogenic agent.

Examples of apolipoprotein mimetics, including apoA-I mimetics and apoE mimetics, include without limitation those described elsewhere herein. In some embodiments, the apo mimetic includes, or is, an apoA-I mimetic. In certain embodiments, the apoA-I mimetic includes, or is, 4F or a variant or salt (e.g., acetate salt) thereof. In some embodiments, all of the amino acid residues of 4F have the L-form (L-4F). In other embodiments, one or more, or all, of the amino acid residues of 4F have the D-form (e.g., D-4F having all D-amino acid residues). 4F can have a protecting group at the N-terminus (e.g., an acyl group, such as an acetyl group) and/or the C-terminus (e.g., an amide group, such as —C(O)NH$_2$). In certain embodiments, the apoA-I mimetic includes, or is, L-4F having the structure Ac-DWFKAFYDKVAEKFKEAF-NH$_2$ (SEQ. ID. NO. 13). In further embodiments, the apo mimetic includes, or is, an apoE mimetic. In certain embodiments, the apoE mimetic includes, or is, AEM-28-14 or a variant or salt thereof.

Examples of anti-angiogenic agents include without limitation those described elsewhere herein. In some embodiments, the anti-angiogenic agent includes, or is, an agent that inhibits the action of a vascular endothelial growth factor (an anti-VEGF agent), including without limitation VEGF-A, VEGF-B and placental growth factor (PGF). Non-limiting examples of anti-VEGF agents include those described elsewhere herein. In certain embodiments, the anti-VEGF agent includes, or is, aflibercept (EYLEA®), bevacizumab (AVASTIN®) or ranibizumab (LUCENTIS®), or any combination or all thereof. In further embodiments, the anti-angiogenic agent includes, or is, an agent that inhibits the action of a platelet-derived growth factor (an anti-PDGF agent), including without limitation PDGF-A, PDGF-B, PDGF-C, PDGF-D and PDGF-A/B. Non-limiting examples of anti-PDGF agents include those described elsewhere herein. In certain embodiments, the anti-PDGF agent includes, or is, E10030 (FOVISTA®).

In some embodiments, the anti-angiogenic agent (e.g., an anti-VEGF agent) is administered in a frequency less than the conventional or recommended dosing frequency, and/or in a dose less than the conventional or recommended dose, for the anti-angiogenic agent in the absence of treatment with the apo mimetic [e.g., an apoA-I mimetic (e.g., L-4F) and/or an apoE mimetic (e.g., AEM-28-14)], whether or not the apo mimetic is administered locally in a dose from about 0.1 or 0.3 mg to about 1.5 mg per administration (e.g., per injection), or in a total dose from about 0.5 or 1 mg to about 10 mg over a period of about 6 months. In some embodiments, the anti-angiogenic agent (e.g., an anti-VEGF agent) is administered (e.g., by intravitreal injection) at least about 1.5, 2, 3, 4, 5 or 6 (e.g., at least about 2) times less frequently than the conventional or recommended dosing frequency for the anti-angiogenic agent in the absence of treatment with the apo mimetic [e.g., an apoA-I mimetic (e.g., L-4F) and/or an apoE mimetic (e.g., AEM-28-14)]. In certain embodiments, the anti-angiogenic agent (e.g., an anti-VEGF agent) is administered locally to, into, in or around the eye (e.g., by intravitreal injection) once every 2, 3, 4, 5 or 6 months. In further embodiments, treatment with the apo mimetic [e.g., an apoA-I mimetic (e.g., L-4F) and/or an apoE mimetic (e.g., AEM-28-14)] reduces the total number of times (e.g., the total number of injections) the anti-angiogenic agent (e.g., an anti-VEGF agent) is administered. In certain embodiments, the anti-angiogenic agent (e.g., an anti-VEGF agent) is administered (e.g., by intravitreal injection) no more than about 20, 18, 15, 12 or 10 times. In additional embodiments, the anti-angiogenic agent (e.g., an anti-VEGF agent) is administered (e.g., by intravitreal injection) in a dose at least about 10%, 20%, 30%, 40%, 50%, 60%, 70% or 80% (e.g., at least about 20%), or about 10-30%, 30-50% or 50-70%, less than the conventional or recommended dose for the anti-angiogenic agent in the absence of treatment with the apo mimetic [e.g., an apoA-I mimetic (e.g., L-4F) and/or an apoE mimetic (e.g., AEM-28-14)].

Treatment of AMD with the apo mimetic [e.g., an apoA-I mimetic (e.g., L-4F) and/or an apoE mimetic (e.g., AEM-28-14)] and the anti-angiogenic agent (e.g., an anti-VEGF agent) may have a synergistic effect. For instance, treatment with the apo mimetic (e.g., an apoA-I mimetic and/or an apoE mimetic) may enhance the efficacy of the anti-angiogenic agent, and/or vice versa. As an example, L-4F can markedly reduce lipid deposits from the Bruch's membrane (BrM) and structurally remodel the BrM to a normal or healthier state, thereby reducing the susceptibility of the BrM to penetration by new blood vessels growing from the choroid through the BrM and into the sub-RPE-BL space and the subretinal space in types 1 and 2 neovascularization (NV). As another example, the ability of L-4F to reduce inflammation (via inhibition of, e.g., activation of the complement system and the formation of pro-inflammatory oxidized lipids), an important stimulus of NV, can decrease the required number of administrations (e.g., by injection) and/or dosage of the anti-angiogenic agent. Synergism between the apo mimetic (e.g., an apoA-I mimetic and/or an apoE mimetic) and the anti-angiogenic agent can allow, but is not required for, e.g., the anti-angiogenic agent to be administered less frequently than the conventional or recommended dosing frequency, and/or in a dose lower than the conventional or recommended dose, for the anti-angiogenic agent in the absence of treatment with the apo mimetic (e.g., an apoA-I mimetic and/or an apoE mimetic).

Administration of a lower dose of the anti-angiogenic agent can have benefits, such as a better safety profile due to fewer side effects. Less frequent administration (e.g., by intravitreal injection) of the anti-angiogenic agent can also have benefits, such as greater/better patient comfort, convenience, compliance and health due to fewer invasive procedures being performed. Frequent administration can tax both the care provider and the patient because of frequent office visits for testing, monitoring and treatment. Furthermore, the anti-angiogenic agent (e.g., an anti-VEGF agent) may become less effective with repeated use, a phenomenon known as tachyphylaxis. Moreover, risks of intravitreal injections include elevated intraocular pressure, bacterial and sterile endophthalmitis, cataract formation, hemorrhage and retinal detachment, and repeated injections can lead to retinal thinning and geographic atrophy.

In certain embodiments, the anti-angiogenic agent includes, or is, aflibercept (EYLEA®), and aflibercept is administered (e.g., by intravitreal injection) in a dose of about 1-1.5 mg or 1.5-2 mg once every 3, 4, 5 or 6 months, optionally after being administered in a dose of about 1-1.5 mg or 1.5-2 mg once every month for the first 1, 2 or 3 months or once every 6 weeks for the first 1.5 or 3 months, compared to the conventional or recommended dose and dosing frequency for aflibercept of 2 mg administered by intravitreal injection once every 2 months after administration of 2 mg once every month for the first 3 months in the absence of treatment with the apo mimetic [e.g., an apoA-I mimetic (e.g., L-4F) and/or an apoE mimetic (e.g., AEM-28-14)]. The intravitreal half-life of aflibercept has been estimated to be about 9.0 days.

In other embodiments, the anti-angiogenic agent includes, or is, aflibercept, and aflibercept is administered (e.g., by intravitreal injection) in a dose of about 1-1.25 mg, 1.25-1.5 mg or 1.5-1.75 mg in a frequency substantially similar to or the same as the conventional or recommended dosing frequency for aflibercept in the absence of treatment with the apo mimetic [e.g., an apoA-I mimetic (e.g., L-4F) and/or an apoE mimetic (e.g., AEM-28-14)].

In further embodiments, the anti-angiogenic agent includes, or is, ranibizumab (LUCENTIS®), and ranibizumab is administered (e.g., by intravitreal injection) in a dose of about 0.2-0.3 mg, 0.3-0.4 mg or 0.4-0.5 mg once every 2, 3, 4, 5 or 6 months, optionally after being administered in a dose of about 0.2-0.3 mg, 0.3-0.4 mg or 0.4-0.5 mg once every month for the first 1, 2 or 3 months or once every 6 weeks for the first 1.5 or 3 months, compared to the conventional or recommended dose and dosing frequency for ranibizumab of 0.5 mg administered by intravitreal injection once every month in the absence of treatment with the apo mimetic [e.g., an apoA-I mimetic (e.g., L-4F) and/or an apoE mimetic (e.g., AEM-28-14)]. The intravitreal half-life of ranibizumab has been estimated to be about 7.1 days.

In other embodiments, the anti-angiogenic agent includes, or is, ranibizumab, and ranibizumab is administered (e.g., by intravitreal injection) in a dose of about 0.2-0.3 mg or 0.3-0.4 mg once every month.

In additional embodiments, the anti-angiogenic agent includes, or is, bevacizumab (AVASTIN®), and bevacizumab is administered (e.g., by intravitreal injection) in a dose of about 0.5-0.75 mg, 0.75-1 mg or 1-1.25 mg once every 2, 3, 4, 5 or 6 months, optionally after being administered in a dose of about 0.5-0.75 mg, 0.75-1 mg or 1-1.25 mg once every month for the first 1, 2 or 3 months or once every 6 weeks for the first 1.5 or 3 months, compared to the conventional or recommended dose and dosing frequency for bevacizumab for the treatment of AMD of about 1.25 mg administered by intravitreal injection once every month in the absence of treatment with the apo mimetic [e.g., an apoA-I mimetic (e.g., L-4F) and/or an apoE mimetic (e.g., AEM-28-14)]. The intravitreal half-life of bevacizumab has been estimated to be about 9.8 days.

In other embodiments, the anti-angiogenic agent includes, or is, bevacizumab, and bevacizumab is administered (e.g., by intravitreal injection) in a dose of about 0.5-0.75 mg or 0.75-1 mg once every month.

In some embodiments, the duration/length of treatment with the anti-angiogenic agent (e.g., an anti-VEGF agent) is no more than about 36, 30, 24, 18 or 12 months. In certain embodiments, the length of treatment with the anti-angiogenic agent (e.g., an anti-VEGF agent) is no more than about 24, 18 or 12 months. In further embodiments, the length of treatment with the anti-angiogenic agent (e.g., an anti-VEGF agent) is about 6-12, 12-18 or 18-24 months.

In some embodiments, the anti-angiogenic agent (e.g., an anti-VEGF agent) is administered to treat or slow the progression of neovascular (wet) AMD, including types 1, 2 and 3 neovascularization (NV) and including when signs of active neovascularization are present. The presence of sub-RPE-BL, subretinal or intraretinal fluid, which can signify active neovascularization and leakage of fluid from new blood vessels, can be detected by techniques such as OCT-fluorescein angiography. In certain embodiments, the anti-angiogenic agent (e.g., an anti-VEGF agent) is administered when the presence of subretinal or intraretinal fluid is detected. An anti-angiogenic agent (e.g., an anti-VEGF agent) can also be employed when sub-RPE-BL fluid is detected, although pigment epithelium detachment caused by sub-RPE-BL fluid can remain stable for a relatively long time and may not require anti-angiogenic therapy. In further embodiments, the anti-angiogenic agent (e.g., an anti-VEGF agent) is administered at least in the advanced stage of AMD to prevent, delay the onset of, or slow the progression to neovascular AMD. In certain embodiments, the anti-angiogenic agent (e.g., an anti-VEGF agent) is administered (e.g., by intravitreal injection) less frequently, and/or in a lower dose, to prevent, delay the onset of, or slow the progression to neovascular AMD than to treat or slow the progression of neovascular AMD.

Regarding the apo mimetic, in certain embodiments the apo mimetic [e.g., an apoA-I mimetic (e.g., L-4F) and/or an apoE mimetic (e.g., AEM-28-14)] is administered locally to, into, in or around the eye (e.g., by intravitreal injection) in a dose of about 0.1 or 0.3-1.5 mg, 0.1-0.5 mg, 0.5-1 mg, 1-1.5 mg, 0.1-0.3 mg, 0.3-0.5 mg, 0.5-0.75 mg, 0.75-1 mg, 1-1.25 mg or 1.25-1.5 mg (e.g., about 0.1-0.5 mg or 0.5-1 mg) per administration (e.g., per injection). The apo mimetic can also be administered locally in a dose greater than 1.5 mg per administration, such as up to about 2 mg or more per administration (e.g., per injection). In further embodiments, the apo mimetic [e.g., an apoA-I mimetic (e.g., L-4F) and/or an apoE mimetic (e.g., AEM-28-14)] is administered locally (e.g., by intravitreal injection or via a sustained-release composition) in a total dose of about 0.5 or 1-10 mg, 0.5 or 1-5 mg, 5-10 mg, 0.5 or 1-3 mg, 3-5 mg, 5-7.5 mg or 7.5-10 mg (e.g., about 0.5-3 mg or 3-5 mg) over a period of about 6 months, where the duration/length of treatment with the apo mimetic can be, e.g., about 6-12, 12-18 or 18-24 months or longer. The apo mimetic can also be administered locally in a total dose greater than 10 mg over a period of about 6 months, such as up to about 15 mg or more over a period of about 6 months. In yet further embodiments, the apo mimetic [e.g., an apoA-I mimetic (e.g., L-4F) and/or an apoE mimetic (e.g., AEM-28-14)] is administered locally in a total dose of about 1 or 2-20 mg, 5-15 mg, 1-5 mg, 5-10 mg, 10-15 mg, 15-20 mg, 1-3 mg, 3-5 mg, 5-7.5 mg, 7.5-10 mg, 10-12.5 mg, 12.5-15 mg, 15-17.5 mg or 17.5-20 mg (e.g., about 1-5 mg or 5-10 mg) for the whole/entire treatment regimen with the apo mimetic. The apo mimetic can also be administered locally in a total dose greater than 20 mg for the entire treatment regimen, such as up to about 25 mg, 30 mg, 40 mg, 50 mg or more for the entire treatment regimen.

In embodiments where the apo mimetic [e.g., an apoA-I mimetic (e.g., L-4F) and/or an apoE mimetic (e.g., AEM-28-14)] is administered locally to, into, in or around the eye, the dose per administration, the total dose over a period of about 6 months, and the total dose for the whole treatment regimen are per administered eye in certain embodiments and for both eyes in other embodiments. The blood system may allow some amount (e.g., a therapeutically effective amount) of the apo mimetic locally administered (e.g., injected) into or in one eye to be distributed to the other eye, in which case the dose of the apo mimetic can optionally be adjusted (e.g., increased) to take into account the other eye (which may be in a less diseased condition), and which may allow both eyes to be treated with the apo mimetic at the same time without an additional administration (e.g., injection) of the apo mimetic into or in the other eye. For example, an intravitreally injected apo mimetic can cross the blood-retinal barrier to reach two of the target areas, the sub-RPE-BL space and the Bruch's membrane, from where the apo mimetic may enter the choriocapillaris and ultimately the fellow non-administered eye. Also without intending to be bound by theory, some amount of the apo mimetic may enter the fellow non-administered eye by way of the aqueous humor, which drains via the trabecular meshwork and Schlemm's canal that flows into the blood system. Accordingly, some embodiments relate to a method of treating AMD, comprising administering to a subject in need of treatment a therapeutically effective amount of an apo mimetic and a therapeutically effective amount of an anti-angiogenic agent, wherein the apo mimetic is administered locally to, into, in or around one eye and has a therapeutic effect in both eyes.

In additional embodiments, the apo mimetic [e.g., an apoA-I mimetic (e.g., L-4F) and/or an apoE mimetic (e.g., AEM-28-14)] is administered locally (e.g., by intravitreal injection) once every month (4 weeks) or 1.5 months (6 weeks). In other embodiments, the apo mimetic [e.g., an apoA-I mimetic (e.g., L-4F) and/or an apoE mimetic (e.g., AEM-28-14)] is administered locally (e.g., by intravitreal injection) once every 2 months (8 weeks), 2.5 months (10 weeks) or 3 months (12 weeks). In still other embodiments, the apo mimetic [e.g., an apoA-I mimetic (e.g., L-4F) and/or an apoE mimetic (e.g., AEM-28-14)] is administered locally (e.g., by intravitreal injection or via a sustained-release composition) once every 4, 5 or 6 months. In further embodiments, the apo mimetic [e.g., an apoA-I mimetic (e.g., L-4F) and/or an apoE mimetic (e.g., AEM-28-14)] is administered locally in a total of about 15 or less, 12 or less, 9 or less, 6 or less, or 3 or less (e.g., 3-6 or 7-10) administrations (e.g., injections). The apo mimetic can also be administered locally in a total of more than 15 administrations (e.g., injections), such as up to about 20 or more administrations (e.g., injections). In embodiments where the apo mimetic is administered locally to, into, in or around the eye, the frequency of administration and the total number of administrations (e.g., injections) are per administered eye in certain embodiments and for both eyes in other embodiments, as the apo mimetic may also have a therapeutic effect in the fellow non-administered eye.

In some embodiments, the apo mimetic [e.g., an apoA-I mimetic (e.g., L-4F) and/or an apoE mimetic (e.g., AEM-28-14)] is administered at least in the advanced stage of AMD to treat or slow the progression of neovascular AMD, including types 1, 2 and 3 NV. In further embodiments, the apo mimetic [e.g., an apoA-I mimetic (e.g., L-4F) and/or an apoE mimetic (e.g., AEM-28-14)] is administered at least in the advanced stage of AMD to treat or slow the progression of central geographic atrophy (GA), and/or to prevent or delay the onset of neovascular AMD. In additional embodiments, the apo mimetic [e.g., an apoA-I mimetic (e.g., L-4F) and/or an apoE mimetic (e.g., AEM-28-14)] is administered at least in the intermediate stage of AMD to treat or slow the progression of non-central GA, and/or to prevent or delay the onset of central GA and/or neovascular AMD.

In some embodiments, the apo mimetic [e.g., an apoA-I mimetic (e.g., L-4F) and/or an apoE mimetic (e.g., AEM-28-14)], and/or the anti-angiogenic agent (e.g., an anti-VEGF agent), are administered locally to, into, in or around the eye. Potential routes, sites and means of local administration are described elsewherein herein. In some embodiments, the apo mimetic [e.g., an apoA-I mimetic (e.g., L-4F) and/or an apoE mimetic (e.g., AEM-28-14)], and/or the anti-angiogenic agent (e.g., an anti-VEGF agent), are administered by injection (e.g., intravitreal, subconjunctival, subretinal or sub-Tenon's injection), eye drop or implant (e.g., intravitreal, subretinal or sub-Tenon's implant). In certain embodiments, the apo mimetic [e.g., an apoA-I mimetic (e.g., L-4F) and/or an apoE mimetic (e.g., AEM-28-14)] and the anti-angiogenic agent (e.g., an anti-VEGF agent) are administered by injection (e.g., intravitreal, subconjunctival, subretinal or sub-Tenon's injection). In further embodiments, the apo mimetic [e.g., an apoA-I mimetic (e.g., L-4F) and/or an apoE mimetic (e.g., AEM-28-14)], and/or the anti-angiogenic agent (e.g., an anti-VEGF agent), are administered via a sustained-release composition. Non-limiting examples of sustained-release compositions include those described elsewhere herein.

In certain embodiments, the apo mimetic [e.g., an apoA-I mimetic (e.g., L-4F) and/or an apoE mimetic (e.g., AEM-28-14)] is administered locally to, into, in or around the eye in the early phase of treatment, and then the apo mimetic is administered systemically. As a non-limiting example, the initial administration(s) (e.g., the first one to five administrations) of the apo mimetic can be local via injection (e.g., intravitreal, subconjunctival, subretinal or sub-Tenon's injection), and then subsequent administration(s) of the apo mimetic can be systemic, such as oral, parenteral (e.g., subcutaneous, intramuscular or intravenous), or topical (e.g., intranasal or pulmonary). In other embodiments, the apo mimetic is administered only locally. In yet other embodiments, the apo mimetic is administered only systemically.

The apo mimetic [e.g., an apoA-I mimetic (e.g., L-4F or a variant or salt thereof) and/or an apoE mimetic (e.g., AEM-28-14 or a variant or salt thereof)] and the anti-angiogenic agent (e.g., an anti-VEGF agent, such as aflibercept, bevacizumab and/or ranibizumab) can be administered via the same pharmaceutical composition or separate pharmaceutical compositions, where a composition further comprises one or more pharmaceutically acceptable excipients or carriers. If the apo mimetic (e.g., an apoA-I mimetic and/or an apoE mimetic) and the anti-angiogenic agent are administered via the same composition, such a composition can be prepared in advance or can be prepared by combining the apo mimetic and the anti-angiogenic agent into the same formulation shortly or just before the formulation is administered (e.g., by injection). Administration of the apo mimetic (e.g., an apoA-I mimetic and/or an apoE mimetic) and the anti-angiogenic agent in the same composition decreases the number of times the patient is subjected to a potentially invasive procedure (e.g., intravitreal injection) compared to separate administration of the therapeutic agents, which can have benefits such as improved patient compliance and health due to fewer invasive procedures being performed.

In certain embodiments, the composition containing the apo mimetic [e.g., an apoA-I mimetic (e.g., L-4F) and/or an apoE mimetic (e.g., AEM-28-14)], whether or not it contains the anti-angiogenic agent (e.g., an anti-VEGF agent), comprises about 75-95% (e.g., about 90%) of the apo mimetic(s) and about 5-25% (e.g., about 10%) of the corresponding apolipoprotein(s) (e.g., apoA-I and/or apoE) or an active portion or domain thereof by weight or molarity relative to their combined amount.

In some embodiments, the composition containing the apo mimetic [e.g., an apoA-I mimetic (e.g., L-4F) and/or an apoE mimetic (e.g., AEM-28-14)], and/or the composition containing the anti-angiogenic agent (e.g., an anti-VEGF agent), whether the same composition or separate compositions, comprise one or more excipients that inhibit peptide/protein aggregation, increase peptide/protein solubility, reduce solution viscosity or increase peptide/protein stability, or any combination or all thereof. Examples of such excipients include without limitation those described elsewhere herein, and the use of such excipients can have benefits as described elsewhere herein. For instance, such excipients can improve the injectability of a composition, and thus can enable the use of a needle with a smaller gauge for injection. Moreover, the use of such excipients can decrease the volume needed to administer a given amount of a peptide or protein, and hence can reduce ocular pressure if the peptide or protein is administered by injection into the eye. In addition, the use of such excipients can allow a greater dose of a peptide or protein to be administered for a given volume, which can permit the peptide or protein to be administered less frequently for a given total dose administered over a time period.

In some embodiments, the anti-angiogenic agent (e.g., an anti-VEGF agent) is administered (e.g., by intravitreal injection) in a dose higher than the conventional or recommended dose, and in a frequency less than the conventional or recommended dosing frequency, for the anti-angiogenic agent in the absence of treatment with the apo mimetic [e.g., an apoA-I mimetic (e.g., L-4F) and/or an apoE mimetic (e.g., AEM-28-14)]. In certain embodiments, the anti-angiogenic agent (e.g., an anti-VEGF agent) is administered (e.g., by intravitreal injection) in a dose at least about 10%, 20%, 30%, 50%, 75%, 100%, 150% or 200% (e.g., at least about 30%), or about 10-30%, 30-50%, 50-100%, 100-150% or 150-200% (e.g., about 50-100%), higher than the conventional or recommended dose for the anti-angiogenic agent in the absence of treatment with the apo mimetic [e.g., an apoA-I mimetic (e.g., L-4F) and/or an apoE mimetic (e.g., AEM-28-14)]. In further embodiments, the anti-angiogenic agent (e.g., an anti-VEGF agent) is administered (e.g., by intravitreal injection) at least about 1.5, 2, 3, 4, 5 or 6 (e.g., at least about 2) times less frequently than the conventional or recommended dosing frequency for the anti-angiogenic agent in the absence of treatment with the apo mimetic [e.g., an apoA-I mimetic (e.g., L-4F) and/or an apoE mimetic (e.g., AEM-28-14)].

In certain embodiments, the anti-angiogenic agent includes, or is, aflibercept (EYLEA®), and aflibercept is administered (e.g., by intravitreal injection) in a dose of about 2.2-2.5 mg, 2.5-3 mg, 3-3.5 mg or 3.5-4 mg once every 3, 4, 5 or 6 months, optionally after being administered in a dose of about 2.2-2.5 mg, 2.5-3 mg, 3-3.5 mg or 3.5-4 mg once every month for the first 1, 2 or 3 months or once every 6 weeks for the first 1.5 or 3 months, compared to the conventional or recommended dose and dosing frequency for aflibercept of 2 mg administered by intravitreal injection once every 2 months after administration of 2 mg once every month for the first 3 months in the absence of treatment with the apo mimetic [e.g., an apoA-I mimetic (e.g., L-4F) and/or an apoE mimetic (e.g., AEM-28-14)].

In other embodiments, the anti-angiogenic agent includes, or is, ranibizumab (LUCENTIS®), and ranibizumab is administered (e.g., by intravitreal injection) in a dose of about 0.55-0.75 mg, 0.75-1 mg, 1-1.25 mg or 1.25-1.5 mg once every 2, 3, 4, 5 or 6 months, optionally after being administered in a dose of about 0.55-0.75 mg, 0.75-1 mg, 1-1.25 mg or 1.25-1.5 mg once every month for the first 1, 2 or 3 months or once every 6 weeks for the first 1.5 or 3 months, compared to the conventional or recommended dose and dosing frequency for ranibizumab of 0.5 mg administered by intravitreal injection once every month in the absence of treatment with the apo mimetic [e.g., an apoA-I mimetic (e.g., L-4F) and/or an apoE mimetic (e.g., AEM-28-14)].

In yet other embodiments, the anti-angiogenic agent includes, or is, bevacizumab (AVASTIN®), and bevacizumab is administered (e.g., by intravitreal injection) in a dose of about 1.4-1.75 mg, 1.75-2 mg, 2-2.5 mg or 2.5-3 mg once every 2, 3, 4, 5 or 6 months, optionally after being administered in a dose of about 1.4-1.75 mg, 1.75-2 mg, 2-2.5 mg or 2.5-3 mg once every month for the first 1, 2 or 3 months or once every 6 weeks for the first 1.5 or 3 months, compared to the conventional or recommended dose and dosing frequency for bevacizumab for the treatment of AMD of about 1.25 mg administered by intravitreal injection once every month in the absence of treatment with the apo mimetic [e.g., an apoA-I mimetic (e.g., L-4F) and/or an apoE mimetic (e.g., AEM-28-14)].

One or more other therapeutic agents described herein can be used in combination with the apo mimetic [e.g., an apoA-I mimetic (e.g., L-4F) and/or an apoE mimetic (e.g., AEM-28-14)] and the anti-angiogenic agent (e.g., an anti-VEGF agent) for the treatment of AMD. In some embodiments, the additional therapeutic agent(s) include, or are, an anti-dyslipidemic agent (e.g., a statin, such as atorvastatin), an antioxidant (e.g., vitamins, saffron carotenoids and/or zinc) or a complement inhibitor (e.g., a C5 inhibitor such as ARC1905 or LFG316, or a complement factor D inhibitor such as lampalizumab), or any combination or all thereof. Use of the apo mimetic [e.g., an apoA-I mimetic (e.g., L-4F) and/or an apoE mimetic (e.g., AEM-28-14)] may enhance the efficacy of one or more other therapeutic agents that, e.g., improve altered lipid homeostasis, reduce oxidative stress and/or reduce inflammation. In certain embodiments, the additional therapeutic agent includes, or is, ARC1905 or LFG316.

In some embodiments, the apo mimetic [e.g., an apoA-I mimetic (e.g., L-4F) and/or an apoE mimetic (e.g., AEM-28-14)] and the anti-angiogenic agent (e.g., an anti-VEGF agent) are used in conjunction with an anti-inflammatory agent (e.g., an NSAID such as bromfenac, and/or a corticosteroid such as triamcinolone acetonide) or an immunosuppressant (e.g., an IL-2 inhibitor such as daclizumab or rapamycin, or a TNF-α inhibitor such as infliximab) to treat neovascular AMD. Inflammation is a stimulus of NV, and hence an anti-inflammatory agent or an immunosuppressant can suppress NV. Therefore, use of an anti-inflammatory agent or an immunosuppressant can reduce the number or frequency of administration (e.g., injections) of the anti-angiogenic agent. In further embodiments, the apo mimetic [e.g., an apoA-I mimetic (e.g., L-4F) and/or an apoE mimetic (e.g., AEM-28-14)] and the anti-angiogenic agent (e.g., an anti-VEGF agent) are used in combination with a neuroprotector (e.g., an endogenous neuroprotector, such as CNTF). Use of a neuroprotector can prevent or curtail degeneration of retinal cells (e.g., photoreceptors).

In some embodiments, the additional therapeutic agent(s) are administered at least in the advanced stage of AMD. In further embodiments, the additional therapeutic agent(s) are administered at least in the intermediate stage of AMD. In still further embodiments, the additional therapeutic agent(s) are administered at least in the early stage of AMD. In certain embodiments, the additional therapeutic agent(s) administered at least in the early stage of AMD include, or are, an anti-dyslipidemic agent that reduces lipid production (e.g., a statin), and optionally an antioxidant (e.g., a vitamin, a saffron carotenoid and/or zinc) and/or an anti-inflammatory agent (e.g., an NSAID), and the additional therapeutic agent(s) are administered systemically (e.g., orally) or locally (e.g., by eye drop).

An apo mimetic [e.g., an apoA-I mimetic (e.g., L-4F) and/or an apoE mimetic (e.g., AEM-28-14)] in combination with an anti-angiogenic agent (e.g., an anti-VEGF agent such as aflibercept, bevacizumab or ranibizumab, and/or an anti-PDGF agent such as E10030) can also be used to treat other eye diseases and disorders in addition to AMD. Non-limiting examples of other eye diseases and disorders that can be treated with such a combination include diabetic maculopathy (DMP) (including partial ischemic DMP), diabetic macular edema (DME) (including clinically significant DME [CSME], focal DME and diffuse DME), diabetic retinopathy (including in patients with DME), retinal vein occlusion (RVO), central RVO (including central RVO with cystoid macular edema [CME]), branch RVO (including branch RVO with CME), macular edema following RVO (including central RVO and branch RVO), Irvine-Gass Syndrome (postoperative macular edema), and uveitis (including uveitis posterior with CME). Beneficial properties of an apo mimetic [e.g., an apoA-I mimetic (e.g., L-4F) and/or an apoE mimetic (e.g., AEM-28-14)], such as their strong anti-inflammatory property, can increase the effectiveness of an anti-angiogenic agent (e.g., an anti-VEGF agent) in the treatment of such eye diseases and disorders. Embodiments relating to the treatment of AMD using a combination of an apo mimetic [e.g., an apoA-I mimetic (e.g., L-4F) and/or an apoE mimetic (e.g., AEM-28-14)] and an anti-angiogenic agent (e.g., an anti-VEGF agent) also apply to the treatment of other eye diseases and disorders using such a combination.

VII. Treatment of AMD with an Apoliprotein Mimetic and a Complement Inhibitor Further embodiments of the disclosure relate to a method of treating AMD, comprising administering to a subject in need of treatment a therapeutically effective amount of an apolipoprotein (apo) mimetic and a therapeutically effective amount of a complement inhibitor, whether or not the apo mimetic is administered locally to, into, in or around the eye in a dose from about 0.1 or 0.3 mg to about 1.5 mg per administration (e.g., per injection), or in a total dose from about 0.5 or 1 mg to about 10 mg over a period of about 6 months. All of the embodiments relating to the treatment of AMD with an apolipoprotein mimetic which are described in Section IV and elsewhere herein also apply to the treatment of AMD with an apo mimetic and a complement inhibitor.

Examples of apolipoprotein mimetics, including apoA-I mimetics and apoE mimetics, include without limitation those described elsewhere herein. In some embodiments, the apo mimetic includes, or is, an apoA-I mimetic. In certain embodiments, the apoA-I mimetic includes, or is, 4F or a variant or salt (e.g., acetate salt) thereof. In some embodiments, all of the amino acid residues of 4F have the L-form (L-4F). In other embodiments, one or more, or all, of the amino acid residues of 4F have the D-form (e.g., D-4F having all D-amino acid residues). 4F can have a protecting group at the N-terminus (e.g., an acyl group, such as an acetyl group) and/or the C-terminus (e.g., an amide group, such as —C(O)NH$_2$). In certain embodiments, the apoA-I mimetic includes, or is, L-4F having the structure Ac-DWFKAFYDKVAEKFKEAF-NH$_2$ (SEQ. ID. NO. 13). In further embodiments, the apo mimetic includes, or is, an apoE mimetic. In certain embodiments, the apoE mimetic includes, or is, AEM-28-14 or a variant or salt thereof.

Non-limiting examples of complement inhibitors include those described elsewhere herein. In some embodiments, the complement inhibitor includes, or is, lampalizumab, LFG316 or ARC1905 (ZIMURA®), or any combination or all thereof. In certain embodiments, the complement inhibitor includes, or is, lampalizumab. In some embodiments, the subject has a mutation in the gene encoding complement factor I (CFI), which may be a biomarker for a more positive response to treatment with lampalizumab. CFI, a C3b/C4b inactivator, regulates complement activation by cleaving cell-bound or fluid-phase C3b and C4b.

In some embodiments, the apo mimetic [e.g., an apoA-I mimetic (e.g., L-4F) and/or an apoE mimetic (e.g., AEM-28-14)] and the complement inhibitor (e.g., lampalizumab) are administered to treat geographic atrophy (GA). In some embodiments, the apo mimetic [e.g., an apoA-I mimetic (e.g., L-4F) and/or an apoE mimetic (e.g., AEM-28-14)] and the complement inhibitor (e.g., lampalizumab) are administered to prevent, delay the onset of, or slow the progression of central GA. In certain embodiments, the apo mimetic [e.g., an apoA-I mimetic (e.g., L-4F) and/or an apoE mimetic (e.g., AEM-28-14)] and the complement inhibitor (e.g., lampalizumab) are administered at least in the advanced (late) stage of atrophic (dry) AMD to treat or slow the progression of central GA, and/or to prevent or delay the onset of neovascular AMD. In further embodiments, the apo mimetic [e.g., an apoA-I mimetic (e.g., L-4F) and/or an apoE mimetic (e.g., AEM-28-14)] and the complement inhibitor (e.g., lampalizumab) are administered at least in the intermediate stage of AMD to treat or slow the progression of non-central GA, and/or to prevent or delay the onset of central GA and/or neovascular AMD. In additional embodiments, the apo mimetic [e.g., an apoA-I mimetic (e.g., L-4F) and/or an apoE mimetic (e.g., AEM-28-14)] and the complement inhibitor (e.g., lampalizumab) are administered at least in the early stage of AMD or the initial phase of intermediate AMD to prevent or delay the onset of non-central GA. In certain embodiments, the complement inhibitor (e.g., lampalizumab) and/or the apo mimetic [e.g., an apoA-I mimetic (e.g., L-4F) and/or an apoE mimetic (e.g., AEM-28-14)] are administered less frequently, and/or in a lower dose, to prevent or delay the onset of non-central or central GA than to treat or slow the progression of central GA.

In certain embodiments, treatment with the apo mimetic [e.g., an apoA-I mimetic (e.g., L-4F) and/or an apoE mimetic (e.g., AEM-28-14)] and the complement inhibitor (e.g., lampalizumab) slows the progression of central GA and/or non-central GA (e.g., reduces the rate of GA progression, or reduces the GA lesion area or size) by at least about 10%, 20%, 30%, 40%, 50%, 60%, 70% or 80% (e.g., by at least about 20% or 40%), or by about 20-40%, 40-60% or 60-80%. In further embodiments, treatment with the apo mimetic [e.g., an apoA-I mimetic (e.g., L-4F) and/or an apoE mimetic (e.g., AEM-28-14)] and the complement inhibitor (e.g., lampalizumab) slows the progression of central GA and/or non-central GA (e.g., reduces the rate of GA progression, or reduces the GA lesion area or size) at least about 10%, 20%, 30%, 50%, 100%, 150%, 200% or 300% (e.g., at least about 20% or 30%), or about 10-30%, 30-50%, 50-100%, 100-200% or 200-300% (e.g., about 50-100%), more than treatment with the complement inhibitor in the absence of treatment with the apo mimetic.

Treatment of AMD, including central and non-central GA, with the apo mimetic [e.g., an apoA-I mimetic (e.g., L-4F) and/or an apoE mimetic (e.g., AEM-28-14)] and the complement inhibitor (e.g., lampalizumab) may have a synergistic effect. For instance, treatment with the apo mimetic (e.g., an apoA-I mimetic and/or an apoE mimetic) may enhance the efficacy of the complement inhibitor, and/or vice versa. As an example, L-4F can clear lipid barrier from the Bruch's membrane, which improves the exchange of nutrients (including vitamin A) from the choriocapillaris to RPE cells and photoreceptors, thereby curtailing the death of RPE and photoreceptor cells. As another example, the ability of L-4F to reduce inflammation can decrease the required number of administrations (e.g., by injection) and/or dosage of the complement inhibitor. Synergism between the apo mimetic (e.g., an apoA-I mimetic and/or an apoE mimetic) and the complement inhibitor can allow, but is not required for, e.g., the complement inhibitor to be administered less frequently than the conventional or recommended dosing frequency, and/or in a dose lower than the conventional or recommended dose, for the complement inhibitor in the absence of treatment with the apo mimetic. Administration of a lower dose of the complement inhibitor can have benefits, such as a better safety profile due to fewer side effects. Less frequent administration (e.g., by intravitreal injection) of the complement inhibitor can have significant benefits for the patient as well as the care provider, as described elsewhere herein.

In some embodiments, the complement inhibitor (e.g., lampalizumab) is administered in a frequency less than the conventional or recommended dosing frequency, and/or in a dose less than the conventional or recommended dose, for the complement inhibitor in the absence of treatment with the apo mimetic [e.g., an apoA-I mimetic (e.g., L-4F) and/or an apoE mimetic (e.g., AEM-28-14)], whether or not the apo mimetic is administered locally in a dose from about 0.1 or 0.3 mg to about 1.5 mg per administration (e.g., per injection), or in a total dose from about 0.5 or 1 mg to about 10 mg over a period of about 6 months. In some embodiments, the complement inhibitor (e.g., lampalizumab) is administered (e.g., by intravitreal injection) at least about 1.5, 2, 3, 4, 5 or 6 (e.g., at least about 2) times less frequently than the conventional or recommended dosing frequency for the complement inhibitor in the absence of treatment with the apo mimetic [e.g., an apoA-I mimetic (e.g., L-4F) and/or an apoE mimetic (e.g., AEM-28-14)]. In certain embodiments, the complement inhibitor (e.g., lampalizumab) is administered locally to, into, in or around the eye (e.g., by intravitreal injection) once every 2, 3, 4, 5 or 6 (e.g., once every 2) months. In further embodiments, treatment with the apo mimetic [e.g., an apoA-I mimetic (e.g., L-4F) and/or an apoE mimetic (e.g., AEM-28-14)] reduces the total number of times (e.g., the total number of injections) the complement inhibitor (e.g., lampalizumab) is administered. In certain embodiments, the complement inhibitor (e.g., lampalizumab) is administered locally (e.g., by intravitreal injection) no more than about 20, 18, 15, 12 or 10 times. In additional embodiments, the complement inhibitor (e.g., lampalizumab) is administered (e.g., by intravitreal injection) in a dose at least about 10%, 20%, 30%, 40%, 50%, 60%, 70% or 80% (e.g., at least about 20%), or about 10-30%, 30-50% or 50-70%, less than the conventional or recommended dose for the complement inhibitor in the absence of treatment with the apo mimetic [e.g., an apoA-I mimetic (e.g., L-4F) and/or an apoE mimetic (e.g., AEM-28-14)].

In certain embodiments, the complement inhibitor includes, or is, lampalizumab, and lampalizumab is administered (e.g., by intravitreal injection) in a dose of about 4-6 mg, 6-8 mg or 8-10 mg once every 2, 3, 4, 5 or 6 months, optionally after being administered in a dose of about 4-6 mg, 6-8 mg or 8-10 mg once every month for the first 1, 2 or 3 months or once every 6 weeks for the first 1.5 or 3 months, compared to the conventional or recommended dose and dosing frequency for lampalizumab of about 10 mg administered by intravitreal injection once every month in the absence of treatment with the apo mimetic [e.g., an apoA-I mimetic (e.g., L-4F) and/or an apoE mimetic (e.g., AEM-28-14)].

In other embodiments, the complement inhibitor includes, or is, lampalizumab, and lampalizumab is administered (e.g., by intravitreal injection) in a dose of about 3-5 mg, 5-7 mg or 7-9 mg once every month (4 weeks) or 1.5 months (6 weeks).

In some embodiments, the duration/length of treatment with the complement inhibitor (e.g., lampalizumab) is no more than about 36, 30, 24, 18 or 12 months. In certain embodiments, the length of treatment with the complement inhibitor (e.g., lampalizumab) is no more than about 24, 18 or 12 months. In further embodiments, the length of treatment with the complement inhibitor (e.g., lampalizumab) is about 6-12, 12-18 or 18-24 months.

Regarding the apo mimetic, in certain embodiments the apo mimetic [e.g., an apoA-I mimetic (e.g., L-4F) and/or an apoE mimetic (e.g., AEM-28-14)] is administered locally to, into, in or around the eye (e.g., by intravitreal injection) in a dose of about 0.1 or 0.3-1.5 mg, 0.1-0.5 mg, 0.5-1 mg, 1-1.5 mg, 0.1-0.3 mg, 0.3-0.5 mg, 0.5-0.75 mg, 0.75-1 mg, 1-1.25 mg or 1.25-1.5 mg (e.g., about 0.1-0.5 mg or 0.5-1 mg) per administration (e.g. per injection). The apo mimetic can also be administered locally in a dose greater than 1.5 mg per administration, such as up to about 2 mg or more per administration (e.g., per injection). In further embodiments, the apo mimetic [e.g., an apoA-I mimetic (e.g., L-4F) and/or an apoE mimetic (e.g., AEM-28-14)] is administered locally (e.g., by intravitreal injection or via a sustained-release composition) in a total dose of about 0.5 or 1-10 mg, 0.5 or 1-5 mg, 5-10 mg, 0.5 or 1-3 mg, 3-5 mg, 5-7.5 mg or 7.5-10 mg (e.g., about 0.5-3 mg or 3-5 mg) over a period of about 6 months, where the duration/length of treatment with the apo mimetic can be, e.g., about 6-12, 12-18 or 18-24 months or longer. The apo mimetic can also be administered locally in a total dose greater than 10 mg over a period of about 6 months, such as up to about 15 mg or more over a period of about 6 months. In yet further embodiments, the apo mimetic [e.g., an apoA-I mimetic (e.g., L-4F) and/or an apoE mimetic (e.g., AEM-28-14)] is administered locally in a total dose of about 1 or 2-20 mg, 5-15 mg, 1-5 mg, 5-10 mg, 10-15 mg, 15-20 mg, 1-3 mg, 3-5 mg, 5-7.5 mg, 7.5-10 mg, 10-12.5 mg, 12.5-15 mg, 15-17.5 mg or 17.5-20 mg (e.g., about 1-5 mg or 5-10 mg) for the whole/entire treatment regimen with the apo mimetic. The apo mimetic can also be administered locally in a total dose greater than 20 mg for the entire treatment regimen, such as up to about 25 mg, 30 mg, 40 mg, 50 mg or more for the entire treatment regimen.

In embodiments where the apo mimetic [e.g., an apoA-I mimetic (e.g., L-4F) and/or an apoE mimetic (e.g., AEM-28-14)] is administered locally to, into, in or around the eye, the dose per administration, the total dose over a period of about 6 months, and the total dose for the whole treatment regimen are per administered eye in certain embodiments and for both eyes in other embodiments. The blood system may allow some amount (e.g., a therapeutically effective amount) of the apo mimetic locally administered (e.g., injected) into or in one eye to be distributed to the other eye, in which case the dose of the apo mimetic can optionally be adjusted (e.g., increased) to take into account the other eye (which may be in a less diseased condition), and which may allow both eyes to be treated with the apo mimetic at the same time without an additional administration (e.g., injection) of the apo mimetic into or in the other eye. For example, an intravitreally injected apo mimetic can cross the blood-retinal barrier to reach two of the target areas, the sub-RPE-BL space and the Bruch's membrane, from where the apo mimetic may enter the choriocapillaris and ultimately the fellow non-administered eye. Also without intending to be bound by theory, some amount of the apo mimetic may enter the fellow non-administered eye by way of the aqueous humor, which drains via the trabecular meshwork and Schlemm's canal that flows into the blood system. Accordingly, some embodiments relate to a method of treating AMD, comprising administering to a subject in need of treatment a therapeutically effective amount of an apo mimetic and a therapeutically effective amount of a complement inhibitor, wherein the apo mimetic is administered locally to, into, in or around one eye and has a therapeutic effect in both eyes.

In additional embodiments, the apo mimetic [e.g., an apoA-I mimetic (e.g., L-4F) and/or an apoE mimetic (e.g., AEM-28-14)] is administered locally (e.g., by intravitreal injection) once every month (4 weeks) or 1.5 months (6 weeks). In other embodiments, the apo mimetic [e.g., an apoA-I mimetic (e.g., L-4F) and/or an apoE mimetic (e.g., AEM-28-14)] is administered locally (e.g., by intravitreal injection) once every 2 months (8 weeks), 2.5 months (10 weeks) or 3 months (12 weeks). In still other embodiments, the apo mimetic [e.g., an apoA-I mimetic (e.g., L-4F) and/or an apoE mimetic (e.g., AEM-28-14)] is administered locally (e.g., by intravitreal injection or via a sustained-release composition) once every 4, 5 or 6 months. In further embodiments, the apo mimetic [e.g., an apoA-I mimetic (e.g., L-4F) and/or an apoE mimetic (e.g., AEM-28-14)] is administered locally in a total of about 15 or less, 12 or less, 9 or less, 6 or less, or 3 or less (e.g., 3-6 or 7-10) administrations (e.g., injections). The apo mimetic can also be administered locally in a total of more than 15 administrations (e.g., injections), such as up to about 20 or more administrations (e.g., injections). In embodiments where the apo mimetic is administered locally to, into, in or around the eye, the frequency of administration and the total number of administrations (e.g., injections) are per administered eye in certain embodiments and for both eyes in other embodiments, as the apo mimetic may also have a therapeutic effect in the fellow non-administered eye.

In some embodiments, the apo mimetic [e.g., an apoA-I mimetic (e.g., L-4F) and/or an apoE mimetic (e.g., AEM-28-14)] and/or the complement inhibitor (e.g., lampalizumab) are administered locally to, into, in or around the eye. Potential routes, sites and means of local administration are described elsewherein herein. In some embodiments, the apo mimetic [e.g., an apoA-I mimetic (e.g., L-4F) and/or an apoE mimetic (e.g., AEM-28-14)] and/or the complement inhibitor (e.g., lampalizumab) are administered by injection (e.g., intravitreal, subconjunctival, subretinal or sub-Tenon's injection), eye drop or implant (e.g., intravitreal, subretinal or sub-Tenon's implant). In certain embodiments, the apo mimetic [e.g., an apoA-I mimetic (e.g., L-4F) and/or an apoE mimetic (e.g., AEM-28-14)] and the complement inhibitor (e.g., lampalizumab) are administered by injection (e.g., intravitreal, subconjunctival, subretinal or sub-Tenon's injection). In further embodiments, the apo mimetic [e.g., an apoA-I mimetic (e.g., L-4F) and/or an apoE mimetic (e.g., AEM-28-14)] and/or the complement inhibitor (e.g., lampalizumab) are administered via a sustained-release composition. Non-limiting examples of sustained-release compositions include those described elsewhere herein.

In certain embodiments, the apo mimetic [e.g., an apoA-I mimetic (e.g., L-4F) and/or an apoE mimetic (e.g., AEM-28-14)] is administered locally to, into, in or around the eye in the early phase of treatment, and then the apo mimetic is administered systemically. As a non-limiting example, the initial administration(s) (e.g., the first one to five administrations) of the apo mimetic can be local via injection (e.g., intravitreal, subconjunctival, subretinal or sub-Tenon's injection), and then subsequent administration(s) of the apo mimetic can be systemic, such as oral, parenteral (e.g., subcutaneous, intramuscular or intravenous), or topical (e.g., intranasal or pulmonary). In other embodiments, the apo mimetic is administered only locally. In yet other embodiments, the apo mimetic is administered only systemically.

The apo mimetic [e.g., an apoA-I mimetic (e.g., L-4F or a variant or salt thereof) and/or an apoE mimetic (e.g., AEM-28-14 or a variant or salt thereof)] and the complement inhibitor (e.g., lampalizumab) can be administered via the same pharmaceutical composition or separate pharmaceutical compositions, where a composition further comprises one or more pharmaceutically acceptable excipients or carriers. If the apo mimetic (e.g., an apoA-I mimetic and/or an apoE mimetic) and the complement inhibitor are administered via the same composition, such a composition can be prepared in advance or can be prepared by combining the apo mimetic and the complement inhibitor into the same formulation shortly or just before the formulation is administered (e.g., by injection). Administration of the apo mimetic (e.g., an apoA-I mimetic and/or an apoE mimetic) and the complement inhibitor in the same composition decreases the number of times the patient is subjected to a potentially invasive procedure (e.g., intravitreal injection) compared to separate administration of the therapeutic agents, which can have significant benefits for the patient and the care provider as described elsewhere herein.

In some embodiments, the composition containing the apo mimetic [e.g., an apoA-I mimetic (e.g., L-4F) and/or an apoE mimetic (e.g., AEM-28-14)], and/or the composition containing the complement inhibitor (e.g., lampalizumab), whether the same composition or separate compositions, are formulated as an injectable solution or suspension (e.g., for intravitreal, subconjunctival, subretinal or sub-Tenon's injection). Examples of formulations for injection into the eye include without limitation those described elsewhere herein. In other embodiments, the composition containing the apo mimetic [e.g., an apoA-I mimetic (e.g., L-4F) and/or an apoE mimetic (e.g., AEM-28-14)], and/or the composition containing the complement inhibitor (e.g., lampalizumab), whether the same composition or separate compositions, are formulated as an eye drop or an implant (e.g., an intravitreal, subretinal or sub-Tenon's implant). Use of an eye drop, or implantation of the implant one or two times, can avoid potential issues associated with repeated injections. In further embodiments, the composition containing the apo mimetic [e.g., an apoA-I mimetic (e.g., L-4F) and/or an apoE mimetic (e.g., AEM-28-14)], and/or the composition containing the complement inhibitor (e.g., lampalizumab), whether the same composition or separate compositions, are configured for sustained release of the apo mimetic and/or the complement inhibitor. Non-limiting examples of sustained-release compositions include those described elsewhere herein. Use of a sustained-release composition can decrease the number of times a potentially invasive procedure (e.g., intravitreal injection) is performed to administer a drug, and can improve the profile of the amount of the drug delivered to the target site over a period of time.

In certain embodiments, the composition containing the apo mimetic [e.g., an apoA-I mimetic (e.g., L-4F) and/or an apoE mimetic (e.g., AEM-28-14)], whether or not it contains the complement inhibitor (e.g., lampalizumab), comprises about 75-95% (e.g., about 90%) of the apo mimetic(s) and about 5-25% (e.g., about 10%) of the corresponding apolipoprotein(s) (e.g., apoA-I and/or apoE) or an active portion or domain thereof by weight or molarity relative to their combined amount.

In some embodiments, the composition containing the apo mimetic [e.g., an apoA-I mimetic (e.g., L-4F) and/or an apoE mimetic (e.g., AEM-28-14)], and/or the composition containing the complement inhibitor (e.g., lampalizumab), whether the same composition or separate compositions, comprise one or more excipients that inhibit peptide/protein aggregation, increase peptide/protein solubility, reduce solution viscosity or increase peptide/protein stability, or any combination or all thereof. Examples of such excipients include without limitation those described elsewhere herein, and the use of such excipients can have benefits as described elsewhere herein. For instance, such excipients can improve the injectability of a composition, and thus can enable the use of a needle with a smaller gauge for injection. Moreover, the use of such excipients can decrease the volume needed to administer a given amount of a peptide or protein, and hence can reduce ocular pressure if the peptide or protein is administered by injection into the eye. In addition, the use of such excipients can allow a greater dose of a peptide or protein to be administered for a given volume, which can permit the peptide or protein to be administered less frequently for a given total dose administered over a time period.

In some embodiments, the complement inhibitor (e.g., lampalizumab) is administered (e.g., by intravitreal injection) in a dose higher than the conventional or recommended dose, and in a frequency less than the conventional or recommended dosing frequency, for the complement inhibitor in the absence of treatment with the apo mimetic [e.g., an apoA-I mimetic (e.g., L-4F) and/or an apoE mimetic (e.g., AEM-28-14)]. In certain embodiments, the complement inhibitor (e.g., lampalizumab) is administered (e.g., by intravitreal injection) in a dose at least about 10%, 20%, 30%, 50%, 75%, 100%, 150% or 200% (e.g., at least about 30%), or about 10-30%, 30-50%, 50-100%, 100-150% or 150-200% (e.g., about 50-100%), higher than the conventional or recommended dose for the complement inhibitor in the absence of treatment with the apo mimetic [e.g., an apoA-I mimetic (e.g., L-4F) and/or an apoE mimetic (e.g., AEM-28-14)]. In further embodiments, the complement inhibitor (e.g., lampalizumab) is administered (e.g., by intravitreal injection) at least about 1.5, 2, 3, 4, 5 or 6 (e.g., at least about 2) times less frequently than the conventional or recommended dosing frequency for the complement inhibitor in the absence of treatment with the apo mimetic [e.g., an apoA-I mimetic (e.g., L-4F) and/or an apoE mimetic (e.g., AEM-28-14)].

In certain embodiments, the complement inhibitor includes, or is, lampalizumab, and lampalizumab is administered (e.g., by intravitreal injection) in a dose of about 12-14 mg, 14-16 mg, 16-18 mg or 18-20 mg once every 2, 3, 4, 5 or 6 months, optionally after being administered in a dose of about 12-14 mg, 14-16 mg, 16-18 mg or 18-20 mg once every month for the first 1, 2 or 3 months or once every 6 weeks for the first 1.5 or 3 months, compared to the conventional or recommended dose and dosing frequency for lampalizumab of about 10 mg administered by intravitreal injection once every month in the absence of treatment with the apo mimetic [e.g., an apoA-I mimetic (e.g., L-4F) and/or an apoE mimetic (e.g., AEM-28-14)].

In additional embodiments, the apo mimetic [e.g., an apoA-I mimetic (e.g., L-4F) and/or an apoE mimetic (e.g., AEM-28-14)] and the complement inhibitor are administered at least in the advanced stage of AMD further to prevent or delay the onset of neovascular (wet) AMD, and/or to treat or slow the progression of wet AMD, including types 1, 2 and 3 neovascularization. The complement inhibitor used to treat wet AMD can be the same as, different from, or in addition to the complement inhibitor used to treat dry AMD (including geographic atrophy). In certain embodiments, the complement inhibitor includes, or is, ARC1905 (ZIMURA®) or LFG316. In some embodiments, an anti-angiogenic agent is used in conjunction with the apo mimetic [e.g., an apoA-I mimetic (e.g., L-4F) and/or an apoE mimetic (e.g., AEM-28-14)] and the complement inhibitor to treat wet AMD. In certain embodiments, the anti-angiogenic agent includes, or is, an anti-VEGF agent (e.g., aflibercept [EYLEA®], bevacizumab [AVASTIN®] or ranibizumab [LUCENTIS®], or any combination or all thereof) and/or an anti-PDGF agent (e.g., E10030 [FOVISTA®]).

In some embodiments, the anti-angiogenic agent (e.g., an anti-VEGF agent) and/or the complement inhibitor (e.g., ARC1905) are administered in a frequency less than the conventional or recommended dosing frequency, and/or in a dose less than the conventional or recommended dose, for the anti-angiogenic agent and/or the complement inhibitor in the absence of treatment with the apo mimetic [e.g., an apoA-I mimetic (e.g., L-4F) and/or an apoE mimetic (e.g., AEM-28-14)]. In certain embodiments, the anti-angiogenic agent (e.g., an anti-VEGF agent) and/or the complement inhibitor (e.g., ARC1905) are administered (e.g., by intravitreal injection) at least about 1.5, 2, 3, 4, 5 or 6 (e.g., at least about 2) times less frequently than the conventional or recommended dosing frequency for the anti-angiogenic agent and/or the complement inhibitor in the absence of treatment with the apo mimetic [e.g., an apoA-I mimetic (e.g., L-4F) and/or an apoE mimetic (e.g., AEM-28-14)]. In further embodiments, the anti-angiogenic agent (e.g., an anti-VEGF agent) and/or the complement inhibitor (e.g., ARC1905) are administered (e.g., by intravitreal injection) in a dose at least about 10%, 20%, 30%, 40%, 50%, 60%, 70% or 80% (e.g., at least about 20%), or about 10-30%, 30-50% or 50-70%, less than the conventional or recommended dose for the anti-angiogenic agent and/or the complement inhibitor in the absence of treatment with the apo mimetic [e.g., an apoA-I mimetic (e.g., L-4F) and/or an apoE mimetic (e.g., AEM-28-14)]. Non-limiting examples of dosing frequencies and dosages for aflibercept, bevacizumab and ranibizumab are provided elsewhere herein.

One or more other therapeutic agents described herein can be used in combination with the apo mimetic [e.g., an apoA-I mimetic (e.g., L-4F) and/or an apoE mimetic (e.g., AEM-28-14)] and the complement inhibitor for the treatment of dry or wet AMD. In some embodiments, the additional therapeutic agent(s) include, or are, an antioxidant (e.g., vitamins, saffron carotenoids and/or zinc), an anti-dyslipidemic agent (e.g., a statin, such as atorvastatin), an anti-inflammatory agent (e.g., an NSAID such as bromfenac, and/or a corticosteroid such as fluocinolone acetonide or triamcinolone acetonide), or a neuroprotector (e.g., an endogenous neuroprotector, such as CNTF), or any combination or all thereof. Use of the apo mimetic [e.g., an apoA-I mimetic (e.g., L-4F) and/or an apoE mimetic (e.g., AEM-28-14)] may enhance the efficacy of one or more other therapeutic agents that, e.g., reduce oxidative stress, improve altered lipid homeostasis, reduce inflammation or curtail degeneration of RPE cells and retinal cells (e.g., photoreceptors), or any combination or all thereof.

In some embodiments, the additional therapeutic agent(s) are administered at least in the advanced stage of AMD. In further embodiments, the additional therapeutic agent(s) are administered at least in the intermediate stage of AMD. In still further embodiments, the additional therapeutic agent(s) are administered at least in the early stage of AMD. In certain embodiments, the additional therapeutic agent(s) administered at least in the early stage of AMD include, or are, an anti-dyslipidemic agent that reduces lipid production (e.g., a statin), and optionally an antioxidant (e.g., a vitamin, a saffron carotenoid and/or zinc) and/or an anti-inflammatory agent (e.g., an NSAID), and the additional therapeutic agent(s) are administered systemically (e.g., orally) or locally (e.g., by eye drop).

VIII. Treatment of AMD with an Apoliprotein Mimetic and an Antioxidant

Additional embodiments of the disclosure relate to a method of treating AMD, comprising administering to a subject in need of treatment a therapeutically effective amount of an apolipoprotein (apo) mimetic and a therapeutically effective amount of an antioxidant, whether or not the apo mimetic is administered locally to, into, in or around the eye in a dose from about 0.1 or 0.3 mg to about 1.5 mg per administration (e.g., per injection), or in a total dose from about 0.5 or 1 mg to about 10 mg over a period of about 6 months. Moreover, a mineral (e.g., zinc or selenium, each of which can also function as an antioxidant) can be used in conjunction with an apo mimetic and an antioxidant to treat AMD. All of the embodiments relating to the treatment of AMD with an apolipoprotein mimetic which are described in Section IV and elsewhere herein also apply to the treatment of AMD with an apo mimetic and an antioxidant (and optionally a mineral).

Examples of apolipoprotein mimetics, including apoA-I mimetics and apoE mimetics, include without limitation those described elsewhere herein. In some embodiments, the apo mimetic includes, or is, an apoA-I mimetic. In certain embodiments, the apoA-I mimetic includes, or is, 4F or a variant or salt (e.g., acetate salt) thereof. In some embodiments, all of the amino acid residues of 4F have the L-form (L-4F). In other embodiments, one or more, or all, of the amino acid residues of 4F have the D-form (e.g., D-4F having all D-amino acid residues). 4F can have a protecting group at the N-terminus (e.g., an acyl group, such as an acetyl group) and/or the C-terminus (e.g., an amide group, such as $—C(O)NH_2$). In certain embodiments, the apoA-I mimetic includes, or is, L-4F having the structure Ac-DWFKAFYDKVAEKFKEAF-$NH_2$ (SEQ. ID. NO. 13). In further embodiments, the apo mimetic includes, or is, an apoE mimetic. In certain embodiments, the apoE mimetic includes, or is, AEM-28-14 or a variant or salt thereof.

Examples of antioxidants include without limitation those described elsewhere herein. In certain embodiments, the antioxidant comprises one or more vitamins (e.g., vitamin $B_6$, vitamin C and vitamin E), one or more carotenoids (e.g., xanthophylls [e.g., lutein, zeaxanthin and meso-zeaxanthin] and carotenoids in saffron [e.g., crocin and crocetin]), or zinc, or any combination or all thereof, such as an AREDS or AREDS2 formulation, an ICAPS® formulation, an Ocuvite® formulation or Saffron 2020™ described elsewhere herein. In addition to their ability to reduce oxidative stress, antioxidants can have other beneficial properties. For instance, saffron carotenoids have anti-inflammatory and cell-protective, as well as antioxidant, effects.

In some embodiments, the antioxidant (e.g., vitamins and/or carotenoids) is administered in a dose less than the conventional or recommended dose, and/or in a frequency less than the conventional or recommended dosing frequency, for the antioxidant in the absence of treatment with the apo mimetic [e.g., an apoA-I mimetic (e.g., L-4F) and/or an apoE mimetic (e.g., AEM-28-14)], whether or not the apo mimetic is administered locally in a dose from about 0.1 or 0.3 mg to about 1.5 mg per administration (e.g., per injection), or in a total dose from about 0.5 or 1 mg to about 10 mg over a period of about 6 months. Administration of a lower dose of an antioxidant can have benefits for the subject, such as fewer side effects. For example, higher intake of β-carotene can increase the risk of lung cancer in smokers. As another example, higher intake of vitamin E can increase the risk of heart failure in at-risk subjects. In some embodiments, the antioxidant (e.g., vitamins and/or carotenoids) is administered in a dose at least about 10%, 20%, 30%, 40%, 50%, 60%, 70% or 80% (e.g., at least about 20%), or about 10-30%, 30-50% or 50-70%, less than the conventional or recommended dose for the antioxidant in the absence of treatment with the apo mimetic [e.g., an apoA-I mimetic (e.g., L-4F) and/or an apoE mimetic (e.g., AEM-28-14)]. In further embodiments, the antioxidant (e.g., vitamins and/or carotenoids) is administered at least about 2, 3, 5, 7 or 10 (e.g., at least about 2) times less frequently than the conventional or recommended dosing frequency for the antioxidant in the absence of treatment with the apo mimetic [e.g., an apoA-I mimetic (e.g., L-4F) and/or an apoE mimetic (e.g., AEM-28-14)]. In certain embodiments, the antioxidant (e.g., vitamins and/or carotenoids) is administered, whether systemically (e.g., orally) or locally in a non-invasive manner (e.g., by eye drop), once every two or three days compared to the conventional or recommended dosing frequency for the antioxidant of at least one time every day orally in the absence of treatment with the apo mimetic [e.g., an apoA-I mimetic (e.g., L-4F) and/or an apoE mimetic (e.g., AEM-28-14)].

Treatment of AMD with the apo mimetic [e.g., an apoA-I mimetic (e.g., L-4F) and/or an apoE mimetic (e.g., AEM-28-14)] and the antioxidant (e.g., vitamins and/or carotenoids) may have a synergistic effect. For instance, treatment with the apo mimetic (e.g., an apoA-I mimetic and/or an apoE mimetic) may enhance the efficacy of the antioxidant, and/or vice versa. As an example, L-4F can markedly reduce lipid deposits from the Bruch's membrane and the sub-RPE-BL space, thereby decreasing the amount of lipids susceptible to oxidation. As another example, the ability of L-4F to curtail the oxidation of lipids and to clear pro-inflammatory oxidized lipids can decrease the required dosage and/or frequency of administration of the antioxidant. Synergism between the apo mimetic (e.g., an apoA-I mimetic and/or an apoE mimetic) and the antioxidant can allow, but is not required for, e.g., the antioxidant to be administered in a dose lower than the conventional or recommended dose, and/or in a frequency less than the conventional or recommended dosing frequency, for the antioxidant in the absence of treatment with the apo mimetic.

Regarding the apo mimetic, in certain embodiments the apo mimetic [e.g., an apoA-I mimetic (e.g., L-4F) and/or an apoE mimetic (e.g., AEM-28-14)] is administered locally to, into, in or around the eye (e.g., by intravitreal injection) in a dose of about 0.1 or 0.3-1.5 mg, 0.1-0.5 mg, 0.5-1 mg, 1-1.5 mg, 0.1-0.3 mg, 0.3-0.5 mg, 0.5-0.75 mg, 0.75-1 mg, 1-1.25 mg or 1.25-1.5 mg (e.g., about 0.1-0.5 mg or 0.5-1 mg) per administration (e.g., per injection). The apo mimetic can also be administered locally in a dose greater than 1.5 mg per administration, such as up to about 2 mg or more per administration (e.g., per injection). In further embodiments, the apo mimetic [e.g., an apoA-I mimetic (e.g., L-4F) and/or an apoE mimetic (e.g., AEM-28-14)] is administered locally (e.g., by intravitreal injection or via a sustained-release composition) in a total dose of about 0.5 or 1-10 mg, 0.5 or 1-5 mg, 5-10 mg, 0.5 or 1-3 mg, 3-5 mg, 5-7.5 mg or 7.5-10 mg (e.g., about 0.5-3 mg or 3-5 mg) over a period of about 6 months, where the duration/length of treatment with the apo mimetic can be, e.g., about 6-12, 12-18 or 18-24 months or longer. The apo mimetic can also be administered locally in a total dose greater than 10 mg over a period of about 6 months, such as up to about 15 mg or more over a period of about 6 months. In yet further embodiments, the apo mimetic [e.g., an apoA-I mimetic (e.g., L-4F) and/or an apoE mimetic (e.g., AEM-28-14)] is administered locally in a total dose of about 1 or 2-20 mg, 5-15 mg, 1-5 mg, 5-10 mg, 10-15 mg, 15-20 mg, 1-3 mg, 3-5 mg, 5-7.5 mg, 7.5-10 mg, 10-12.5 mg, 12.5-15 mg, 15-17.5 mg or 17.5-20 mg (e.g., about 1-5 mg or 5-10 mg) for the whole/entire treatment regimen with the apo mimetic. The apo mimetic can also be administered locally in a total dose greater than 20 mg for the entire treatment regimen, such as up to about 25 mg, 30 mg, 40 mg, 50 mg or more for the entire treatment regimen.

In embodiments where the apo mimetic [e.g., an apoA-I mimetic (e.g., L-4F) and/or an apoE mimetic (e.g., AEM-28-14)] is administered locally to, into, in or around the eye, the dose per administration, the total dose over a period of about 6 months, and the total dose for the whole treatment regimen are per administered eye in certain embodiments and for both eyes in other embodiments. The blood system may allow some amount (e.g., a therapeutically effective amount) of the apo mimetic locally administered (e.g., injected) into or in one eye to be distributed to the other eye, in which case the dose of the apo mimetic can optionally be adjusted (e.g., increased) to take into account the other eye (which may be in a less diseased condition), and which may allow both eyes to be treated with the apo mimetic at the same time without an additional administration (e.g., injection) of the apo mimetic into or in the other eye. For example, an intravitreally injected apo mimetic can cross the blood-retinal barrier to reach two of the target areas, the sub-RPE-BL space and the Bruch's membrane, from where the apo mimetic may enter the choriocapillaris and ultimately the fellow non-administered eye. Also without intending to be bound by theory, some amount of the apo mimetic may enter the fellow non-administered eye by way of the aqueous humor, which drains via the trabecular meshwork and Schlemm's canal that flows into the blood system. Accordingly, some embodiments relate to a method of treating AMD, comprising administering to a subject in need of treatment a therapeutically effective amount of an apo mimetic and a therapeutically effective amount of an antioxidant, wherein the apo mimetic is administered locally to, into, in or around one eye and has a therapeutic effect in both eyes.

In additional embodiments, the apo mimetic [e.g., an apoA-I mimetic (e.g., L-4F) and/or an apoE mimetic (e.g., AEM-28-14)] is administered locally (e.g., by intravitreal injection) once every month (4 weeks) or 1.5 months (6 weeks). In other embodiments, the apo mimetic [e.g., an apoA-I mimetic (e.g., L-4F) and/or an apoE mimetic (e.g., AEM-28-14)] is administered locally (e.g., by intravitreal injection) once every 2 months (8 weeks), 2.5 months (10 weeks) or 3 months (12 weeks). In still other embodiments, the apo mimetic [e.g., an apoA-I mimetic (e.g., L-4F) and/or an apoE mimetic (e.g., AEM-28-14)] is administered locally (e.g., by intravitreal injection or via a sustained-release composition) once every 4, 5 or 6 months. In further embodiments, the apo mimetic [e.g., an apoA-I mimetic (e.g., L-4F) and/or an apoE mimetic (e.g., AEM-28-14)] is administered locally in a total of about 15 or less, 12 or less, 9 or less, 6 or less, or 3 or less (e.g., 3-6 or 7-10) administrations (e.g., injections). The apo mimetic can also be administered locally in a total of more than 15 administrations (e.g., injections), such as up to about 20 or more administrations (e.g., injections). In embodiments where the apo mimetic is administered locally to, into, in or around the eye, the frequency of administration and the total number of administrations (e.g., injections) are per administered eye in certain embodiments and for both eyes in other embodiments, as the apo mimetic may also have a therapeutic effect in the fellow non-administered eye.

In some embodiments, the apo mimetic [e.g., an apoA-I mimetic (e.g., L-4F) and/or an apoE mimetic (e.g., AEM-28-14)] and the antioxidant (e.g., vitamins and/or carotenoids) are administered at least in the advanced stage of AMD to treat or slow the progression of central geographic atrophy (GA) and/or neovascular AMD (including types 1, 2 and 3 NV), and/or to prevent or delay the onset of neovascular AMD. Use of the antioxidant can inhibit the formation of oxidized lipids, which can be strongly pro-inflammatory and hence pro-angiogenic. In further embodiments, the apo mimetic [e.g., an apoA-I mimetic (e.g., L-4F) and/or an apoE mimetic (e.g., AEM-28-14)] and the antioxidant (e.g., vitamins and/or carotenoids) are administered at least in the intermediate stage of AMD to treat or slow the progression of non-central GA, and/or to prevent or delay the onset of central GA and/or neovascular AMD. In yet further embodiments, the apo mimetic [e.g., an apoA-I mimetic (e.g., L-4F) and/or an apoE mimetic (e.g., AEM-28-14)] and the antioxidant (e.g., vitamins and/or carotenoids) are administered at least in the early stage of AMD or the initial phase of intermediate AMD to prevent or delay the onset of non-central GA. In additional embodiments, the antioxidant (e.g., vitamins and/or carotenoids), and optionally the apo mimetic [e.g., an apoA-I mimetic (e.g., L-4F) and/or an apoE mimetic (e.g., AEM-28-14)], are administered at least in the early stage of AMD.

In certain embodiments, treatment with the apo mimetic [e.g., an apoA-I mimetic (e.g., L-4F) and/or an apoE mimetic (e.g., AEM-28-14)] and the antioxidant (e.g., vitamins and/or carotenoids) slows the progression of central GA and/or non-central GA (e.g., reduces the rate of GA progression, or reduces the GA lesion area or size) by at least about 10%, 20%, 30%, 40%, 50%, 60%, 70% or 80% (e.g., by at least about 20%), or by about 20-40%, 40-60% or 60-80%. In further embodiments, treatment with the apo mimetic [e.g., an apoA-I mimetic (e.g., L-4F) and/or an apoE mimetic (e.g., AEM-28-14)] and the antioxidant (e.g., vitamins and/or carotenoids) slows the progression of central GA and/or non-central GA (e.g., reduces the rate of GA progression, or reduces the GA lesion area or size) at least about 10%, 20%, 30%, 50%, 100%, 150%, 200% or 300% (e.g., at least about 20% or 30%), or about 10-30%, 30-50%, 50-100%, 100-200% or 200-300% (e.g., about 50-100%), more than treatment with the antioxidant in the absence of treatment with the apo mimetic.

The apo mimetic [e.g., an apoA-I mimetic (e.g., L-4F) and/or an apoE mimetic (e.g., AEM-28-14)] and the antioxidant (e.g., vitamins and/or carotenoids) can be administered by any suitable method. In some embodiments, the apo mimetic (e.g., an apoA-I mimetic and/or an apoE mimetic) and/or the antioxidant are administered locally to, into, in or around the eye, such as by injection (e.g., intravitreal, subconjunctival, subretinal or sub-Tenon's injection), eye drop or implant (e.g., intravitreal, subretinal or sub-Tenon's implant]). In certain embodiments, the apo mimetic (e.g, an apoA-I mimetic and/or an apoE mimetic) is administered locally (e.g., by intravitreal, subconjunctival, subretinal or sub-Tenon's injection). In other embodiments, the apo mimetic (e.g., an apoA-I mimetic and/or an apoE mimetic) and/or the antioxidant are administered systemically (e.g., intravenously or orally). In certain embodiments, the antioxidant is administered systemically (e.g., orally). In some embodiments, the apo mimetic (e.g., an apoA-I mimetic and/or an apoE mimetic) and/or the antioxidant are administered via a sustained-release composition.

In certain embodiments, the apo mimetic [e.g., an apoA-I mimetic (e.g., L-4F) and/or an apoE mimetic (e.g., AEM-28-14)] is administered locally to, into, in or around the eye in the early phase of treatment, and then the apo mimetic is administered systemically. As a non-limiting example, the initial administration(s) (e.g., the first one to five administrations) of the apo mimetic can be local via injection (e.g., intravitreal, subconjunctival, subretinal or sub-Tenon's injection), and then subsequent administration(s) of the apo mimetic can be systemic, such as oral, parenteral (e.g., subcutaneous, intramuscular or intravenous), or topical (e.g., intranasal or pulmonary). In other embodiments, the apo mimetic is administered only locally. In yet other embodiments, the apo mimetic is administered only systemically.

The apo mimetic [e.g., an apoA-I mimetic (e.g., L-4F or a variant or salt thereof) and/or an apoE mimetic (e.g., AEM-28-14 or a variant or salt thereof)] and the antioxidant (e.g., vitamins and/or carotenoids) can be administered via the same pharmaceutical composition or separate pharmaceutical compositions. If the apo mimetic (e.g., an apoA-I mimetic and/or an apoE mimetic) and the antioxidant are administered in the same composition, such a composition can be prepared in advance or can be prepared by combining the apo mimetic and the antioxidant into the same formulation shortly or just before the formulation is administered (e.g., by injection). In some embodiments, the apo mimetic (e.g, an apoA-I mimetic and/or an apoE mimetic) and the antioxidant are locally administered in the same composition to, into, in or around the eye, such as by injection (e.g., intravitreal, subconjunctival, subretinal or sub-Tenon's injection), eye drop or implant (e.g., intravitreal, subretinal or sub-Tenon's implant).

In certain embodiments, the composition containing the apo mimetic [e.g., an apoA-I mimetic (e.g., L-4F) and/or an apoE mimetic (e.g., AEM-28-14)], whether or not it contains the antioxidant (e.g., vitamins and/or carotenoids), comprises about 75-95% (e.g., about 90%) of the apo mimetic(s) and about 5-25% (e.g., about 10%) of the corresponding apolipoprotein(s) (e.g., apoA-I and/or apoE) or an active portion or domain thereof by weight or molarity relative to their combined amount.

One or more other therapeutic agents described herein can be used in conjunction with the apo mimetic [e.g., an apoA-I mimetic (e.g., L-4F) and/or an apoE mimetic (e.g., AEM-28-14)] and the antioxidant (e.g., vitamins and/or carotenoids) for the treatment of atrophic (dry) or neovascular (wet) AMD. In some embodiments, the additional therapeutic agent(s) include, or are, an anti-angiogenic agent (e.g., an anti-VEGF agent, such as aflibercept, bevacizumab or ranibizumab, and/or an anti-PDGF agent such as E10030), a complement inhibitor (e.g., a C5 inhibitor such as ARC1905 or LFG316, and/or a complement factor D inhibitor such as lampalizumab), an anti-inflammatory agent (e.g., an NSAID such as bromfenac, and/or a corticosteroid such as fluocinolone acetonide or triamcinolone acetonide), a neuroprotector (e.g., glatiramer acetate and/or CNTF), or an anti-dyslipidemic agent (e.g., a statin, such as atorvastatin), or any combination or all thereof. Use of the apo mimetic [e.g., an apoA-I mimetic (e.g., L-4F) and/or an apoE mimetic (e.g., AEM-28-14)] may enhance the efficacy of one or more other therapeutic agents that, e.g., curtail the growth and leakage of new blood vessels, reduce inflammation, reduce oxidative stress, curtail degeneration of RPE cells and retinal cells (e.g., photoreceptors), or improve altered lipid homeostasis, or any combination or all thereof.

In some embodiments, the additional therapeutic agent is administered at least in the advanced stage of AMD. In certain embodiments, the additional therapeutic agent includes, or is, an anti-angiogenic agent (e.g., an anti-VEGF agent) and optionally a neuroprotector (e.g., an endogenous neuroprotector such as CNTF) and is administered at least in the advanced stage of AMD to treat or slow the progression of wet AMD, including types 1, 2 and 3 neovascularization. In other embodiments, the additional therapeutic agent includes, or is, a complement inhibitor (e.g., lampalizumab) and/or a neuroprotector (e.g., an endogenous neuroprotector such as CNTF) and is administered at least in the advanced stage of AMD to treat or slow the progression of central geographic atrophy (GA).

In further embodiments, the additional therapeutic agent is administered at least in the intermediate stage of AMD. In certain embodiments, the additional therapeutic agent includes, or is, a complement inhibitor (e.g., lampalizumab) and/or a neuroprotector (e.g., glatiramer acetate and/or CNTF) and is administered at least in the intermediate stage of AMD to treat or slow the progression of non-central GA, and/or to prevent or delay the onset of central GA, or is administered at least in the early stage of AMD or the initial phase of intermediate AMD to prevent or delay the onset of non-central GA. In still further embodiments, the additional therapeutic agent is administered at least in the early stage of AMD. In certain embodiments, the additional therapeutic agent administered at least in the early stage of AMD includes, or is, an anti-dyslipidemic agent that reduces lipid production (e.g., a statin), and optionally an anti-inflammatory agent (e.g., an NSAID), and the additional therapeutic agent is administered systemically (e.g., orally) or locally (e.g., by eye drop).

IX. Treatment of Other Eye Diseases

The therapeutic agents described herein can be used to treat other eye diseases and disorders in addition to age-related macular degeneration (AMD). Non-limiting examples of other eye diseases and disorders that can be treated with one or more therapeutic agents described herein include juvenile macular degeneration (e.g., Stargardt disease), maculopathy (e.g., age-related maculopathy [ARM] and diabetic maculopathy [DMP] [including partial ischemic DMP]), macular edema (e.g., diabetic macular edema [DME][including clinically significant DME, focal DME and diffuse DME], Irvine-Gass Syndrome [postoperative macular edema], and macular edema following RVO [including central RVO and branch RVO]), retinopathy (e.g., diabetic retinopathy [including in patients with DME], Purtscher's retinopathy and radiation retinopathy), retinal artery occlusion (RAO) (e.g., central and branch RAO), retinal vein occlusion (RVO) (e.g., central RVO [including central RVO with cystoid macular edema {CME}] and branch RVO [including branch RVO with CME]), glaucoma (including low-tension, normal-tension and high-tension glaucoma), ocular hypertension, retinitis (e.g., Coats' disease [exudative retinitis] and retinitis pigmentosa), chorioretinitis, choroiditis (e.g., serpiginous choroiditis), uveitis (including anterior uveitis, intermediate uveitis, posterior uveitis with or without CME, and pan-uveitis), retinal pigment epithelium (RPE) detachment, and diseases associated with increased intra- or extracellular lipid storage or accumulation in addition to AMD.

In some embodiments, an apolipoprotein mimetic (e.g., an apoA-I mimetic [e.g., L-4F] and/or an apoE mimetic [e.g., AEM-28-14]), either alone or in combination with one or more other therapeutic agents, is used to treat an eye disease or disorder other than AMD. In certain embodiments, an apo mimetic having anti-inflammatory property (e.g., an apoA-I mimetic [e.g., L-4F] and/or an apoE mimetic [e.g., AEM-28-14]), either alone or in combination with another therapeutic agent, is administered to treat an inflammatory eye disease or disorder, such as uveitis. In such a case, the apo mimetic (e.g., L-4F) acts as an anti-inflammatory agent and can be utilized in place of a steroidal or non-steroidal anti-inflammatory drug. The use of an apo mimetic (e.g., an apoA-I mimetic [e.g., L-4F] and/or an apoE mimetic [e.g., AEM-28-14]) in conjunction with an anti-angiogenic agent (e.g., an anti-VEGF agent) to treat eye diseases and disorders in addition to AMD is described elsewhere herein. In further embodiments, an apo mimetic (e.g., an apoA-I mimetic [e.g., L-4F] and/or an apoE mimetic [e.g., AEM-28-14]), in conjunction with an anti-VEGF agent, a neuroprotector, a kinase inhibitor or c-peptide (connecting peptide), or any combination or all thereof, is administered to treat diabetic retinopathy. Embodiments relating to the treatment of AMD using an apo mimetic [e.g., an apoA-I mimetic (e.g., L-4F) and/or an apoE mimetic (e.g., AEM-28-14)] alone or in combination with another therapeutic agent (e.g., an anti-angiogenic agent [e.g., an anti-VEGF agent], a complement inhibitor or an antioxidant) and described elsewhere herein also apply to the treatment of other eye diseases and disorders using an apo mimetic alone or in combination with that given type of therapeutic agent.

X. Administration of Therapeutic Agents

The therapeutic agents described herein can be administered to a subject by any suitable method, including any suitable means for local or systemic administration. In certain embodiments, the therapeutic agents are administered by intravitreal injection or implant, subconjunctival injection or implant, subretinal injection or implant, sub-Tenon's injection or implant, peribulbar injection, eye drop, oral ingestion, or intravenous injection or infusion.

In some embodiments, one or more, or all, of the therapeutic agent(s) are administered locally. Local administration of a therapeutic agent can deliver the agent to the target site(s) more effectively, avoid first-pass metabolism and require a lower administration dose of the agent, and thereby can reduce any side effect caused by the agent. As the pathological events of AMD occur in the eye, the therapeutic agent(s) used to treat AMD can be locally administered to the eye for more effective treatment. For example, the lipid-containing material (e.g., lipids, lipoproteins and apolipoproteins) that accumulates in the Bruch's membrane (BrM), the sub-RPE-BL space and the subretinal space appears to be of intraocular origin (e.g., secreted by retinal pigment epithelium [RPE] cells). Therefore, a more effective reduction in the accumulation of such material can involve local administration of one or more anti-dyslipidemic agents to the target sites in the eye.

Potential routes/modes of local administration include without limitation intraaqueous (the aqueous humor), peribulbar, retrobulbar, suprachoroidal, subconjunctival, intraocular, periocular, subretinal, intrascleral, posterior juxtascleral, trans-scleral, sub-Tenon's, intravitreal and transvitreal. Subretinal administration administers a therapeutic agent below the retina, such as, e.g., the subretinal space, the RPE, the sub-RPE-BL space or the choroid, or any combination or all thereof. Potential sites of local administration include, but are not limited to, the anterior chamber (aqueous humor) and the posterior chamber of the eye, the vitreous humor (vitreous body), the retina (including the macula and/or the photoreceptor layer), the subretinal space, the RPE, the sub-RPE-BL space, the choroid (including the BrM and the choriocapillaris endothelium), the sclera, and the sub-Tenon's capsule/space.

In some embodiments, a therapeutic agent is delivered across the sclera and the choroid to the vitreous humor, from where it can diffuse to the target tissue(s), e.g., the retina (e.g., photoreceptors), the subretinal space, the RPE, the sub-RPE-BL space or the BrM, or any combination or all thereof. In other embodiments, a therapeutic agent is delivered across the sclera and the choroid to the target tissue(s), e.g., the retina (e.g., photoreceptors), the subretinal space, the RPE and/or the sub-RPE-BL space, from where it can diffuse to the BrM if the BrM is a target tissue. In further embodiments, a therapeutic agent is administered intraocularly into the anterior or posterior chamber of the eye, the vitreous humor, the retina or the subretinal space, for example.

Potential means of local administration include without limitation injection, implantation, and means for local topical administration to the eye, such as eye drop and contact lens. In some embodiments, one or more, or all, of the therapeutic agent(s) are administered by intravitreal (e.g., micro-intravitreal), subconjunctival, subretinal or sub-Tenon's injection or implantation. As an example, in certain embodiments one or more apolipoprotein mimetics [e.g., an apoA-I mimetic (e.g., L-4F) and/or an apoE mimetic (e.g., AEM-28-14)] are injected into the vitreous humor, underneath the conjunctiva, below the retina or into the sub-Tenon's capsule of the eye at least one time every 4 weeks (1 month), 6 weeks, 8 weeks (2 months), 10 weeks, 12 weeks (3 months), 4 months, 5 months or 6 months for a period of time (e.g., about 6 months, 12 months, 18 months, or 24 months or longer) as determined by the treating physician to treat, e.g., atrophic AMD (including non-central and/or central geographic atrophy) and/or neovascular AMD.

A method that can administer a therapeutic agent less frequently than intravitreal injection is a posterior juxtascleral depot. For example, Retaane® is a blunt, tinted, posterior juxtascleral depot cannula that delivers a certain amount (e.g., about 15 mg) of anecortave acetate onto the sclera directly behind the macula while leaving the globe intact. Anecortave acetate can be administered once every 6 months using this delivery method, compared to monthly or bimonthly intravitreal injections of ranibizumab or aflibercept, respectively. Moreover, the posterior juxtascleral depot method greatly decreases the risk of intraocular infection, endophthalmitis and detachment of the retina.

Although local administration of a therapeutic agent to the eye for the treatment of AMD or another eye disorder may have advantages such as greater efficacy and reduced side effects, systemic administration of a therapeutic agent may be desired in certain circumstances. As an example, oral administration of a therapeutic agent can increase patient compliance due to ease of use and non-invasiveness if, e.g., a topical formulation for local delivery (e.g., eye drop or contact lens) cannot be developed for that therapeutic agent. As another example, a pathological event of AMD may have a non-local component. For instance, the amount of lipid-containing material RPE cells secrete into the BrM, the sub-RPE-BL space and the subretinal space may be affected in part by the uptake of plasma lipids (e.g., cholesterol and fatty acids) and lipoproteins (e.g., LDLs) by RPE cells. In such a case, it may be desirable to administer systemically one or more anti-dyslipidemic agents that decrease the production of such lipids and lipoproteins by the liver.

In some embodiments, one or more of the therapeutic agent(s) are administered systemically. Potential routes of systemic administration include without limitation oral, parenteral (e.g., intradermal, subcutaneous, intramuscular, intravascular, intravenous, intraarterial, intramedullary and intrathecal), intracavitary, intraperitoneal, and topical (e.g., transdermal, transmucosal, intranasal [e.g., by nasal spray or drop], pulmonary [e.g., by inhalation], buccal, sublingual, rectal and vaginal).

In certain embodiments, one or more anti-dyslipidemic agents are administered systemically. For example, in certain embodiments a fibrate and/or a statin are administered orally, and/or a GLP-1 receptor agonist is administered subcutaneously. In further embodiments, one or more antioxidants are administered systemically. As an example, in certain embodiments vitamins, saffron carotenoids and/or zinc are administered orally. In yet further embodiments, one or more anti-inflammatory agents are administered systemically. For example, in certain embodiments an NSAID (e.g., a coxib) is administered orally, and/or a complement inhibitor (e.g., an anti-C5 antibody, such as LFG316) is administered intravenously.

In some embodiments, one or more polypeptide therapeutic agents (e.g., an endogenous angiogenesis inhibitor such as a soluble VEGFR [e.g., VEGFR1], or angiostatin and/or endostatin) are administered by means of a viral (e.g., adenoviral or lentiviral) vector expressing the polypeptide therapeutic agent(s). As an example, AVA-101 comprises an adeno-associated virus 2 (AAV2) vector containing a gene that encodes soluble VEGFR1 (FLT-1). Local administration of AVA-101 into the eye (e.g., the RPE or choriocapillary endothelium) results in expression of soluble VEGFR1 by the host retinal cells. The soluble VEGFR1 protein binds to VEGF in the extracellular space, which prevents VEGF from binding to membrane-bound VEGFRs and thereby inhibits angiogenesis. AVA-101 can be administered as, e.g., a single subretinal injection for the treatment of, e.g., neovascular AMD (including types 1, 2 and/or 3 neovascularization), which precludes the need for multiple or frequent injections.

In additional embodiments, one or more polypeptide therapeutic agents (e.g., a neuroprotector [e.g., ciliary neurotrophic factor] or an anti-angiogenic agent [e.g., an anti-VEGF agent, such as a soluble VEGFR]) are administered by means of genetically engineered cells (e.g., NTC-201 cells) producing the polypeptide therapeutic agent(s) and encapsulated in polymeric particles or a polymeric implant. As an example, an expression vector containing a gene encoding ciliary neurotrophic factor (CNTF) is transfected into RPE cells to produce genetically engineered NTC-201 cells. The NTC-201 cells are encapsulated, e.g., in a semipermeable hollow fiber-membrane capsule that is contained in a scaffold of six strands of polyethylene terephthalate yarn. The capsule and the scaffold maintain the cells (e.g., growth support and delivery of nutrients). After implantation of the encapsulated cell-based drug-delivery system (e.g., via access through the sclera), the NTC-201 cells produce and secrete CNTF through the semipermeable capsule. Such an encapsulated cell technology (e.g., NT-501) provides a controlled, continuous and sustained delivery of CNTF, and prolongs the half-life of CNTF from about 1-3 min to about 20-50 months. Intraocular delivery of CNTF using such an encapsulated cell technology can, e.g., reduce photoreceptor loss associated with the degeneration of cells of the retina, and hence can be used to treat, e.g., geographic atrophy.

One or more polypeptide therapeutic agents can also be delivered via administration of naturally occurring cells that produce and release such agents. For example, cells derived from umbilical cord tissue can rescue photoreceptors and visual functions, reportedly through the production and release of neuroprotectors such as neurotrophic factors.

The therapeutically effective amount and the frequency of administration of, and the duration of treatment with, a particular therapeutic agent for the treatment of AMD or another eye disorder may depend on various factors, including the eye disease, the severity of the disease, the mode of administration, the age, body weight, general health, gender and diet of the subject, and the response of the subject to the treatment, and can be determined by the treating physician. In some embodiments, the dosing regimen of one or more, or all, of the therapeutic agent(s) comprises one or more loading doses followed by one or more maintenance doses. The one or more loading doses are designed to establish a relatively high or therapeutically effective level of the therapeutic agent at the target site(s) relatively quickly, and the one or more maintenance doses are designed to establish a therapeutically effective level of the therapeutic agent for the period of treatment. The loading dose can be provided, e.g., by administering a dose that is greater than (e.g., 2, 3, 4 or 5 times greater than) the maintenance dose, or by administering a dose substantially similar to the maintenance dose more frequently (e.g., 2, 3, 4 or 5 times more frequently) at the beginning of treatment. As an example, for the treatment of neovascular AMD (including types 1, 2 and/or 3 neovascularization), in certain embodiments three loading doses of the anti-angiogenic agent aflibercept are administered by intravitreal injection (about 2 mg monthly for 3 months)

followed by a maintenance dose (about 2 mg) once every 2 months for a period of time as determined by the treating physician.

XI. Pharmaceutical Compositions, Delivery Systems and Kits

A therapeutic agent can be administered as a pharmaceutical composition comprising one or more pharmaceutically acceptable carriers or excipients. If two or more therapeutic agents are used for the treatment of AMD or another eye disease, they can be administered in the same pharmaceutical composition or separate pharmaceutical compositions.

Pharmaceutically acceptable carriers and excipients include pharmaceutically acceptable materials, vehicles and substances. Non-limiting examples of excipients include liquid and solid fillers, diluents, binders, lubricants, glidants, surfactants, dispersing agents, disintegration agents, emulsifying agents, wetting agents, suspending agents, thickeners, solvents, isotonic/iso-osmotic agents, buffers, pH adjusters, absorption-delaying agents, sweetening agents, flavoring agents, coloring agents, stabilizers, preservatives, antioxidants, antimicrobial agents, antibacterial agents, antifungal agents, adjuvants, encapsulating materials and coating materials. The use of such excipients in pharmaceutical formulations is known in the art. Except insofar as any conventional carrier or excipient is incompatible with a therapeutic agent, the disclosure encompasses the use of conventional carriers and excipients in formulations containing the therapeutic agents described herein. See, e.g., Remington: The Science and Practice of Pharmacy, 21st Ed., Lippincott Williams & Wilkins (Philadelphia, Pa. [2005]); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla. [2004]).

Compositions and formulations, such as injectable formulations, for use in the disclosure can be prepared in sterile form. Sterile pharmaceutical formulations are compounded or manufactured according to pharmaceutical-grade sterilization standards known to those of skill in the art, such as those disclosed in or required by the United States Pharmacopeia Chapters 797, 1072 and 1211; California Business & Professions Code 4127.7; 16 California Code of Regulations 1751; and 21 Code of Federal Regulations 211.

As an illustrative example, one or more therapeutic agents can be formulated for delivery into the eye (e.g., intravitreal, subconjunctival, subretinal or sub-Tenon's injection or eye drop). Excipients and carriers that can be used to make such formulations include without limitation solvents (e.g., aqueous solvents, such as water, saline and phosphate-buffered saline), isotonic/iso-osmotic agents (e.g., NaCl and sugars [e.g., sucrose]), pH adjusters (e.g., sodium dihydrogen phosphate and disodium hydrogen phosphate), and emulsifiers (e.g., non-ionic surfactants, such as polysorbates [e.g., polysorbate 20]). If the one or more therapeutic agents include a peptide or protein, such formulations (and any other kinds of formulations) can contain one or more substances that inhibit peptide/protein aggregation, increase peptide/protein solubility, reduce solution viscosity or increase peptide/protein stability, or any combination or all thereof, such as non-hydrophobic amino acids (e.g., arginine and histidine), polyols (e.g., myo-inositol and sorbitol), sugars (e.g., glucose, lactose, sucrose and trehalose), osmolytes (e.g., trehalose, amino acids [e.g., glycine, proline and sarcosine], and betaines [e.g., trimethylglycine]), non-ionic surfactants (e.g., alkyl polyglycosides), and ProTek® alkylsaccarides (e.g., a disaccharide [e.g., maltose or sucrose] coupled to a long-chain fatty acid or a corresponding long-chain alcohol). Because such substances increase peptide/protein solubility, they can be used to increase peptide/protein concentration and hence decrease the volume needed to administer a given amount of the peptide or protein, which can have beneficial effects such as reduction of ocular pressure (e.g., in intravitreal injection). In addition, such substances can be employed to stabilize peptides and proteins during the preparation, storage and reconstitution of lyophilized peptides and proteins.

In some embodiments, one or more, or all, of the therapeutic agent(s) independently are delivered from a sustained-release composition. As used herein, the term "sustained-release composition" encompasses sustained-release, prolonged-release, extended-release, slow-release and controlled-release compositions, systems and devices. Use of a sustained-release composition can have benefits, such as an improved profile of the amount of the drug delivered to the target site over a time period, and improved patient compliance and health due to fewer invasive procedures (e.g., injections into the eye) being performed for administration of the drug. In some embodiments, the sustained-release composition is a drug-encapsulation system, such as, e.g., nanoparticles, microparticles, a cylinder or a capsule made of, e.g., a biodegradable polymer and/or a hydrogel. In certain embodiments, the sustained-release composition comprises a hydrogel. Non-limiting examples of polymers of which a hydrogel can be composed include polyvinyl alcohol, acrylate polymers (e.g., sodium polyacrylate), and other homopolymers and copolymers having a large number of hydrophilic groups (e.g., hydroxyl and/or carboxylate groups). In other embodiments, the sustained-release drug-encapsulation system comprises a membrane-enclosed reservoir, wherein the reservoir contains a drug and the membrane is permeable to the drug.

In certain embodiments, the sustained-release composition is composed of a hydrogel formed by combining a cellulosic polymer (e.g., hydroxypropyl methyl cellulose or a derivative thereof) and polystyrene nanoparticles. Such a hydrogel can be locally administered to the eye by, e.g., eye drop, injection or implantation. The polymer chains of the cellulosic polymer and the polystyrene nanoparticles can form relaxed bonds under pressure, which allows the hydrogel to flow readily when pushed through a needle, but can form solidified bonds within seconds of release of the pressure, which allows the hydrogel to transform into a drug-carrying capsule in the eye. In certain embodiments, the hydrogel is loaded with a peptide or protein, such as an apolipoprotein mimetic or an anti-VEGF/VEGFR agent. The peptide or protein can be released from the hydrogel as the edges of the hydrogel are gradually eroded by exposure to water in the eye, which allows the peptide or protein to be released from the hydrogel over the course of months and possibly years.

In some embodiments, the sustained-release composition is a polymeric implant (e.g., a cylinder, a capsule or any other suitable form) or polymeric nanoparticles or microparticles, wherein the polymeric particles can be delivered, e.g., by eye drop or injection or from an implant. In some embodiments, the polymeric implant or polymeric nanoparticles or microparticles are composed of a biodegradable polymer (one or more biodegradable homopolymers, one or more biodegradable copolymers, or a mixture thereof). In certain embodiments, the biodegradable polymer comprises lactic acid and/or glycolic acid [e.g., an L-lactic acid-based copolymer, such as poly(L-lactide-co-glycolide) or poly(L-lactic acid-co-D,L-2-hydroxyoctanoic acid)]. The biodegradable polymer of the polymeric implant or polymeric nanoparticles or microparticles can be selected so that the polymer substantially completely degrades around the time the period of treatment is expected to end, and so that the byproducts of the polymer's degradation, like the polymer, are biocompatible.

Non-limiting examples of biodegradable polymers include polyesters, poly((α-hydroxyacids), polylactide, polyglycolide, poly(ε-caprolactone), polydioxanone, poly(hydroxyalkanoates), poly(hydroxypropionates), poly(3-hydroxypropionate), poly(hydroxybutyrates), poly(3-hydroxybutyrate), poly(4-hydroxybutyrate), poly(hydroxypentanoates), poly(3-hydroxypentanoate), poly(hydroxyvalerates), poly(3-hydroxyvalerate), poly(4-hydroxyvalerate), poly(hydroxyoctanoates), poly(2-hydroxyoctanoate), poly(3-hydroxyoctanoate), polysalicylate/polysalicylic acid, polycarbonates, poly(trimethylene carbonate), poly(ethylene carbonate), poly(propylene carbonate), tyrosine-derived polycarbonates, L-tyrosine-derived polycarbonates, polyiminocarbonates, poly(DTH iminocarbonate), poly(bisphenol A iminocarbonate), poly(amino acids), poly(ethyl glutamate), poly(propylene fumarate), polyanhydrides, polyorthoesters, poly(DETOSU-1,6HD), poly(DETOSU-t-CDM), polyurethanes, polyphosphazenes, polyimides, polyamides, nylons, nylon 12, polyoxyethylated castor oil, poly(ethylene glycol), polyvinylpyrrolidone, poly(L-lactide-co-D-lactide), poly(L-lactide-co-D,L-lactide), poly(D-lactide-co-D,L-lactide), poly(lactide-co-glycolide), poly(lactide-co-ε-caprolactone), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), poly(glycolide-co-ethylene carbonate), poly(lactide-co-propylene carbonate), poly(glycolide-co-propylene carbonate), poly(lactide-co-2-methyl-2-carboxyl-propylene carbonate), poly(glycolide-co-2-methyl-2-carboxyl-propylene carbonate), poly(lactide-co-hydroxybutyrate), poly(lactide-co-3-hydroxybutyrate), poly(lactide-co-4-hydroxybutyrate), poly(glycolide-co-hydroxybutyrate), poly(glycolide-co-3-hydroxybutyrate), poly(glycolide-co-4-hydroxybutyrate), poly(lactide-co-hydroxyvalerate), poly(lactide-co-3-hydroxyvalerate), poly(lactide-co-4-hydroxyvalerate), poly(glycolide-co-hydroxyvalerate), poly(glycolide-co-3-hydroxyvalerate), poly(glycolide-co-4-hydroxyvalerate), poly(3-hydroxybutyrate-co-4-hydroxybutyrate), poly(hydroxybutyrate-co-hydroxyvalerate), poly(3-hydroxybutyrate-co-3-hydroxyvalerate), poly(3-hydroxybutyrate-co-4-hydroxyvalerate), poly(4-hydroxybutyrate-co-3-hydroxyvalerate), poly(4-hydroxybutyrate-co-4-hydroxyvalerate), poly(ε-caprolactone-co-fumarate), poly(ε-caprolactone-co-propylene fumarate), poly(ester-co-ether), poly(lactide-co-ethylene glycol), poly(glycolide-co-ethylene glycol), poly(ε-caprolactone-co-ethylene glycol), poly(ester-co-amide), poly(DETOSU-1,6HD-co-DETOSU-t-CDM), poly(lactide-co-cellulose ester), poly(lactide-co-cellulose acetate), poly(lactide-co-cellulose butyrate), poly(lactide-co-cellulose acetate butyrate), poly(lactide-co-cellulose propionate), poly(glycolide-co-cellulose ester), poly(glycolide-co-cellulose acetate), poly(glycolide-co-cellulose butyrate), poly(glycolide-co-cellulose acetate butyrate), poly(glycolide-co-cellulose propionate), poly(lactide-co-glycolide-co-ε-caprolactone), poly(lactide-co-glycolide-co-trimethylene carbonate), poly(lactide-co-ε-caprolactone-co-trimethylene carbonate), poly(glycolide-co-ε-caprolactone-co-trimethylene carbonate), poly(3-hydroxybutyrate-co-3-hydroxyvalerate-co-4-hydroxybutyrate), poly(3-hydroxybutyrate-co-4-hydroxyvalerate-co-4-hydroxybutyrate), collagen, casein, polysaccharides, cellulose, cellulose esters, cellulose acetate, cellulose butyrate, cellulose acetate butyrate, cellulose propionate, chitin, chitosan, dextran, starch, modified starch, and copolymers and blends thereof, wherein lactide includes L-lactide, D-lactide and D,L-lactide.

As an illustrative example, sustained-release compositions comprising one or more peptides or proteins (e.g., an apoliprotein mimetic [e.g., an apoA-I or apoE mimetic] and/or an antibody or fragment thereof [e.g., an anti-VEGF antibody or fragment thereof]) for injection (e.g., intravitreal, subconjunctival, subretinal or sub-Tenon's injection) can be composed of one or more biodegradable polymers, such as hexyl-substituted poly(lactic acid) (hexPLA). HexPLA is a hydrophobic polyester having a semi-solid aggregate state, which facilitates formulation. The peptide/protein can be micronized and incorporated into a liquid hexPLA polymer matrix by cryo-milling, forming a homogeneous and injectable suspension. The peptide/protein can have good compatibility with the hexPLA polymer, good storage stability (e.g., at about 4° C. for an extended period [e.g., about 3 months or longer]), and better stability inside the polymer when shielded from the surrounding aqueous medium. Formulations of the peptide/protein with hexPLA can have a drug loading of, e.g., about 1-5% or 5-10%, and the hexPLA can have a molecular weight (MW) of, e.g., about 1000-2000 g/mol, 2000-3000 g/mol or 3000-4000 g/mol. The formulations can form spherical depots in an aqueous medium (e.g., a buffer) and release the peptide/protein for an extended period (e.g., about 1, 2, 3, 4, 5 or 6 months). The release rate of the peptide/protein can be influenced by the polymer viscosity based on the polymer MW, and by the drug loading to a lesser extent, which permits fine-tuning of the drug-release profile. The peptide/protein can maintain its structure when incorporated into the polymer matrix, and can maintain its biological activity (e.g., high affinity for its biological target) after being released from the polymer matrix.

Alternative to being released from polymeric microparticles, a solid therapeutic agent can be administered in the form of microparticles comprising primarily or consisting essentially of the therapeutic agent. Compared to the agent being substantially completely dissolved in an aqueous medium upon administration, the agent in the form of such microparticles would substantially completely dissolve over time after administration, and thereby would have a longer duration of action and require fewer administrations (e.g., injections). Furthermore, such microparticles may form a depot for prolonged delivery of the therapeutic agent. Such microparticles can optionally contain a relatively small amount of one or more excipients. Microparticles comprising primarily or consisting essentially of a therapeutic agent can be administered locally by, e.g, injection (e.g., intravitreal, subconjunctival, subretinal or sub-Tenon's injection), eye drop or implant (e.g., intravitreal, subretinal or sub-Tenon's implant).

In some embodiments, a sustained-release composition releases a low or relatively low, but therapeutically effective, dose of one or more therapeutic agents over a period of about 1 week, 2 weeks, 4 weeks (1 month), 6 weeks, 8 weeks (2 months), 10 weeks, 3 months, 6 months, 1 year, 1.5 years, 2 years, 2.5 years, 3 years or longer.

An example of a sustained-release polymeric implant is ILUVIEN®. ILUVIEN® is an intravitreal implant in the form of a tiny tube which is made of a polyimide and sealed with a silicone adhesive on one end and polyvinyl alcohol on the other end, and which releases a very small amount of the corticosteroid fluocinolone acetonide for up to 3 years. Another example of a sustained-release polymeric implant is OZURDEX®. OZURDEX® is a biodegradable, intravitreal implant that delivers an extended release of the corticosteroid dexamethasone using the NOVADUR® solid polymer delivery system. Other therapeutic agents that can be delivered via a sustained-release, biodegradable intravitreal implant include without limitation the neuroprotector brimonidine.

A further example of a sustained-release ocular drug-delivery system is that described in U.S. Pat. No. 6,375,972 to Guo et al. Guo's system comprises an inner drug core containing a drug, and an inner tube impermeable to passage of the drug, wherein the inner tube has first and second ends and covers at least a portion of the inner drug core, and the inner tube is sized and formed of a material so that the inner tube is dimensionally stable to accept the inner drug core without changing shape. An impermeable member is positioned at the inner tube's first end and prevents passage of the drug out of the inner drug core through the inner tube's first end. A permeable member is positioned at the inner tube's second end and allows diffusion of the drug out of the inner drug core through the inner tube's second end. Guo's sustained-release system can be applied by injection or implantation to the vitreous humor, under the retina or onto the sclera, for example.

An additional example of a controlled-release ocular drug-delivery system is that described in U.S. Pat. No. 6,413,540 to Yaacobi. Yaacobi's system comprises a body having a scleral surface for placement proximate to the sclera, and a well having an opening to the scleral surface and an inner core containing a drug. The system delivers the drug at a controlled rate through the sclera to or through the choroid and to the retina.

Another exemplary ocular drug-delivery device is an osmotic pump, such as that described by Ambati et al. Ambati's osmotic pump delivered separately IgG and an anti-ICAM-1 monoclonal antibody across the sclera to the choroid and the retina, with negligible systemic absorption. J. Ambati et al., *Invest. Opthalmol. Vis. Sci.*, 41:1186-91 (2000).

Drug-eluting contact lenses can also be used as sustained-release drug-delivery systems. Such contact lenses can be regarded as implantable devices or as compositions for topical administration. The release duration of drug-eluting contact lenses can be increased by, e.g., molecular imprinting, dispersion of barriers or nanoparticles/microparticles, increasing drug binding to a polymer, or sandwiching a polymer [e.g., poly(lactide-co-glycolide)] layer in a lens, or any combination or all thereof. Contact lenses can provide extended drug release for, e.g., hours to days as desired, and can increase patient compliance due to their ease of use and minimal invasiveness.

In some embodiments, one or more therapeutic agents (e.g., polynucleotides [e.g., anti-sense polynucleotides] and/or polypeptides [e.g., apolipoprotein mimetics]) independently are contained in nanoparticles, microparticles or liposomes having a lipid bilayer. In certain embodiments, the lipid bilayer is composed of one or more phospholipids. Non-limiting examples of phospholipids include phosphatidic acids (e.g., DMPA, DPPA and DSPA), phosphatidylcholines (e.g., DDPC, DEPC, DLPC, DMPC, DOPC, DPPC, DSPC and POPC), phosphatidylethanolamines (e.g., DMPE, DOPE, DPPE and DSPE), phosphatidylglycerols (e.g., DMPG, DPPG, DSPG and POPG), and phosphatidylserines (e.g., DOPS). Nanoparticles, microparticles or liposomes having a lipid bilayer composed of a fusogenic lipid (e.g., DPPG) can fuse with the plasma membrane of cells and thereby deliver a therapeutic agent into those cells. The nanoparticles, microparticles or liposomes having a lipid bilayer can be administered locally or systemically.

In some embodiments, an anti-angiogenic agent (e.g., an anti-VEGF/VEGFR agent) and an anti-inflammatory agent (e.g., an apolipoprotein mimetic [e.g., an apoA-I mimetic], a CRP inhibitor, a complement inhibitor, an inflammasome inhibitor, a corticosteroid or an NSAID, or any combination or all thereof) are contained in the same or different liposomes, nanoparticles or microparticles composed of a biodegradable polymer or a lipid bilayer, and are administered for the treatment of, e.g., neovascular AMD (including types 1, 2 and/or 3 neovascularization). In certain embodiments, the liposomes, nanoparticles or microparticles are administered locally, e.g., by eye drop or injection (e.g., intravitreal, subconjunctival, subretinal or sub-Tenon's injection).

A composition comprising one or more therapeutic agents can be presented in unit dosage form as a single dose wherein all active and inactive ingredients are combined in a suitable system, and components do not need to be mixed to form the composition to be administered. The unit dosage form can contain an effective dose, or an appropriate fraction thereof, of each of the one or more therapeutic agents. An example of a unit dosage form is a tablet, capsule, or pill for oral administration. Another example of a unit dosage form is a single-use vial, ampoule or pre-filled syringe containing a composition of one or more therapeutic agents and excipients dissolved or suspended in a suitable carrier (e.g., an aqueous solvent). The vial or ampoule can be included in a kit containing implements for administering the composition (e.g., a syringe, a filter or filter needle, and an injection needle for injecting the composition). The kit can also contain instructions for storing and administering the composition.

Alternatively, a composition comprising one or more therapeutic agents can be presented in a kit, wherein the one or more therapeutic agents, excipients and carriers (e.g., solvents) are provided in two or more separate containers (e.g., ampoules, vials, tubes, bottles or syringes) and need to be combined to prepare the composition to be administered. In some embodiments, two or more therapeutic agents (e.g., an apoA-I mimetic and/or an apoE mimetic plus an anti-angiogenic agent, a neuroprotector, an anti-inflammatory agent, a complement inhibitor, an antioxidant or an agent that curtails lipid production) are combined into the same formulation shortly or just before the formulation is administered (e.g., by injection). The one or more therapeutic agents can be provided in any suitable form (e.g., in a stable medium or lyophilized). The kit can contain implements for administering the composition (e.g., a syringe, a filter or filter needle, and an injection needle for injecting a solution or suspension). The kit can also contain instructions for storing the contents of the kit, and for preparing and administering the composition.

XII. Salt Forms

Compounds/molecules (e.g., apolipoprotein mimetics, such as L-4F and AEM-28-14) may exist in a non-salt form (e.g., a free base or a free acid, or having no basic or acidic atom or functional group) or as salts if they can form salts. Compounds that can form salts can be used in the non-salt form or in the form of pharmaceutically acceptable salts. If a compound has, e.g., a basic nitrogen atom, the compound can form an addition salt with an acid (e.g., a mineral acid [such as HCl, HBr, HI, nitric acid, phosphoric acid or sulfuric acid] or an organic acid [such as a carboxylic acid or a sulfonic acid]). Suitable acids for use in the preparation of pharmaceutically acceptable salts include without limitation acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, D-gluconic acid, D-glucuronic acid, L-glutamic acid, alpha-oxo-glutaric acid, glycolic acid, hippuric acid, hydrobromic acid, hydrochloric acid, hydroiodic acid, (±)-DL-lactic acid, (+)-L-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, propionic acid, L-pyroglutamic acid, pyruvic acid, saccharic acid, salicylic acid, 4-amino-salicylic acid, sebacic acid, stearic acid, succinic acid, sulfuric acid, tannic acid, (±)-DL-tartaric acid, (+)-L-tartaric acid, thiocyanic acid, p-toluenesulfonic acid, undecylenic acid, and valeric acid.

If a compound has an acidic group (e.g., a carboxyl group), the compound can form an addition salt with a base. Pharmaceutically acceptable base addition salts can be formed with, e.g., metals (e.g., alkali metals or alkaline earth metals) or amines (e.g., organic amines). Non-limiting examples of metals useful as cations include alkali metals (e.g., lithium, sodium, potassium and cesium), alkaline earth metals (e.g., magnesium and calcium), aluminum and zinc. Metal cations can be provided by way of, e.g., inorganic bases, such as hydroxides, carbonates and hydrogen carbonates. Non-limiting examples of organic amines useful for forming base addition salts include chloroprocaine, choline, cyclohexylamine, dibenzylamine, N,N'-dibenzylethylenediamine, dicyclohexylamine, diethanolamine, ethylenediamine, N-ethylpiperidine, histidine, isopropylamine, N-methylglucamine, procaine, pyrazine, triethylamine and trimethylamine. Pharmaceutically acceptable salts are discussed in detail in Handbook of Pharmaceutical Salts, Properties, Selection and Use, P. Stahl and C. Wermuth, Eds., Wiley-VCH (2011).

XIII. Representative Embodiments

The following embodiments of the disclosure are provided by way of example only:

1. A method of treating age-related macular degeneration (AMD), comprising administering to a subject in need of treatment a therapeutically effective amount of an apolipoprotein (apo) mimetic, wherein the apo mimetic is administered locally to, into, in or around the eye in a dose from about 0.1 or 0.3 mg to about 1.5 mg per administration, or in a total dose from about 0.5 or 1 mg to about 10 mg over a period of about 6 months.

2. The method of embodiment 1, wherein the apo mimetic comprises, or is, an apoA-I mimetic.

3. The method of embodiment 2, wherein the apoA-I mimetic comprises, or is, 4F or a variant or salt (e.g., acetate salt) thereof.

4. The method of embodiment 3, wherein the apoA-I mimetic comprises, or is, L-4F or D-4F, each optionally having a protecting group at the N-terminus and/or the C-terminus [e.g., Ac-DWFKAFYDKVAEKFKEAF-NH$_2$ (SEQ. ID. NO. 13)].

5. The method of any one of the preceding embodiments, wherein the apo mimetic comprises, or is, an apoE mimetic.

6. The method of embodiment 5, wherein the apoE mimetic comprises, or is, AEM-28-14 or a variant or salt thereof.

7. The method of any one of the preceding embodiments, wherein the apo mimetic (e.g., L-4F) is administered locally in a dose of about 0.1-0.5 mg, 0.5-1 mg, 1-1.5 mg, 0.1-0.3 mg, 0.3-0.5 mg, 0.5-0.75 mg, 0.75-1 mg, 1-1.25 mg or 1.25-1.5 mg (e.g., about 0.1-0.5 mg or 0.5-1 mg) per administration (e.g., per injection).

8. The method of any one of the preceding embodiments, wherein the apo mimetic (e.g., L-4F) is administered locally in a total dose of about 0.5 or 1-5 mg, 5-10 mg, 0.5 or 1-3 mg, 3-5 mg, 5-7.5 mg or 7.5-10 mg (e.g., about 0.5-3 mg or 3-5 mg) over a period of about 6 months.

9. The method of any one of the preceding embodiments, wherein the apo mimetic (e.g., L-4F) is administered locally in a total dose of about 1 or 2-20 mg or 5-15 mg for the whole treatment regimen.

10. The method of embodiment 9, wherein the apo mimetic (e.g., L-4F) is administered locally in a total dose of about 1-5 mg, 5-10 mg, 10-15 mg, 15-20 mg, 1-3 mg, 3-5 mg, 5-7.5 mg, 7.5-10 mg, 10-12.5 mg, 12.5-15 mg, 15-17.5 mg or 17.5-20 mg (e.g., about 1-5 mg or 5-10 mg) for the whole treatment regimen.

11. The method of any one of the preceding embodiments, wherein the dose per administration, the total dose over a period of about 6 months, and the total dose for the whole treatment regimen are per treated eye.

12. The method of any one of the preceding embodiments, wherein the apo mimetic (e.g., L-4F) is administered locally by injection (e.g., intravitreal, subconjunctival, subretinal or sub-Tenon's injection), eye drop or implant (e.g., intravitreal, intraaqueous, subretinal or sub-Tenon's implant).

13. The method of embodiment 12, wherein the apo mimetic (e.g., L-4F) is administered locally by injection (e.g., intravitreal, subconjunctival, subretinal or sub-Tenon's injection).

14. The method of embodiment 13, wherein the apo mimetic (e.g., L-4F) is administered locally by injection (e.g., intravitreal injection) in a dose concentration from about 1, 2, 3, 4 or 5 mg/mL to about 12 or 15 mg/mL.

15. The method of embodiment 14, wherein the apo mimetic (e.g., L-4F) is administered locally by injection (e.g., intravitreal injection) in a dose concentration of about 1-4 mg/mL, 4-8 mg/mL, 8-12 mg/mL, 1-5 mg/mL, 5-10 mg/mL, 10-15 mg/mL, 1-3 mg/mL, 3-5 mg/mL, 5-7.5 mg/mL, 6-8 mg/mL, 7.5-10 mg/mL, 10-12.5 mg/mL or 12.5-15 mg/mL (e.g., about 1-5 mg/mL, 5-10 mg/mL or 6-8 mg/mL).

16. The method of any one of embodiments 13 to 15, wherein the apo mimetic (e.g., L-4F) is locally administered by injection (e.g., intravitreal injection) in a dose volume of about 50-150 μL or 50-100 μL.

17. The method of embodiment 16, wherein the apo mimetic (e.g., L-4F) is administered locally by injection (e.g., intravitreal injection) in a dose volume of about 50-75 μL, 75-100 µL, 100-125 µL or 125-150 µL, or about 50 µL, 75 µL, 100 µL, 125 µL or 150 µL (e.g., about 100 µL).

18. The method of any one of embodiments 13 to 17, wherein the apo mimetic (e.g., L-4F) is locally administered by injection (e.g., intravitreal injection) once every month (4 weeks) or 1.5 months (6 weeks).

19. The method of any one of embodiments 13 to 17, wherein the apo mimetic (e.g., L-4F) is locally administered by injection (e.g., intravitreal injection) once every 2 months (8 weeks), 2.5 months (10 weeks) or 3 months (12 weeks).

20. The method of any one of embodiments 13 to 17, wherein the apo mimetic (e.g., L-4F) is locally administered by injection (e.g., intravitreal injection) once every 4, 5 or 6 months.

21. The method of any one of embodiments 13 to 20, wherein the apo mimetic (e.g., L-4F) is locally administered in a total of about 15 or less, 12 or less, 9 or less, 6 or less, or 3 or less injections (e.g., intravitreal injections).

22. The method of embodiment 21, wherein the apo mimetic (e.g., L-4F) is administered locally in a total of about 15, 14, 13, 12, 11, 10, 9, 8, 7, 6, 5, 4 or 3 (e.g., about 3-6 or 7-10) injections (e.g., intravitreal injections).

23. The method of any one of the preceding embodiments, wherein the apo mimetic (e.g., L-4F) is administered locally (e.g., by intravitreal injection) in a higher dose and/or more frequently in the early phase of treatment.

24. The method of any one of the preceding embodiments, wherein the treatment regimen with the apo mimetic (e.g., L-4F) lasts for about 36 months or less, 30 months or less, 24 months or less, 18 months or less, 12 months or less, or 6 months or less.

25. The method of embodiment 24, wherein the treatment regimen with the apo mimetic (e.g., L-4F) lasts for about 6-12, 12-18, 18-24, 24-30 or 30-36 (e.g., for about 6-12 or 12-24) months.

26. The method of any one of the preceding embodiments, wherein the apo mimetic (e.g., L-4F) is administered at least in the advanced (late) stage of AMD (e.g., to treat central geographic atrophy [GA] and/or to prevent or forestall neovascular AMD, and/or to treat neovascular AMD).

27. The method of embodiment 26, wherein the apo mimetic (e.g., L-4F) is administered locally by injection (e.g., intravitreal, subconjunctival, subretinal or sub-Tenon's injection) once every about 4-8 weeks or 4-6 weeks, in a total of about 8-12 injections or more, in a dose up to about 1-1.5 mg per injection, or in a total dose up to about 15-20 mg for the entire treatment regimen, or any combination or all thereof, in advanced AMD.

28. The method of any one of the preceding embodiments, wherein the apo mimetic (e.g., L-4F) is administered at least in the intermediate stage of AMD (e.g., to treat non-central GA and/or to prevent or forestall central GA and/or neovascular AMD, or administered in the initial phase of intermediate AMD to prevent or forestall non-central GA).

29. The method of embodiment 28, wherein the apo mimetic (e.g., L-4F) is administered locally by injection (e.g., intravitreal, subconjunctival, subretinal or sub-Tenon's injection) once every about 4-12 or 4-8 weeks, in a total of about 4-8 injections or more, in a dose up to about 0.5-1 mg or 1-1.5 mg per injection, or in a total dose up to about 10-15 mg or more for the entire treatment regimen, or any combination or all thereof, in intermediate AMD.

30. The method of any one of the preceding embodiments, wherein the apo mimetic (e.g., L-4F) is administered at least in the early stage of AMD (e.g., to prevent or forestall non-central GA).

31. The method of embodiment 30, wherein the apo mimetic (e.g., L-4F) is administered locally by injection (e.g., intravitreal, subconjunctival, subretinal or sub-Tenon's injection) less frequently (e.g., an injection every about 3, 4 or 6 months), in a smaller total number of injections (e.g., about 1, 2 or 3 injections) or in a higher dose per injection (e.g., about 0.5-1 mg or 1-1.5 mg per injection), or any combination or all thereof, in early AMD.

32. The method of any one of the preceding embodiments, wherein the apo mimetic (e.g., L-4F) is administered locally (e.g., by intravitreal injection) more frequently (which can result in a greater total number of administrations) and/or in a higher dose (higher dose per administration and/or higher total dose for the entire treatment regimen) the later the stage of AMD or the more severe the AMD condition.

33. The method of any one of the preceding embodiments, wherein the apo mimetic (e.g., L-4F) is administered locally (e.g., by intravitreal injection) in a fixed-routine regimen, an as-needed regimen or a treat-and-extend regimen.

34. The method of any one of the preceding embodiments, wherein the apo mimetic (e.g., L-4F) is administered locally via a composition comprising about 75-95% (e.g., about 90%) of the apo mimetic and about 5-25% (e.g., about 10%) of the corresponding apolipoprotein (e.g., apoA-I) or an active portion or domain thereof by weight or molarity relative to their combined amount.

35. The method of any one of the preceding embodiments, wherein the apo mimetic (e.g., L-4F) is administered locally as a composition comprising one or more excipients that inhibit peptide/protein aggregation, increase peptide/protein solubility, reduce solution viscosity or increase peptide/protein stability, or any combination or all thereof.

36. The method of any one of the preceding embodiments, wherein the apo mimetic (e.g., L-4F) is administered locally via a sustained-release composition.

37. The method of any one of the preceding embodiments, further comprising administering one or more additional therapeutic agents.

38. The method of embodiment 37, wherein the one or more additional therapeutic agents are selected from the group consisting of anti-dyslipidemic agents, PPAR-α agonists, PPAR-δ agonists, PPAR-γ agonists, anti-amyloid agents, inhibitors of lipofuscin or components thereof, antioxidants, neuroprotectors (neuroprotectants), apoptosis inhibitors, necrosis inhibitors, C-reactive protein (CRP) inhibitors, inhibitors of the complement system or components (e.g., proteins) thereof, inhibitors of inflammasomes, anti-inflammatory agents, immunosuppressants, modulators of matrix metalloproteinases (MMPs), anti-angiogenic agents, and RPE cell replacement therapies.

39. A method of preventing, delaying the onset of, slowing the progression of or reducing the extent of vision impairment or loss associated with age-related macular degeneration (AMD), comprising administering to a subject in need of treatment a therapeutically effective amount of an apolipoprotein (apo) mimetic according to any one of embodiments 1 to 38.

40. The method of embodiment 39, wherein the AMD is atrophic AMD (including noncentral and/or central geographic atrophy) or neovascular AMD (including types 1, 2 and/or 3 neovascularization).

41. A method of treating age-related macular degeneration (AMD), comprising administering to a subject in need of treatment a therapeutically effective amount of an apolipoprotein (apo) mimetic according to any one of embodiments 1 to 38 and a therapeutically effective amount of an anti-angiogenic agent.

42. The method of embodiment 41, wherein the apo mimetic comprises, or is, an apoA-I mimetic (e.g., L-4F or D-4F) and/or an apoE mimetic (e.g., AEM-28-14).

43. The method of embodiment 41 or 42, wherein the anti-angiogenic agent comprises, or is, an agent that inhibits the action of a vascular endothelial growth factor (an anti-VEGF agent), and/or an agent that inhibits the action of a platelet-derived growth factor (an anti-PDGF agent).

44. The method of embodiment 43, wherein the anti-VEGF agent is selected from the group consisting of squalamine, PAN-90806, anti-VEGF antibodies and fragments thereof (e.g., bevacizumab [AVASTIN®], ranibizumab [LUCENTIS®], ESBA1008 and ESBA903), anti-VEGF aptamers (e.g., pegaptanib [MACUGEN®]), anti-VEGF designed ankyrin repeat proteins (DARPins) (e.g., abicipar pegol), soluble receptors for VEGFs (e.g., VEGFR1), soluble fusion proteins containing one or more extracellular domains of one or more VEGFRs (e.g., aflibercept [EYLEA®] and conbercept), and combinations thereof.

45. The method of embodiment 44, wherein the anti-VEGF agent comprises, or is, aflibercept, bevacizumab or ranibizumab, or any combination or all thereof.

46. The method of any one of embodiments 41 to 45, wherein the anti-angiogenic agent (e.g., an anti-VEGF agent) is administered in a frequency less than the conventional or recommended dosing frequency, and/or in a dose less than the conventional or recommended dose, for the anti-angiogenic agent in the absence of treatment with the apo mimetic (e.g., L-4F).

47. The method of embodiment 46, wherein the anti-angiogenic agent (e.g., an anti-VEGF agent) is administered (e.g., by intravitreal injection) at least about 1.5, 2, 3, 4, 5 or 6 (e.g., at least about 2) times less frequently than the conventional or recommended dosing frequency for the anti-angiogenic agent in the absence of treatment with the apo mimetic (e.g., L-4F).

48. The method of embodiment 46 or 47, wherein the anti-angiogenic agent (e.g., an anti-VEGF agent) is administered (e.g., by intravitreal injection) in a dose at least about 10%, 20%, 30%, 40%, 50%, 60%, 70% or 80% (e.g., at least about 20%), or about 10-30%, 30-50% or 50-70%, less than the conventional or recommended dose for the anti-angiogenic agent in the absence of treatment with the apo mimetic (e.g., L-4F).

49. The method of any one of embodiments 46 to 48, wherein treatment with the apo mimetic (e.g., L-4F) reduces the total number of times (e.g., the total number of injections) the anti-angiogenic agent (e.g., an anti-VEGF agent) is administered.

50. The method of embodiment 49, wherein the anti-angiogenic agent (e.g., an anti-VEGF agent) is administered (e.g., by intravitreal injection) no more than about 20, 18, 15, 12 or 10 times.

51. The method of any one of embodiments 46 to 50, wherein treatment with the apo mimetic (e.g., L-4F) and the anti-angiogenic agent (e.g., an anti-VEGF agent) has a synergistic effect.

52. The method of any one of embodiments 46 to 51, wherein:
the anti-angiogenic agent comprises, or is, aflibercept (EYLEA®); and
aflibercept is administered (e.g., by intravitreal injection) in a dose of about 1-1.5 mg or 1.5-2 mg once every 3, 4, 5 or 6 months, optionally after being administered in a dose of about 1-1.5 mg or 1.5-2 mg once every month for the first 1, 2 or 3 months or once every 6 weeks for the first 1.5 or 3 months,
compared to the conventional or recommended dose and dosing frequency for aflibercept of 2 mg administered by intravitreal injection once every 2 months after administration of 2 mg once every month for the first 3 months in the absence of treatment with the apo mimetic (e.g., L-4F).

53. The method of any one of embodiments 46 to 51, wherein:
the anti-angiogenic agent comprises, or is, aflibercept; and
aflibercept is administered (e.g., by intravitreal injection) in a dose of about 1-1.25 mg, 1.25-1.5 mg or 1.5-1.75 mg in a frequency substantially similar to or the same as the conventional or recommended dosing frequency for aflibercept in the absence of treatment with the apo mimetic (e.g., L-4F).

54. The method of any one of embodiments 46 to 51, wherein:
the anti-angiogenic agent comprises, or is, ranibizumab (LUCENTIS®); and
ranibizumab is administered (e.g., by intravitreal injection) in a dose of about 0.2-0.3 mg, 0.3-0.4 mg or 0.4-0.5 mg once every 2, 3, 4, 5 or 6 months, optionally after being administered in a dose of about 0.2-0.3 mg, 0.3-0.4 mg or 0.4-0.5 mg once every month for the first 1, 2 or 3 months or once every 6 weeks for the first 1.5 or 3 months,
compared to the conventional or recommended dose and dosing frequency for ranibizumab of 0.5 mg administered by intravitreal injection once every month in the absence of treatment with the apo mimetic (e.g., L-4F).

55. The method of any one of embodiments 46 to 51, wherein:
the anti-angiogenic agent comprises, or is, ranibizumab; and
ranibizumab is administered (e.g., by intravitreal injection) in a dose of about 0.2-0.3 mg or 0.3-0.4 mg once every month.

56. The method of any one of embodiments 46 to 51, wherein:
the anti-angiogenic agent comprises, or is, bevacizumab (AVASTIN®); and
bevacizumab is administered (e.g., by intravitreal injection) in a dose of about 0.5-0.75 mg, 0.75-1 mg or 1-1.25 mg once every 2, 3, 4, 5 or 6 months, optionally after being administered in a dose of about 0.5-0.75 mg, 0.75-1 mg or 1-1.25 mg once every month for the first 1, 2 or 3 months or once every 6 weeks for the first 1.5 or 3 months,
compared to the conventional or recommended dose and dosing frequency for bevacizumab for the treatment of AMD of about 1.25 mg administered by intravitreal injection once every month in the absence of treatment with the apo mimetic (e.g., L-4F).

57. The method of any one of embodiments 46 to 51, wherein:
the anti-angiogenic agent comprises, or is, bevacizumab; and
bevacizumab is administered (e.g., by intravitreal injection) in a dose of about 0.5-0.75 mg or 0.75-1 mg once every month.

58. The method of any one of embodiments 46 to 51, wherein the anti-angiogenic agent (e.g., an anti-VEGF agent) is administered (e.g., by intravitreal injection) once every 2, 3, 4, 5 or 6 months.

59. The method of any one of embodiments 41 to 58, wherein the anti-angiogenic agent (e.g., an anti-VEGF agent) is administered locally to, into, in or around the eye, such as by injection (e.g., intravitreal, subconjunctival, subretinal or sub-Tenon's injection), eye drop or implant (e.g., intravitreal, intraaqueous, subretinal or sub-Tenon's implant).

60. The method of any one of embodiments 41 to 59, wherein the anti-angiogenic agent (e.g., an anti-VEGF agent) is administered to treat or slow the progression of neovascular (wet) AMD, including types 1, 2 and 3 neovascularization.

61. The method of any one of embodiments 41 to 60, wherein the anti-angiogenic agent (e.g., an anti-VEGF agent) is administered at least in the advanced (late) stage of AMD to prevent, delay the onset of, or slow the progression to neovascular AMD.

62. The method of any one of embodiments 41 to 61, wherein the apo mimetic (e.g., L-4F) is administered at least in the advanced stage of AMD.

63. The method of embodiment 62, wherein the apo mimetic (e.g., L-4F) is administered to treat central geographic atrophy, and/or to prevent, delay the onset of, or slow the progression of neovascular AMD (including types 1, 2 and 3 neovascularization).

64. The method of any one of embodiments 41 to 63, wherein the anti-angiogenic agent (e.g., an anti-VEGF agent) is administered in a fixed-routine regimen, an as-needed regimen or a treat-and-extend regimen.

65. The method of any one of embodiments 41 to 64, wherein the apo mimetic (e.g., L-4F) and the anti-angiogenic agent (e.g., an anti-VEGF agent) are administered in separate compositions.

66. The method of any one of embodiments 41 to 64, wherein the apo mimetic (e.g., L-4F) and the anti-angiogenic agent (e.g., an anti-VEGF agent) are administered in the same composition.

67. A method of treating age-related macular degeneration (AMD), comprising administering to a subject in need of treatment a therapeutically effective amount of an apolipoprotein (apo) mimetic according to any one of embodiments 1 to 38 and a therapeutically effective amount of a complement inhibitor.

68. The method of embodiment 67, wherein the apo mimetic comprises, or is, an apoA-I mimetic (e.g., L-4F or D-4F) and/or an apoE mimetic (e.g., AEM-28-14).

69. The method of embodiment 67 or 68, wherein the apo mimetic (e.g., L-4F) and the complement inhibitor are administered to treat geographic atrophy (GA).

70. The method of embodiment 69, wherein the apo mimetic (e.g., L-4F) and the complement inhibitor are administered to prevent, delay the onset of, or slow the progression of central GA and/or non-central GA.

71. The method of embodiment 69 or 70, wherein the apo mimetic (e.g., L-4F) and the complement inhibitor are administered at least in the advanced (late) stage of atrophic (dry) AMD to treat or slow the progression of central GA, and/or to prevent or delay the onset of neovascular AMD.

72. The method of any one of embodiments 69 to 71, wherein the apo mimetic (e.g., L-4F) and the complement inhibitor are administered at least in the intermediate stage of AMD to treat or slow the progression of non-central GA, and/or to prevent or delay the onset of central GA and/or neovascular AMD.

73. The method of any one of embodiments 69 to 72, wherein the apo mimetic (e.g., L-4F) and the complement inhibitor are administered at least in the early stage of AMD or the initial phase of intermediate AMD to prevent or delay the onset of non-central GA.

74. The method of any one of embodiments 67 to 73, wherein the complement inhibitor is selected from the group consisting of anti-complement factor B (CFB) antibodies and fragments thereof (e.g., TA106), anti-CFD antibodies and fragments thereof (e.g., lampalizumab), C3 inhibitors (e.g., compstatin and derivatives thereof [e.g., POT-4], mycophenolic acid-glucosamine conjugates, and soluble forms of proteins or fragments thereof [e.g., CR1, decay acceleration factor and membrane cofactor protein]), anti-C3b/iC3b antibodies and fragments thereof (e.g., 3E7), anti-C5 antibodies and fragments thereof (e.g., eculizumab and LFG316), anti-C5 aptamers (e.g., ARC1905 [Zimura®]), other C5 inhibitors (e.g., Coversin), C5a receptor antagonists (e.g., JPE-1375, JSM-7717, PMX-025, PMX-53, and anti-C5aR antibodies and fragments thereof [e.g., neutrazimab]), inhibitors of the alternative complement pathway (e.g., sCR1, TT30 and zinc), inhibitors of the classic complement pathway (e.g., sCR1), inhibitors of the lectin complement pathway (e.g., inhibitors of mannose-associated serine proteases [MASPs], such as anti-MASP antibodies and fragments thereof [e.g., OMS721]), inhibitors of membrane attack complex (MAC) formation (e.g., zinc, CD59 and modified CD59 having a glycolipid anchor), and analogs, derivatives, fragments, salts and combinations thereof.

75. The method of embodiment 74, wherein the complement inhibitor comprises, or is, lampalizumab, LFG316 or ARC1905, or any combination or all thereof.

76. The method of embodiment 75, wherein the complement inhibitor comprises, or is, lampalizumab.

77. The method of embodiment 76, wherein the subject has a mutation in the gene encoding complement factor I (CFI).

78. The method of any one of embodiments 67 to 77, wherein treatment with the apo mimetic (e.g., L-4F) and the complement inhibitor (e.g., lampalizumab) slows the progression of central GA and/or non-central GA (e.g., reduces the rate of GA progression, or reduces the GA lesion area or size) by at least about 10%, 20%, 30%, 40%, 50%, 60%, 70% or 80% (e.g., by at least about 20% or 40%), or by about 20-40%, 40-60% or 60-80%.

79. The method of any one of embodiments 67 to 78, wherein treatment with the apo mimetic (e.g., L-4F) and the complement inhibitor (e.g., lampalizumab) slows the progression of central GA and/or non-central GA (e.g., reduces the rate of GA progression, or reduces the GA lesion area or size) at least about 10%, 20%, 30%, 50%, 100%, 150%, 200% or 300% (e.g., at least about 20% or 30%), or about 10-30%, 30-50%, 50-100%, 100-200% or 200-300% (e.g., about 50-100%), more than treatment with the complement inhibitor in the absence of treatment with the apo mimetic.

80. The method of any one of embodiments 67 to 79, wherein the complement inhibitor (e.g., lampalizumab) is administered in a frequency less than the conventional or recommended dosing frequency, and/or in a dose less than the conventional or recommended dose, for the complement inhibitor in the absence of treatment with the apo mimetic (e.g., L-4F).

81. The method of embodiment 80, wherein the complement inhibitor (e.g., lampalizumab) is administered (e.g., by intravitreal injection) at least about 1.5, 2, 3, 4, 5 or 6 (e.g., at least about 2) times less frequently than the conventional or recommended dosing frequency for the complement inhibitor in the absence of treatment with the apo mimetic (e.g., L-4F).

82. The method of embodiment 80 or 81, wherein the complement inhibitor (e.g., lampalizumab) is administered (e.g., by intravitreal injection) in a dose at least about 10%, 20%, 30%, 40%, 50%, 60%, 70% or 80% (e.g., at least about 20%), or about 10-30%, 30-50% or 50-70%, less than the conventional or recommended dose for the complement inhibitor in the absence of treatment with the apo mimetic (e.g., L-4F).

83. The method of any one of embodiments 80 to 82, wherein treatment with the apo mimetic (e.g., L-4F) reduces the total number of times (e.g., the total number of injections) the complement inhibitor (e.g., lampalizumab) is administered.

84. The method of embodiment 83, wherein the complement inhibitor (e.g., lampalizumab) is administered (e.g., by intravitreal injection) no more than about 20, 18, 15, 12 or 10 times.

85. The method of any one of embodiments 80 to 84, wherein treatment with the apo mimetic (e.g., L-4F) and the complement inhibitor (e.g., lampalizumab) has a synergistic effect.

86. The method of any one of embodiments 80 to 85, wherein:
the complement inhibitor comprises, or is, lampalizumab; and
lampalizumab is administered (e.g., by intravitreal injection) in a dose of about 4-6 mg, 6-8 mg or 8-10 mg once every 2, 3, 4, 5 or 6 months, optionally after being administered in a dose of about 4-6 mg, 6-8 mg or 8-10 mg once every month for the first 1, 2 or 3 months or once every 6 weeks for the first 1.5 or 3 months,
compared to the conventional or recommended dose and dosing frequency for lampalizumab of about 10 mg administered by intravitreal injection once every month in the absence of treatment with the apo mimetic (e.g., L-4F).

87. The method of any one of embodiments 80 to 85, wherein:
the complement inhibitor comprises, or is, lampalizumab; and
lampalizumab is administered (e.g., by intravitreal injection) in a dose of about 3-5 mg, 5-7 mg or 7-9 mg once every month (4 weeks) or 1.5 months (6 weeks).

88. The method of any one of embodiments 80 to 86, wherein the complement inhibitor (e.g., lampalizumab) is administered (e.g., by intravitreal injection) once every 2, 3, 4, 5 or 6 (e.g., once every 2) months.

89. The method of any one of embodiments 67 to 88, wherein the complement inhibitor (e.g., lampalizumab) is administered locally to, into, in or around the eye, such as by injection (e.g., intravitreal, subconjunctival, subretinal or sub-Tenon's injection), eye drop or implant (e.g., intravitreal, intraaqueous, subretinal or sub-Tenon's implant).

90. The method of any one of embodiments 67 to 89, wherein the apo mimetic (e.g., L-4F) and the complement inhibitor (e.g., lampalizumab) are administered in separate compositions.

91. The method of any one of embodiments 67 to 89, wherein the apo mimetic (e.g., L-4F) and the complement inhibitor (e.g., lampalizumab) are administered in the same composition.

92. The method of any one of embodiments 67 to 91, wherein the apo mimetic (e.g., L-4F) and the complement inhibitor are administered at least in the advanced stage of AMD to prevent, delay the onset of, or slow the progression of neovascular AMD, including types 1, 2 and 3 neovascularization.

93. The method of embodiment 92, further comprising administering a therapeutically effective amount of an anti-angiogenic agent.

94. The method of embodiment 93, wherein the anti-angiogenic agent comprises, or is, an anti-VEGF agent (e.g., aflibercept [EYLEA®], bevacizumab [AVASTIN®] or ranibizumab [LUCENTIS®], or any combination or all thereof) and/or an anti-PDGF agent (e.g., E10030 [FOVISTA®]).

95. The method of any one of embodiments 92 to 94, wherein the complement inhibitor comprises, or is, ARC1905 (ZIMURA®) or LFG316.

96. The method of any one of embodiments 67 to 95, wherein the complement inhibitor (e.g., lampalizumab, ARC1905 or LFG316, or any combination or all thereof) is administered in a fixed-routine regimen, an as-needed regimen or a treat-and-extend regimen.

97. A method of treating age-related macular degeneration (AMD), comprising administering to a subject in need of treatment a therapeutically effective amount of an apolipoprotein (apo) mimetic according to any one of embodiments 1 to 38 and a therapeutically effective amount of an antioxidant.

98. The method of embodiment 97, wherein the apo mimetic comprises, or is, an apoA-I mimetic (e.g., L-4F or D-4F) and/or an apoE mimetic (e.g., AEM-28-14).

99. The method of embodiment 97 or 98, wherein the antioxidant is selected from the group consisting of anthocyanins, benzenediol abietane diterpenes (e.g., carnosic acid), carnosine, carotenoids (e.g., carotenes [e.g., β-carotene], xanthophylls [e.g., lutein, zeaxanthin and meso-zeaxanthin], and carotenoids in saffron [e.g., crocin and crocetin]), curcuminoids (e.g., curcumin), cyclopentenone prostaglandins (e.g., 15d-PGJ$_2$), flavonoids (e.g., flavonoids in *Ginkgo biloba* [e.g., myricetin and quercetin]), prenylflavonoids (e.g., isoxanthohumol), retinoids, stilbenoids (e.g., resveratrol), uric acid, vitamin A, vitamin B$_1$ (thiamine), vitamin B$_2$ (riboflavin), vitamin B$_3$ (niacin), vitamin B$_6$ (e.g., pyridoxal, pyridoxamine, 4-pyridoxic acid and pyridoxine), vitamin B$_9$ (folic acid), vitamin B$_{12}$ (cobalamin), vitamin C, vitamin E (e.g., tocopherols and tocotrienols), selenium, zinc (e.g., zinc monocysteine), inhibitors and scavengers of lipid peroxidation and byproducts thereof (e.g., vitamin E [e.g., α-tocopherol], tirilazad, NXY-059 and XJB-5-131), activators of nuclear factor (erythroid-derived 2)-like 2 (NFE2L2 or NRF2) (e.g., OT-551), superoxide dismutase (SOD) mimetics (e.g., OT-551), and analogs, derivatives, salts and combinations thereof.

100. The method of embodiment 99, wherein the antioxidant comprises one or more vitamins (e.g., vitamin B$_6$, vitamin C and vitamin E), one or more carotenoids (e.g., xanthophylls [e.g., lutein, zeaxanthin and meso-zeaxanthin] and carotenoids in saffron [e.g., crocin and crocetin]), or zinc, or any combination or all thereof, such as an AREDS or AREDS2 formulation, an ICAPS® formulation, an Ocuvite® formulation or Saffron 2020™.

101. The method of any one of embodiments 97 to 100, wherein the antioxidant (e.g., vitamins and/or carotenoids) is administered in a dose less than the conventional or recommended dose, and/or in a frequency less than the conventional or recommended dosing frequency, for the antioxidant in the absence of treatment with the apo mimetic (e.g., L-4F).

102. The method of embodiment 101, wherein the antioxidant (e.g., vitamins and/or carotenoids) is administered in a dose at least about 10%, 20%, 30%, 40%, 50%, 60%, 70% or 80% (e.g., at least about 20%), or about 10-30%, 30-50% or 50-70%, less than the conventional or recommended dose for the antioxidant in the absence of treatment with the apo mimetic (e.g., L-4F).

103. The method of embodiment 101 or 102, wherein the antioxidant (e.g., vitamins and/or carotenoids) is administered at least about 2, 3, 5, 7 or 10 (e.g., at least about 2) times less frequently than the conventional or recommended dosing frequency for the antioxidant in the absence of treatment with the apo mimetic (e.g., L-4F).

104. The method of embodiment 103, wherein the antioxidant (e.g., vitamins and/or carotenoids) is administered once every two or three days compared to the conventional or recommended dosing frequency for the antioxidant of at least one time every day in the absence of treatment with the apo mimetic (e.g., L-4F).

105. The method of any one of embodiments 97 to 104, wherein the apo mimetic (e.g., L-4F) and the antioxidant (e.g., vitamins and/or carotenoids) are administered at least in the advanced (late) stage of AMD to treat or slow the progression of central geographic atrophy (GA) and/or neovascular AMD (including types 1, 2 and 3 NV), and/or to prevent or delay the onset of neovascular AMD.

106. The method of any one of embodiments 97 to 105, wherein the apo mimetic (e.g., L-4F) and the antioxidant (e.g., vitamins and/or carotenoids) are administered at least in the intermediate stage of AMD to treat or slow the progression of non-central GA, and/or to prevent or delay the onset of central GA and/or neovascular AMD.

107. The method of any one of embodiments 97 to 106, wherein the apo mimetic (e.g., L-4F) and the antioxidant (e.g., vitamins and/or carotenoids) are administered at least in the early stage of AMD or the initial phase of intermediate AMD to prevent or delay the onset of non-central GA.

108. The method of any one of embodiments 97 to 107, wherein the antioxidant (e.g., vitamins and/or carotenoids), and optionally the apo mimetic (e.g., L-4F), are administered at least in the early stage of AMD.

109. The method of any one of embodiments 105 to 108, wherein treatment with the apo mimetic (e.g., L-4F) and the antioxidant (e.g., vitamins and/or carotenoids) slows the progression of central GA and/or non-central GA (e.g., reduces the rate of GA progression, or reduces the GA lesion area or size) by at least about 10%, 20%, 30%, 40%, 50%, 60%, 70% or 80% (e.g., by at least about 20%), or by about 20-40%, 40-60% or 60-80%.

110. The method of any one of embodiments 105 to 109, wherein treatment with the apo mimetic (e.g., L-4F) and the antioxidant (e.g., vitamins and/or carotenoids) slows the progression of central GA and/or non-central GA (e.g., reduces the rate of GA progression, or reduces the GA lesion area or size) at least about 10%, 20%, 30%, 50%, 100%, 150%, 200% or 300% (e.g., at least about 20% or 30%), or about 10-30%, 30-50%, 50-100%, 100-200% or 200-300% (e.g., about 50-100%), more than treatment with the antioxidant in the absence of treatment with the apo mimetic.

111. The method of any one of embodiments 101 to 110, wherein treatment with the apo mimetic (e.g., L-4F) and the antioxidant (e.g., vitamins and/or carotenoids) has a synergistic effect.

112. The method of any one of embodiments 97 to 111, wherein the antioxidant (e.g., vitamins and/or carotenoids) is administered systemically (e.g., orally), or locally to, into, in or around the eye (e.g., by injection [e.g., intravitreal, subconjunctival, subretinal or sub-Tenon's injection], eye drop or implant [e.g., intravitreal, subretinal or sub-Tenon's implant]).

113. The method of any one of embodiments 97 to 112, wherein the apo mimetic (e.g., L-4F) and the antioxidant (e.g., vitamins and/or carotenoids) are administered in separate compositions.

114. The method of any one of embodiments 97 to 112, wherein the apo mimetic (e.g., L-4F) and the antioxidant (e.g., vitamins and/or carotenoids) are administered in the same composition.

XIV. Examples

The following examples are intended only to illustrate the disclosure. Other assays, procedures, methodologies, techniques, conditions and reagents may alternatively be used as appropriate, and other studies may be conducted.

Example 1. Reduction of Lipid Deposits from Bruch's Membrane in Geriatric Monkeys by L-4F The macaque study was conducted according to accepted guidelines. Nine female geriatric macaques (*Macaca fascicularis*, all more than 20 years of age) with naturally occurring age-related maculopathy (exhibiting age-related drusenoid macular changes/maculopathy resembling early AMD in humans) were intravitreally injected with a sterile balanced salt solution (BSS) of the apoA-I mimetic L-4F, Ac-DWFKAFYDKVAEKFKEAF-NH$_2$ acetate salt (SEQ. ID. NO. 13) (n=7), or a placebo (a sterile BSS of scrambled L-4F [sL-4F] having the same amino acids but in a non-functional order) (n=2). One eye per animal received 6 monthly injections of the same escalating dosages of L-4F or scrambled L-4F (total of 625 μg) in a 50 μL volume. The second eye per animal was not injected and was just observed. The injected eye exhibited worse drusenoid changes than the uninjected eye per animal at baseline. Table 1 shows the dosing regimen used in the macaque study.

TABLE 1

|  | Day | Amount Injected (μg) | Concentration (mg/mL) | Volume Injected |
|---|---|---|---|---|
| Placebo (scrambled L-4F) (n = 2) | 1 | 25 | 0.5 | 50 μL one eye only |
|  | 29 | 50 | 1.0 |  |
|  | 57 | 100 | 2.0 |  |
|  | 85 | 125 | 2.5 |  |
|  | 113 | 150 | 3.0 |  |
|  | 141 | 175 | 3.5 |  |
| L-4F (n = 7) | 1 | 25 | 0.5 | 50 μL one eye only |
|  | 29 | 50 | 1.0 |  |
|  | 57 | 100 | 2.0 |  |
|  | 85 | 125 | 2.5 |  |
|  | 113 | 150 | 3.0 |  |
|  | 141 | 175 | 3.5 |  |

Clinical laboratory tests including serology, hemograms and liver enzymes were conducted, and ophthalmic examinations were also performed, including fundus photographs, optical coherence tomography (OCT), intraocular pressure testing and blood sampling. After 7 months, all animals were sacrificed and eyes were immediately prepared for histology. Histochemistry was performed with oil red O for neutral lipids and filipin for esterified cholesterol. Immunohistochemistry was performed against complement factor D (CFD) and the membrane attack complex (MAC, C5b-9), both being markers of activation of the alternative complement pathway.

For staining with oil red O (ORO), specimens were treated with a 0.3% oil red O (Sigma-Aldrich Biochemie GmbH, Hamburg, Germany) solution (in 99% isopropanol) for 30 min at room temperature (RT), followed by immersion in a 60% isopropanol solution for 12 min. After the specimens were washed with deionized water for 3 min, counter-staining was conducted with hematoxylin (Carl Roth GmbH, Karlsruhe, Germany). The specimens were then mounted with mounting solution (Aquatex from Merck Millipore, Darmstadt, Germany), covered with a glass cover slip (Menzel-Graeser GmbH), and examined using a fully automated inverted light microscope for life science (DMI 6000 from Leica Microsystems Wetzlar, Germany). Image analysis was performed by grading the intensity of ORO staining (red color) of the Bruch's membrane (BrM) with scores ranging from 0 to 4, according to a qualitative evaluation assessed in four different regions in two separate slices from each eye (a total of 8 different regions from each eye). Qualitative ORO staining scores at the BrM and the choroid: 0=no staining; 1=+; 2=++; 3=+++; 4=++++.

For staining with filipin, specimens were washed once with deionized water for 5 min and then treated with 70% ethanol for 45 min. After being washed with deionized water for 5 min, the specimens were treated with cholesterol esterase (8.12 units/mL) diluted in 0.1 M potassium phosphate buffer (PPB, pH 7.4) for 3.5 hr at 37° C. The specimens were then washed sequentially with PPB and with phosphate buffered saline (PBS) twice for 3 min, followed by a wash with cold (4° C.) PBS overnight. Filipin staining was then performed with 250 µg/mL filipin (Sigma-Aldrich Biochemie GmbH, Hamburg, Germany), diluted in N,N-dimethylformamide (Merck Millipore, Darmstadt, Germany), for 60 min at RT with light shielding. The specimens were then washed sequentially with PBS and deionized water, mounted with a mounting solution (Mowiol®, Carl Roth GmbH, Karlsruhe, Germany), covered with a glass cover slip, and examined using an inverted fluorescence microscope (DMI 6000 from Leica Microsystems, Wetzlar, Germany). Filipin fluorescence was observed using a UV filter set ($\lambda$ex/$\lambda$em=350 nm/455 nm). As a negative control, cholesterol esterase was replaced by PBS, which prevented the release of cholesterol from cholesteryl ester and subsequent binding by filipin. Semiquantitative analysis of fluorescence intensity of filipin at three separate regions of the BrM was done on three different slides from the same eye (a total of 9 different regions from each eye).

Assays for immunohistochemistry of the membrane attack complex (MAC, C5b-9) and complement factor D (CFD) were performed identically except for employment of monoclonal antibodies specific for each complement component. Specimens were treated with 10 µg/mL protease K (Sigma-Aldrich Biochemie GmbH, Hamburg, Germany) in PBS for antigen retrieval for 30 min at RT. Subsequently the sections were blocked with a solution of goat serum (5% goat serum, 0.3% Triton X-100 in PBS) for 60 min at RT. The specimens were then reacted with a first antibody against either C5b-9 (diluted 1:30 in PBS, mouse monoclonal antibody, Dako Deutschland GmbH, Hamburg, Germany) or complement factor D (diluted 1:200 in PBS, mouse monoclonal antibody, Santa Cruz Biotechnology, Dallas, Tex., USA) overnight at 4° C. After being washed with PBS, the specimens were reacted with a second antibody (diluted 1:200 in PBS, Alexa Fluor 488 anti-mouse, Life Technologies Deutschland GmbH, Darmstadt, Germany) for 1 hr at 37° C. After the specimens were washed with PBS three times, nucleus staining was conducted with DAPI (1 µg/mL, Life Technologies GmbH, Darmstadt, Germany) for 10 min. The specimens then were washed with PBS three times, mounted with anti-fade solution (Mowiol®, Carl Roth GmbH, Karlsruhe, Germany), and covered with a glass cover slip for microscopic examination. Fluorescence microscopy was conducted using an inverted fluorescence microscope (DMI 6000 from Leica Microsystems, Wetzlar, Germany) and a filter set for $\lambda$ex/$\lambda$em=470 nm/525 nm. For the semiquantitative analysis of fluorescence intensity of C5b-9, 3-5 different regions in one slide were analyzed for 3 different slides from each eye (a total of 9-15 different regions from each eye). For the semiquantitative analysis of fluorescence intensity of complement factor D, 3 distinct regions for each eye were evaluated.

Figure 2:
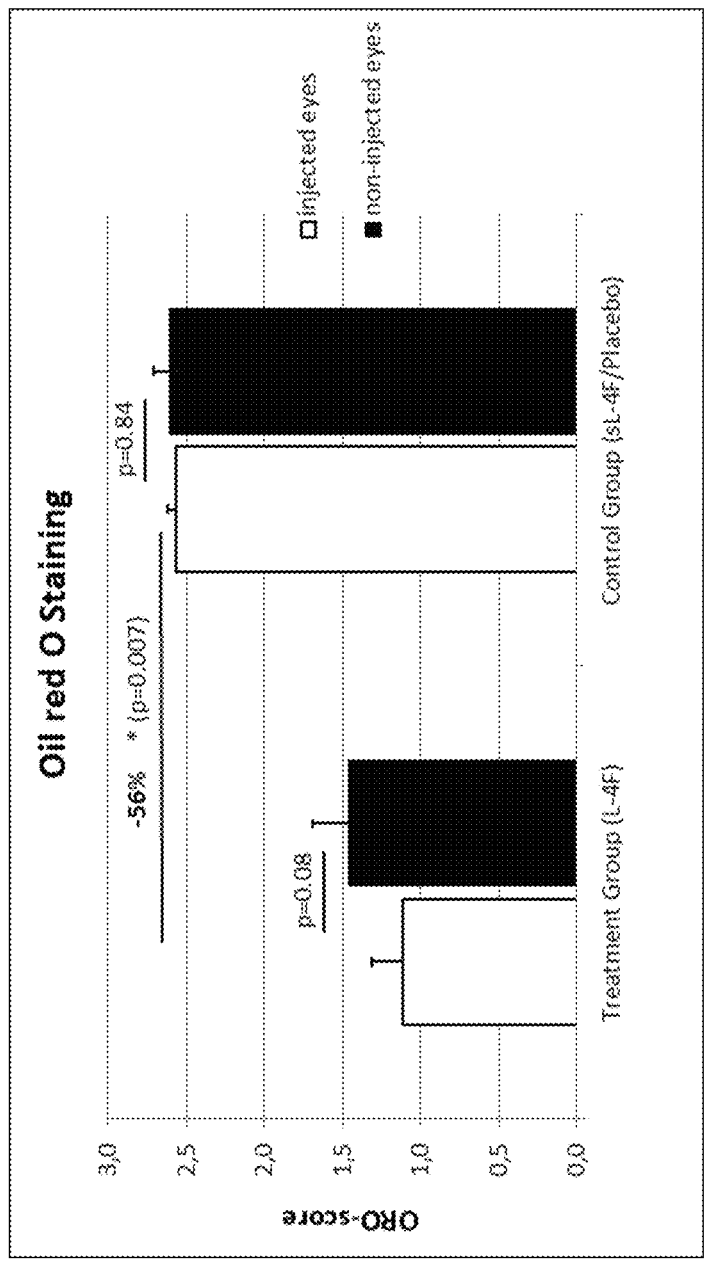
FIG. 2 shows the scoring of staining of neutral lipids in and on the Bruch's membrane with oil red O (ORO) in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.
Figure 3:
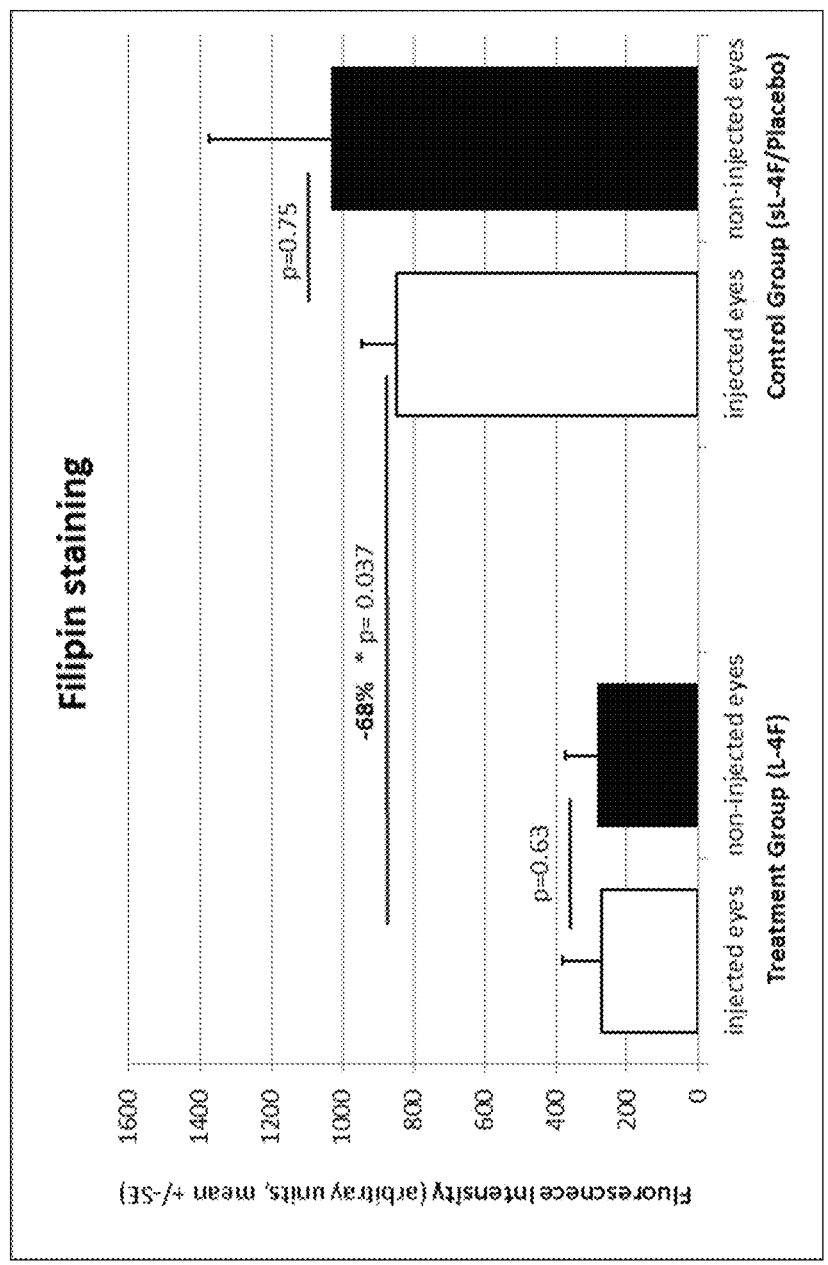
FIG. 3 shows the intensity of staining of esterified cholesterol in the Bruch's membrane with filipin in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.

Both control animals injected with the placebo (scrambled L-4F) exhibited in both eyes an intense and specific staining of the Bruch's membrane (BrM) and choriocapillaris with oil red O for neutral lipids and filipin for esterified cholesterol. For example, staining with oil red O showed that in both control animals, a large amount of lipids was present in and on the BrM. By contrast, in staining with oil red O eyes injected with L-4F exhibited a reduction of lipid deposits from the BrM by about 56% after 6 months compared to eyes injected with placebo. FIG. 2 shows the scoring of staining of neutral lipids in and on the Bruch's membrane with oil red 0 (ORO) in the injected eye and the fellow non-injected eye of macaques receiving 6 monthly intravitreal injections of L-4F or placebo (scrambled L-4F). Semiquantitative evaluation of filipin fluorescence revealed a reduction of esterified cholesterol in the BrM by about 68% in eyes injected with L-4F compared to placebo-injected eyes. FIG. 3 shows the intensity of staining of esterified cholesterol in the Bruch's membrane with filipin in the injected eye and the fellow non-injected eye of macaques receiving 6 monthly intravitreal injections of L-4F or placebo (scrambled L-4F).

Figure 4:
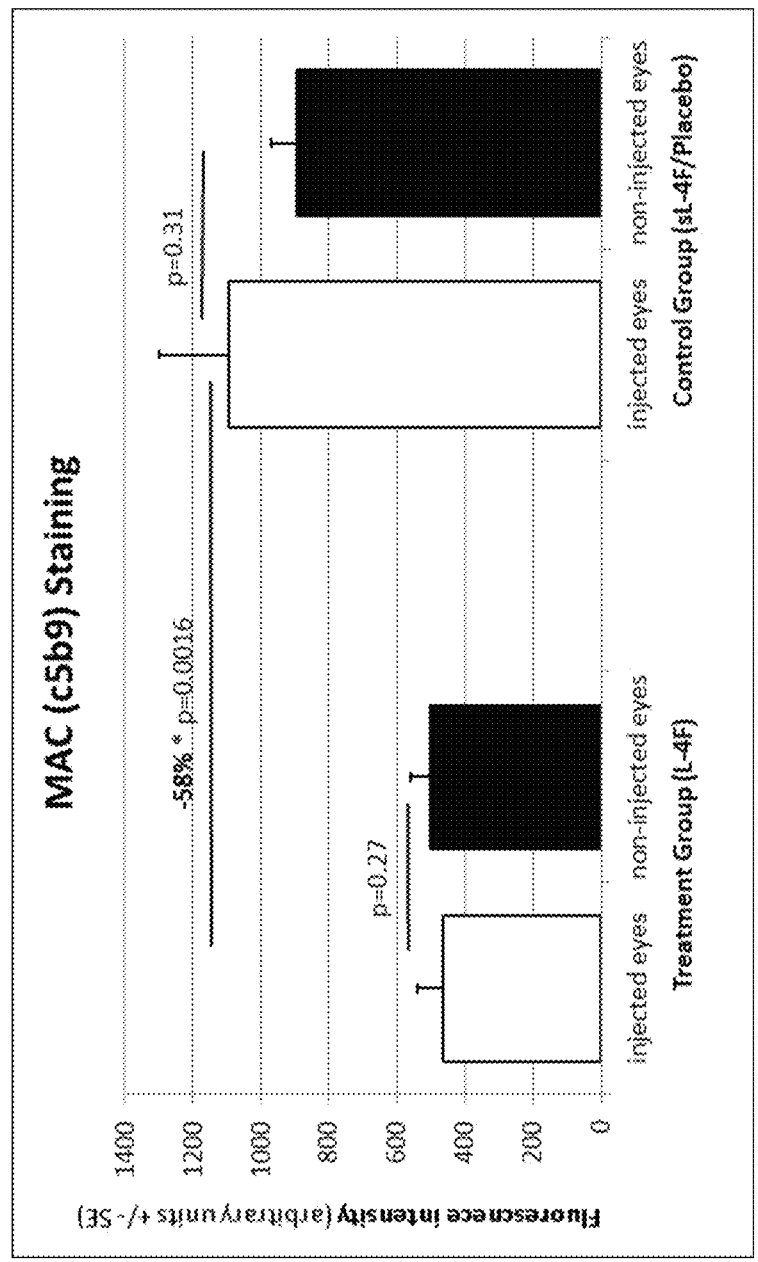
FIG. 4 shows the intensity of staining of the membrane attack complex (MAC, C5b-9) in the Bruch's membrane and the choriocapillaris in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.
Figure 5:
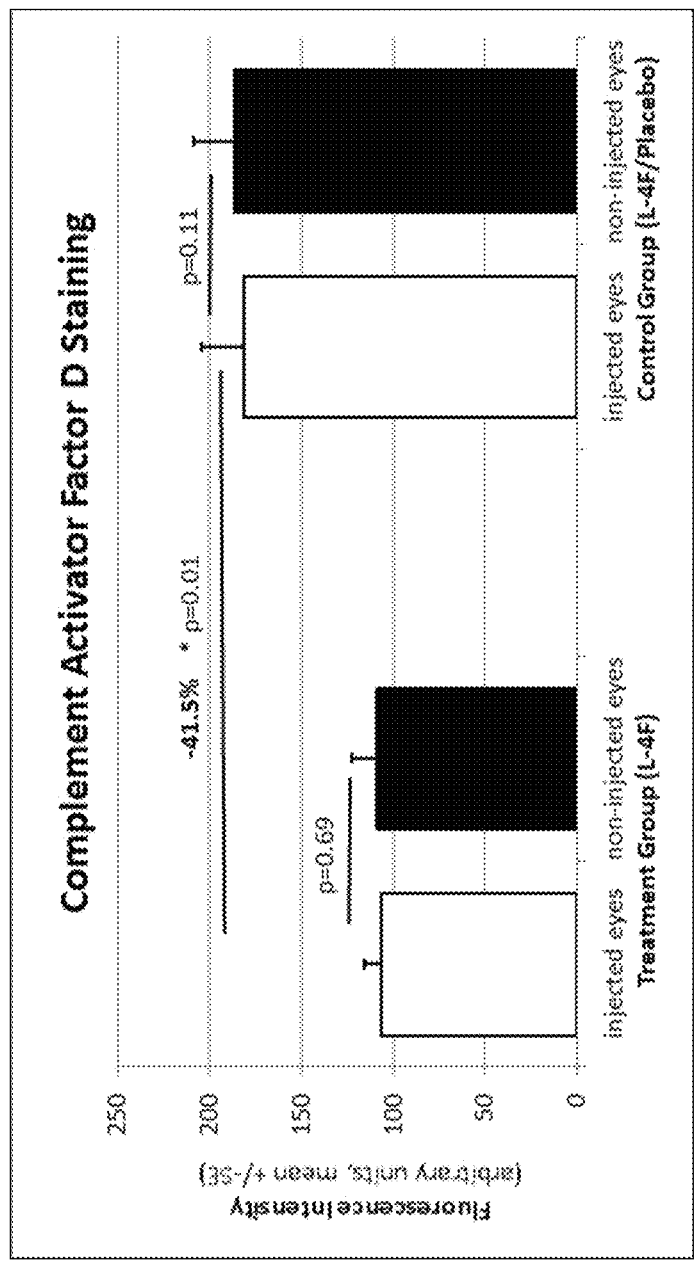
FIG. 5 shows the intensity of staining of complement factor D in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.

Through semiquantitative analysis of fluorescence intensity of the respective specific antibodies, eyes injected with L-4F exhibited a decreased level of MAC (C5b-9) in the BrM and the choriocapillaris by about 58% and a decreased level of complement factor D by about 41% compared to eyes injected with the scrambled peptide. FIG. 4 shows the intensity of staining of the membrane attack complex (MAC, C5b-9) in the Bruch's membrane and the choriocapillaris in the injected eye and the fellow non-injected eye of macaques receiving 6 monthly intravitreal injections of L-4F or placebo (scrambled L-4F). FIG. 5 shows the intensity of staining of complement factor D in the injected eye and the fellow non-injected eye of macaques receiving 6 monthly intravitreal injections of L-4F or placebo (scrambled L-4F).

Figure 6:
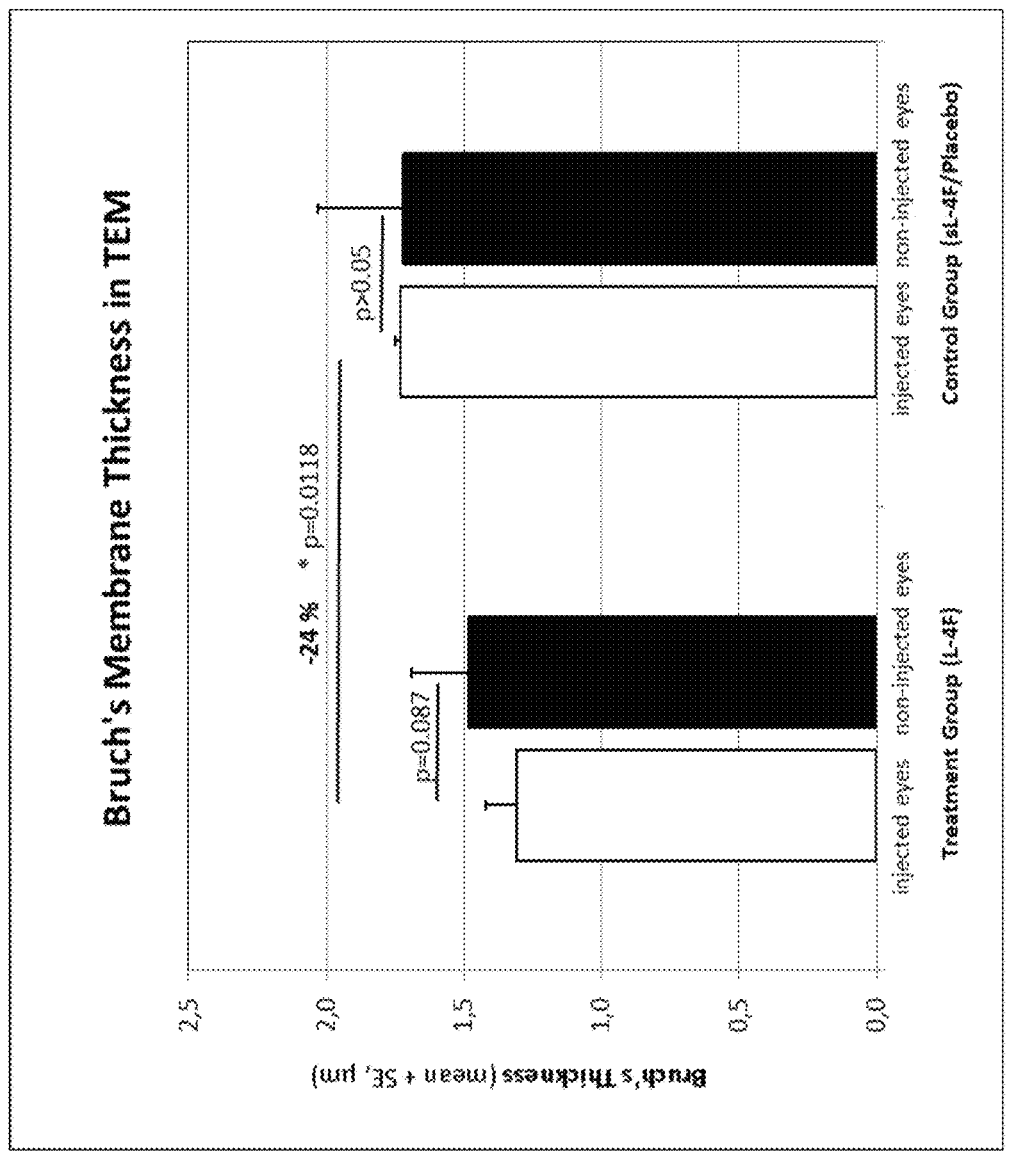
FIG. 6 shows the thickness of the Bruch's membrane measured at the temporal outer macula in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.

Lipid deposition in the Bruch's membrane contributes to thickening of the BrM. Bruch's membrane thickness was measured at the temporal outer macula of enucleated eyes examined by electron microscopy post-mortem. Eyes injected with L-4F exhibited reduction of BrM thickness (1.31 µm±SE 0.11) by about 24% compared to eyes injected with placebo (1.73 µm±SE 0.02). FIG. 6 shows the thickness of the Bruch's membrane measured at the temporal outer macula in the injected eye and the fellow non-injected eye of macaques receiving 6 monthly intravitreal injections of L-4F or placebo (scrambled L-4F).

L-4F had similar effects on the fellow non-injected eye as on the injected eye after 6 monthly intravitreal injections (see FIGS. 2-6). Without intending to be bound by theory, L-4F intravitreally injected into one eye reached the BrM and from there could have entered the choriocapillaris and hence systemic circulation and ultimately the fellow non-injected eye. Also without intending to be bound by theory, the magnitude of L-4F's therapeutic effects in the fellow non-injected eye could have been due in part to the relatively small body weight of the macaques relative to eye size and the primarily vegetarian diet of the macaques, which exhibited no atherosclerosis, a potential target for L-4F in systemic circulation.

L-4F was well tolerated in all of the macaques, as none of the macaques intravitreally injected with L-4F experienced any significant adverse event or side effect. For example, 6 monthly intravitreal injections of L-4F did not increase the blood level of high-sensitivity C-reactive protein (hsCRP) compared to the blood level of hsCRP on the day prior to the first injection of L-4F. Circulating hsCRP, which is mainly produced in the liver, is a non-specific marker for systemic inflammation.

In summary, the apoA-I mimetic L-4F functioned as an effective lipid scavenger and removed lipid deposits from the BrM in a monkey model of age-related maculopathy. Removal of lipid deposits from the BrM restored BrM integrity as examined by electron microscopy. In addition, downstream effects of lipid deposition such as local inflammation were reduced, as demonstrated by the marked reduction of complement activation in eyes injected with L-4F.

Example 2. Phase III Safety/Efficacy Studies of L-4F Alone

Randomized, open-label, dose-escalation Phase I/II studies are conducted to evaluate the safety, tolerability, pharmacokinetics and effective dose of L-4F or a variant (e.g., D-4F) or a salt (e.g., acetate salt) thereof administered (e.g., by intravitreal injection) to patients with AMD (e.g., intermediate-stage AMD). Soft drusen are a high-risk factor for progression of AMD and are clinically well-recognized lipid-rich sub-RPE-BL deposits that are hallmarks for AMD. The cumulative dose of L-4F until drusen reduction as well the maximum tolerated dose provide important information about the optimum L-4F dose(s) in other studies, including those where L-4F (or a variant or salt thereof) is administered in combination with one or more other therapeutic agents (e.g., an anti-angiogenic agent or a complement inhibitor) for the treatment of neovascular (wet) AMD or atrophic (dry) AMD.

In Phase I/II studies, L-4F or a variant (e.g., D-4F) or a salt (e.g., acetate salt) thereof is administered in a certain frequency (e.g., monthly or bimonthly) by intravitreal injection into one eye in certain doses (e.g., escalating doses from about 0.1 mg to about 1.5 mg) for a certain period of time (e.g., about 6, 9 or 12 months). The other eye is not injected and serves as intra-individual control eye. Post-treatment evaluation is conducted up to, e.g., about 12 months. Primary outcome measures include, e.g., reduction of soft drusen (e.g., reduction of total drusen volume by about 30%) as quantified by spectral domain optical coherence tomography (SDOCT) and stability of or increase in quantitative fundus autofluorescence (qAF) intensity (time frame of, e.g., about 15 months). Secondary outcome measures include, e.g., stability or improvement of vision, such as metamorphopsia, dark adaptometry and best-corrected visual acuity (BCVA) from baseline at, e.g., about 9 and 15 months.

Example 3. Phase II Efficacy Study of L-4F in Combination with an Anti-Angiogenic Agent A Phase II study is conducted to evaluate preliminary and confirmatory efficacy of L-4F or a variant (e.g., D-4F) or a salt (e.g., acetate salt) thereof in combination with an anti-angiogenic agent (e.g., an anti-VEGF agent, such as aflibercept [EYLEA®], bevacizumab [AVASTIN®] or ranibizumab [LUCENTIS®]) in patients who have neovascular (wet) AMD. The drugs are administered (e.g., by intravitreal injection) in a certain frequency (e.g., monthly or bimonthly) until exudation from neovascularization (e.g., type 1, 2 or 3 neovascularization) stops. Post-treatment evaluation is performed. The drugs are injected into the worse eye, and the other eye is not injected and serves as intra-individual control eye. Goals include decreasing the dosage and the number of injections of the anti-VEGF agent required for curtailing neovascularization.

Example 4. Phase II Efficacy Study of L-4F in Combination with a Complement Inhibitor A Phase II study is conducted to evaluate preliminary and confirmatory efficacy of L-4F or a variant (e.g., D-4F) or a salt (e.g., acetate salt) thereof in combination with a complement inhibitor (e.g., lampalizumab, ARC1905 [Zimura®] or LFG316) in patients who have intermediate-stage or advanced-stage atrophic (dry) AMD and exhibit non-central or central geographic atrophy (GA). The drugs are administered (e.g., by intravitreal injection) in a certain frequency (e.g., monthly or bimonthly) to assess their efficacy in slowing the progression of non-central or central GA (e.g., reduce the rate of GA progression, or reduce the GA lesion area or size). Post-treatment evaluation is performed. The drugs are injected into the worse eye, and the other eye is not injected and serves as intra-individual control eye. Goals include decreasing the dosage and the number of injections of the complement inhibitor required for slowing the progression of non-central or central GA.

It is understood that, while particular embodiments have been illustrated and described, various modifications may be made thereto and are contemplated herein. It is also understood that the disclosure is not limited by the specific examples provided herein. The description and illustration of embodiments and examples of the disclosure herein are not intended to be construed in a limiting sense. It is further understood that all aspects of the disclosure are not limited to the specific depictions, configurations or relative proportions set forth herein, which may depend upon a variety of conditions and variables. Various modifications and variations in form and detail of the embodiments and examples of the disclosure will be apparent to a person skilled in the art. It is therefore contemplated that the disclosure also covers any and all such modifications, variations and equivalents.

---

What is claimed is:

1. A method of treating age-related macular degeneration (AMD), comprising administering to a human subject afflicted with AMD a therapeutically effective amount of an apolipoprotein (apo) mimetic, wherein the apo mimetic is administered locally to, into, in or around the eye in a total dose from 1 mg±10% to 10 mg±10% over a period of 6 months.

2. The method of claim 1, wherein the apo mimetic comprises an apoA-I mimetic and/or an apoE mimetic.

3. The method of claim 2, wherein the apoA-I mimetic comprises 4F or a variant or salt thereof, and the apoE mimetic comprises AEM-28-14 or a variant or salt thereof.

4. The method of claim 3, wherein the apo mimetic comprises L-4F or D-4F or a salt thereof, optionally having a protecting group at the N-terminus and/or the C-terminus.

5. The method of claim 1, wherein the apo mimetic is administered locally in a total dose of 1-5 mg±10% or 5-10 mg±10% over a period of 6 months.

6. The method of claim 1, wherein the apo mimetic is administered locally by injection, eye drop or implant.

7. The method of claim 1, wherein the apo mimetic is administered locally by injection once every month (4 weeks), 1.5 months (6 weeks), 2 months (8 weeks), 2.5 months (10 weeks), 3 months (12 weeks), 4 months, 5 months or 6 months.

8. The method of claim 1, wherein the apo mimetic is administered locally in a total of 3-6, 6-9, 9-12 or 12-15 injections.

9. The method of claim 1, wherein the treatment regimen with the apo mimetic lasts for 6-12, 12-18, 18-24, 24-30 or 30-36 months.

10. The method of claim 9, wherein the apo mimetic is administered locally in a total dose of 1-5 mg±10%, 5-10 mg±10%, 10-15 mg±10% or 15-20 mg±10% for the entire treatment regimen.

11. The method of claim 1, wherein the apo mimetic is administered locally at least in the advanced stage of AMD to treat central geographic atrophy (GA) and/or to prevent or forestall neovascular AMD, and/or to treat neovascular AMD.

12. The method of claim 1, wherein the apo mimetic is administered locally at least in the intermediate stage of AMD to treat non-central GA and/or to prevent or forestall central GA and/or neovascular AMD, or is administered in the initial phase of intermediate AMD to prevent or forestall non-central GA.

13. The method of claim 1, wherein the apo mimetic is administered locally at least in the early stage of AMD to prevent or forestall non-central GA.

14. The method of claim 1, wherein the apo mimetic is administered locally in a fixed-routine regimen, an as-needed regimen or a treat-and-extend regimen.

15. The method of claim 1, further comprising administering one or more additional therapeutic agents.

16. The method of claim 15, wherein the one or more additional therapeutic agents are selected from the group consisting of anti-dyslipidemic agents, PPAR-α agonists, PPAR-δ agonists, PPAR-γ agonists, anti-amyloid agents, inhibitors of lipofuscin or components thereof, antioxidants, neuroprotectors (neuroprotectants), apoptosis inhibitors, necrosis inhibitors, C-reactive protein inhibitors, inhibitors of the complement system or components thereof, inhibitors of inflammasomes, anti-inflammatory agents, immunosuppressants, modulators of matrix metalloproteinases, anti-angiogenic agents, and RPE cell replacement therapies.

17. A method of treating age-related macular degeneration (AMD), comprising administering to a human subject afflicted with AMD a therapeutically effective amount of an apolipoprotein (apo) mimetic and a therapeutically effective amount of an anti-angiogenic agent, wherein:

the apo mimetic and the anti-angiogenic agent are administered locally to, into, in or around the eye; and the apo mimetic is administered in a total dose from 1 mg±10% to 10 mg±10% over a period of 6 months.

18. The method of claim 17, wherein the apo mimetic comprises L-4F or D-4F or a salt thereof and/or AEM-28-14 or a salt thereof.

19. The method of claim 17, wherein the anti-angiogenic agent comprises aflibercept, bevacizumab or ranibizumab, or any combination or all thereof.

20. The method of claim 17, wherein the apo mimetic and the anti-angiogenic agent are administered to treat neovascular AMD.

21. A method of treating age-related macular degeneration (AMD), comprising administering to a human subject afflicted with AMD a therapeutically effective amount of an apolipoprotein (apo) mimetic and a therapeutically effective amount of a complement inhibitor, wherein:

the apo mimetic and the complement inhibitor are administered locally to, into, in or around the eye; and the apo mimetic is administered in a total dose from 1 mg±10% to bout 10 mg±10% over a period of 6 months.

22. The method of claim 21, wherein the apo mimetic comprises L-4F or D-4F or a salt thereof and/or AEM-28-14 or a salt thereof.

23. The method of claim 21, wherein the complement inhibitor comprises lampalizumab, LFG316 or ARC1905, or any combination or all thereof.

24. The method of claim 21, wherein the apo mimetic and the complement inhibitor are administered to prevent, delay the onset of, or slow the progression of central geographic atrophy (GA) and/or non-central GA.

* * * * *

UNITED STATES PATENT AND TRADEMARK OFFICE
CERTIFICATE OF CORRECTION

Page 1 of 1

PATENT NO. : 10,426,817 B2
APPLICATION NO. : 15/414422
DATED : October 1, 2019
INVENTOR(S) : Martin Rudolf and Keith Roizman It is certified that error appears in the above-identified patent and that said Letters Patent is hereby corrected as shown below:

In the Claims

In Claim 21, Line 9, remove the word "bout".

Signed and Sealed this
Twelfth Day of November, 2019

Andrei Iancu
*Director of the United States Patent and Trademark Office*